(12) United States Patent
Okuno et al.

(10) Patent No.: US 7,344,856 B1
(45) Date of Patent: Mar. 18, 2008

(54) METHOD OF CONTROLLING CLEAVAGE BY OMPT PROTEASE

(75) Inventors: Kazuaki Okuno, Tatebayashi (JP); Masayuki Yabuta, Tatebayashi (JP); Kazuhiro Ohsuye, Ohta (JP)

(73) Assignee: Asubio Pharma Co. Ltd. (JP)

( * ) Notice: Subject to any disclaimer, the term of this patent is extended or adjusted under 35 U.S.C. 154(b) by 0 days.

(21) Appl. No.: 09/674,777

(22) PCT Filed: Mar. 3, 2000

(86) PCT No.: PCT/JP00/01309

§ 371 (c)(1),
(2), (4) Date: Jan. 7, 2002

(87) PCT Pub. No.: WO00/52193

PCT Pub. Date: Sep. 8, 2000

(30) Foreign Application Priority Data

Mar. 4, 1999 (JP) ................................. 11-057731

(51) Int. Cl.
C12P 21/06 (2006.01)
C12P 21/00 (2006.01)
C12N 9/48 (2006.01)
C12N 1/20 (2006.01)
C12N 15/00 (2006.01)

(52) U.S. Cl. .................. 435/69.1; 435/70.1; 435/71.1; 435/440; 435/212; 435/252.33; 435/325

(58) Field of Classification Search ................. 435/212
See application file for complete search history.

(56) References Cited

FOREIGN PATENT DOCUMENTS

| EP | 0 700 995 A2 | 3/1996 |
|---|---|---|
| EP | 0 978 565 A1 | 2/2000 |
| WO | WO 98/49286 A | 11/1998 |

OTHER PUBLICATIONS

Lassen SF, Mortensen KK, Sperling-Petersen HU. OmpT proteolysis of *E. coli* initiation factor IF2. Elimination of a cleavage site by site-directed mutagenesis. Biochem Int. Aug. 1992;27(4):601-11.*
Zhao GP, Somerville RL. An amino acid switch (Gly281→Arg) within the "hinge" region of the tryptophan synthase beta subunit creates a novel cleavage site for the OmpT protease . . . J Biol Chem. Jul. 15, 1993;268(20):14912-20.*
Ausubel et al Mutagenesis of cloned DNA. Chapter 8. 1987. In Current Protocols in Molecular Biology Wiley, Inc.*
Hanke et al Processing by OmpT of fusion proteins carrying the HlyA transport signal during secretion by the *Escherichia coli* hemolysin transport system. Mol Gen Genet. May 1992;233(1-2):42-8.*
Yabuta et al Hyperproduction of a recombinant fusion protein of *Staphylococcus aureus* V8 protease in *Escherichia coli* and its processing by OmpT protease to release an active V8 protease derivative. Appl Microbiol Biotechnol. Dec. 1995;44(1-2):118-25.*

Maurer et al., Autodisplay: one-component system for efficient surface display and release of soluble recombinant proteins from *Escherichia coli*. J Bacteriol. Feb. 1997;179(3):794-804.*
Sugimura et al., Purification, characterization, and primary structure of *Escherichia coli* protease VII with specificity for paired basic residues: identity of protease VII and OmpT. J Bacteriol. Dec. 1988;170(12):5625-32.*
Sedgwick, B., In vitro proteolytic cleavage of the *Escherichia coli* Ada protein by the ompT gene product. J Bacteriol. Apr. 1989;171(4):2249-51.*
Yabuta M., et al., "Hyperproduction of a recombinant fusion protein of *Staphylococcus aureus* V8 protease in *Escherichia coli* and its processing by OmpT protease to release an active V8 protease derivative", Appl.Microbiol.Biotech., vol. 44, p. 118-125 (1995).
Zhao Guo-Ping et al., "An amino acid switch (Gly-231) fwdarw Arg) within the hinge region of the tryptophan systhase beta subunit creates a novel cleavage site for the OmpT protease and selectively diminishes affinity toward a specific monoclonal antibody.", J.Biol. Chem., vol. 268, No. 20, p. 14912-14920 (1993).
Jennifer Grodberg and John J. Dunn, "*ompT* Encodes the *Escherichia coli*Outer Membrane Protease That Cleaves T7 RNA Polymerase during Purification," Journal of Bacteriology, Mar. 1988, vol. 170, No. 3, pp. 1245-1253.
Keijiro Sugimura and Naoki Higashi, "A Novel Outer-Membrane-Associated Protease in *Escherichia coli*", Journal of Bacteriology, Aug. 1988, vol. 170, No. 8, pp. 3650-3654.
White et al., "A Novel Activity of OmpT, Proteolysis Under Extreme Denaturing Conditions," The Journal of Biological Chemistry, Jun. 1995, vol. 270, No. 22, pp. 12990-12994.
Dalphin et al. (Apr. 1992) "Proteolysis of Bacteriophage ΦX174 Prohead Accessory Protein gpB by *Escherichia coli* OmpT Protease Is Not Essential for Phage Maturation in Vivo." Journal of Bacteriology 174(7): 2404-2406.
Lassen, Søren Flensted et al., "OmpT Proteolysis of *E. Coli* Initiation Factor IF2 Elimination of a cleavage site by site-directed mutagenesis", Biochemistry International, (1992), vol. 27, Issue No. 4, pp. 601-611, Academic Press Australia.
Okuno Kazuaki et al., "Substrate Specificity at the P1'site of *Escherichia coli* OmpT under Denaturing Conditions", Bioscience Biotechnology and Biochemistry, (Jan. 2002), vol. 66, Issue No. 1, pp. 127-134, Portland Press Ltd.
Okuno Kazuaki et al., "An analysis of target preferences of *Escherchia coli* outer-membrane endoprotease OmpT for use in therapeutic peptide production: efficient cleavage of substrates with basic amiono acids at the P4 and P6 positions", Biotechnology and Applied Biochemistry, (Oct. 2002), vol. 36, Issue No. 2, pp. 77-84.

* cited by examiner

*Primary Examiner*—Sheridan Swope
(74) *Attorney, Agent, or Firm*—Hunton & Williams LLP

(57) ABSTRACT

Methods of using OmpT protease are provided. In particular, the invention provides for a method of controlling cleavage of a polypeptide by OmpT protease comprising, converting a sequence site comprising two arbitrary consecutive amino acids and/or amino acid(s) in the vicinity of the site in the polypeptide into other amino acids; which method comprises setting lysine or arginine as the amino acid at the −1-position concerning the site and setting a specific amino acid as the amino acid at the +1-position; and/or setting specific amino acid(s) as the amino acid(s) at the −4-position and/or the −6-position relative to the site; so that a desired part of the polypeptide is cleaved by OmpT protease and/or an undesired part of the polypeptide is not (or hardly) cleaved by OmpT protease. A method of producing a target polypeptide is also provided.

10 Claims, 37 Drawing Sheets

```
                                                              15
Met Thr Met Ile Thr Asp Ser Leu Ala Val Val Leu Gln Arg Lys
                                                              30
Asp Trp Glu Asn Pro Gly Val Thr Gln Leu Asn Arg Leu Ala Ala
                                                              45
His Pro Pro Phe Ala Ser Trp Arg Asn Ser Asp Asp Ala Arg Thr
                                                              60
Asp Arg Pro Ser Gln Gln Leu Arg Ser Leu Asn Gly Glu Trp Arg
                                                              75
Phe Ala Trp Phe Pro Ala Pro Glu Ala Val Pro Glu Ser Leu Leu
                                                              90
Asp Leu Pro Glu Ala Asp Thr Val Val Val Pro Asp Ser Ser Asn
                                                             105
Trp Gln Met His Gly Tyr Asp Ala Pro Ile Tyr Thr Asn Val Thr
                                                             120
Tyr Pro Ile Thr Val Asn Pro Pro Phe Val Pro Thr Glu Pro His
                                                             135
His His His Pro Gly Gly Arg Gln Met His Gly Tyr Asp Ala Glu
                                                             150
Leu Arg Leu Tyr Arg ↓ Arg His His Gly Ser Gly Ser Pro Ser Arg
                                                             165
His Pro Arg His Ala Glu Gly Thr Phe Thr Ser Asp Val Ser Ser
                                                             180
Tyr Leu Glu Gly Gln Ala Ala Lys Glu Phe Ile Ala Trp Leu Val

Lys Gly Arg Gly
```

Fig. 4

```
                                              15
Met Thr Met Ile Thr Asp Ser Leu Ala Val Val Leu Gln Arg Arg
                                              30
Asp Trp Glu Asn Pro Gly Val Thr Gln Leu Asn Arg Leu Ala Ala
                                              45
His Pro Pro Phe Ala Ser Trp Arg Asn Ser Glu Glu Ala Arg Thr
                                              60
Asp Arg Pro Ser Gln Gln Leu Arg Ser Leu Asn Gly Glu Trp Arg
                                              75
Phe Ala Trp Phe Pro Ala Pro Glu Ala Val Pro Glu Ser Leu Leu
                                              90
Glu Leu Pro Glu Ala Asp Thr Val Val Val Pro Asp Ser Ser Asn
                                             105
Trp Gln Met His Gly Tyr Asp Ala Gln Phe Arg ↓ Ser Leu Arg Arg
                                             120
Ser Ser Cys Phe Gly Gly Arg Met Asp Arg Ile Gly Ala Gln Ser

Gly Leu Gly Cys Asn Ser Phe Arg Tyr
```

Fig. 21

METHOD OF CONTROLLING CLEAVAGE BY OMPT PROTEASE

CROSS-RELATED AND PRIORITY APPLICATIONS

This application is a national phase application of PCT Application No. PCT/JP00/01309, filed Mar. 3, 2000, which claims the benefit of Japanese Application No. 57731/1999, filed Mar. 4, 1999.

BACKGROUND OF THE INVENTION (1) Field of the Invention

This invention relates to a method of controlling cleavage of a polypeptide by OmpT protease using novel cleavage and recognition sites which have been found by examining the substrate specificity of *Escherichia coli* OmpT protease.

In one aspect, the present invention relates to a method of cleaving polypeptides by using OmpT protease. More particularly, it relates to a method of cleaving polypeptides by utilizing novel cleavage and recognition sites of OmpT protease.

In another aspect, the present invention relates to a method of excising physiologically active peptides, proteins and derivatives thereof from fusion proteins with the use of OmpT protease. More particularly, the present inventors examined the substrate specificity of OmpT protease to find a novel cleavage method, cleavage sites and recognition sites. Thus, one embodiment of the invention relates to a method of efficiently producing physiologically active peptides, a protein and derivatives thereof from fusion proteins by using the properties of the novel cleavage sites and recognition sites.

The present invention further relates to a method of avoiding cleavage of polypeptides by OmpT protease at undesired sites. In particular, it relates to a method of avoiding cleavage of physiologically active peptides, proteins or derivatives thereof by OmpT protease produced by host cells. Thus, the present invention provides a method of making the physiologically active peptides, proteins or derivatives thereof not (or hardly) cleavable by OmpT protease by converting the amino acid sequences at the OmpT protease cleavage sites or in the vicinity thereof.

(2) Description of the Related Art

*E. coli* OmpT protease is an *E. coli* outer membrane protease that selectively cleaves mainly bonds between basic amino acid pairs (Sugimura, K. and Nishihara, T. J. Bacteriol. 170: 5625-5632, 1988). This enzyme has a molecular weight of 36,000 and seemingly falls within the category of serine proteases. Sugimura et al. examined the substrate specificity of this OmpT protease and reported that the enzyme specifically cleaves the peptide bonds at the center of basic amino acid pairs of arginine-arginine, lysine-lysine, arginine-lysine and lysine-arginine. In addition, cleavage sites in amino acid sequences other than the above pairs has been found. Namely, it has been reported that cleavage by OmpT protease arises at arginine-methionine (Zhao, G-P. and Somerville, R. L. J. Biol. Chem. 268, 14912-14920, 1993), arginine-alanine (Lassen, S. F. et al. Biochem. Int. 27: 601-611, 1992) and arginine-valine (Maurer, J. J. Bacteriol. 179: 794-804, 1997). This protease is characterized in that it cleaves not all proteins and peptides containing these sequences but exclusively cleaves specific proteins and peptides at specific sites. For example, γ-interferon contains the sequences described above at 11 sites but only 2 sites among them are exclusively cleavable by OmpT protease (Sugimura, K. and Higashi, N.J. Bacteriol. 170: 3650-3654, 1988). T7 RNA polymerase contains the sequences described above at 17 sites but only 2 sites among them are exclusively cleavable therewith (Grodberg, J. and Dunn, J. J. J. Bacteriol. 170: 1245-1253, 1988). The above-described data indicates that the known information on the cleavage sites of OmpT protease is not applicable to estimation of cleavage sites of OmpT protease. That is, OmpT protease differs from enzymes such as AP-1 and trypsin which are commonly employed in peptide mapping of proteins, in that the cleavage site of AP-1 and trypsin can be estimated on the basis of known data. Since the cleavage by OmpT protease arises at specific sites of proteins or peptides, it is anticipated that amino acid sequences other than the amino acid sequences as described above (namely, the N-terminal and C-terminal amino acid sequences of the cleavage site) may participate in the cleavage. However, it still remains unknown so far what amino acid sequence allows (or does not allow) the cleavage.

However, OmpT protease has found use in excising target polypeptides from fusion proteins constructed by gene recombination techniques, since it has high specificity to cleavage sites and is one of endogenous proteases of *E. coli*. In order to produce cholesterol esterase by using *E. coli*, Hanke et al. prepared a fusion protein consisting of the esterase and *E. coli* hemolysin A protein. The fusion protein was secreted in culture supernatant, and then cleaved by the outer membrane protease OmpT. Consequently, they could obtain active cholesterol esterase successfully. Hanke et al. employed a linker having an arginine-lysine sequence and cleaved this sequence by OmpT protease (Hanke, C et. al. Mol. Gen. Genet. 233: 42-48, 1992).

The present inventors found that OmpT protease is resistant to denaturing agents and that fusion proteins expressed as inclusion bodies can be cleaved in the presence of a denaturing agent by taking advantage of the above property. Namely, the present inventors successfully produced a V8 protease derivative having enzymatic activity by expressing an *S. aureus* V8 protease derivative fusion protein as an inclusion body in an *E. coli* expression system, solubilizing the same by urea, releasing the V8 protease derivative moiety from the fusion protein by using OmpT protease in the presence of urea and finally refolding (Yabuta, M., Ochi, N. and Ohsuye, K. Appl. Microbiol. Biotechnol. 44:118-125, 1995).

To release target peptides or target proteins from fusion proteins, it has been a practice to employ enzymes having high specificity to amino acid sequences. Known examples of proteases employed for this purpose include Xa factor, thrombin, enterokinase and the like which are enzymes originating in mammals and are supplied only in a small amount at a high cost. Therefore, these enzymes are unsuitable for the industrial treatment of peptides and proteins by the fusion protein method on a mass scale. When the target peptide or protein is to be used as a medicine, it is also required to take into consideration viral contamination originating in the enzymes. In contrast thereto, OmpT protease is clearly superior to these enzymes in supply, cost and safety because of its origination in *E. coli*.

However, the substrate specificity of this protease has not been sufficiently studied yet and, therefore, it is difficult at the present stage to arbitrarily design the cleavage site at the desired part to be excised. Moreover, OmpT protease cleaves not all of the sequences reported above (i.e., arginine-arginine, lysine-lysine, arginine-lysine, lysine-arginine, arginine-methionine, arginine-alanine and arginine-valine) but exclusively specific sites in proteins. When one of sequences consisting of these two amino acids is merely located in a linker site of fusion proteins, therefore, this site cannot always be cleaved by OmpT protease. Even though it can be cleaved, OmpT protease cleaves the peptide bond at the center of the cleavage site consisting of two amino acids. Therefore, the amino acid located at the +1-position of the cleavage site will remain as the N-terminus of the target polypeptide when this enzyme releases the target polypeptide from a fusion protein consisting of a protective peptide, a linker peptide including the OmpT protease cleavage site, and a target polypeptide in this order. Moreover, this added amino acid cannot be arbitrarily selected but restricted to arginine, lysine, valine, alanine or methionine on the basis of the recognition sequences of OmpT protease reported hitherto. These properties of OmpT protease are unfavorable as a protease to be used in cleaving fusion proteins.

On the other hand, it is known that the cleavage efficiency of papain, which is a protease, is affected not only by the sequence of the cleavage site in the substrate but also by the amino acid sequences in the vicinity thereof (Schechter, I. and Berger, A. Biochem. Biophys. Res. Commun. 27: 157-162 1967). Recently, detailed studies have also been made on Kex2 (Rockwell, N. C., Wang, G. T., Krafft, G. A. and Fuller, R. S. Biochemistry 36, 1912-1917 1997) and furin (Krysan, D. J., Rockwell, N. C. and Fuller, R. S. J. Biol. Chem. 274, 23229-23234 1999) which are proteases cleaving the C-terminal side of basic amino acid pairs. In Kex2 and furin, the consensus sequences at the cleavage sites and amino acid sequences in the vicinity thereof have been clarified by comparing the amino acid sequences of the substrates. In the case of OmpT protease, it is considered, on the basis of the comparison of the substrates known hitherto, that arginine or lysine is essentially required as the amino acid at the 1-position in the N-terminal side of the cleavage site but no other clear consensus sequence has been found out so far. Although it is presumed that the recognition of the cleavage site and the cleavage efficiency of OmpT protease might be also affected not only by the cleavage site in the substrate but also by the amino acid sequences in the vicinity thereof, it is impossible at the present stage to control the cleavage by OmpT protease by using these properties.

In the present invention, the location of each amino acid in a given polypeptide is represented as follows. A sequence site consisting of two arbitrary consecutive amino acids in the polypeptide is referred to as the cleavage site or the site to be cleaved by OmpT protease. Between the amino acids concerning this site, the amino acid in the N-terminal side is referred to as the −1-position while the amino acid in the C-terminal side is referred to as the +1-position. The amino acids at the 1st, 2nd, 3rd, and so on in the N-terminal side of this site are referred to respectively as the amino acids at the −1-, −2-, −3-positions and so on, while the amino acids at the 1st, 2nd, 3rd, and so on in the C-terminal side of this site are referred to respectively as the amino acids at the +1-, +2-, +3-positions and so on. When an amino acid substitution is introduced into this site or in the vicinity thereof so that the site becomes not cleavable or cleavable, the corresponding amino acids in the sequence are represented by the above-described numbering.

For example, when the amino acid sequence leucine-tyrosine-lysine-arginine-histidine is to be cleaved at the bond between lysine and arginine (i.e., the two arbitrary consecutive amino acids), leucine, tyrosine, lysine, arginine and histidine serve respectively as the amino acids at the −3-, −2-, −1-, +1- and +2-positions.

SUMMARY OF THE INVENTION

As described above, OmpT protease is highly useful. However, when OmpT protease is used as an enzyme in cleaving fusion proteins, several problems have arisen. Such problems include that it is unknown how to design the amino acid sequence at the cleavage site to enable specific cleavage, that the target peptides obtained by the cleavage are restricted due to the restriction on the N-terminal amino acids of the target peptides, and that cleavage cannot be efficiently performed. However, it is expected that these problems can be solved by further studying the amino acid sequences at the cleavage site and in the vicinity thereof and by establishing a novel cleavage method or novel recognition/cleavage sequences, thereby making OmpT protease more useful in cleaving fusion proteins.

On the contrary, the cleavage by OmpT protease is sometimes problematic when producing peptides or proteins by using E. coli. The cleavage by OmpT protease may be avoided by, for example, using an OmpT protease-deficient E. coli strain as a host or by adding an OmpT protease inhibitor in the steps of the incubation and purification. However, these methods have not been generally employed because such a mutant strain as employed in the former method is inadequate as a host in some cases, and the addition of enzyme inhibitors in the latter method causes an increase in the production cost or it is feared that the inhibitors might remain in the product. In these cases, moreover, it is impossible to use OmpT protease as an enzyme for cleaving fusion proteins.

If the cleavage could be avoided by converting amino acid sequences at a site which is not desired to be cleaved by OmpT protease or in the vicinity thereof of the site, OmpT protease might be used as a cleavage enzyme. Therefore it is expected that cleavage can be efficiently avoided while minimizing the conversion of the amino acid sequence, if the characteristics of the OmpT protease recognition/cleavage sequences are clarified. Accordingly, in one aspect of the invention an amino acid sequence that is cleavable by OmpT protease can be converted into an amino acid sequence that is not cleavable or less cleavable by OmpT protease by converting OmpT protease recognition/cleavage sequences on the amino acid sequence.

BRIEF DESCRIPTION OF THE DRAWINGS

FIG. 4 shows the whole amino acid sequence (SEQ ID NO: 5) of a fusion protein PR encoded by pG117S4HompRHPR, wherein the underlined part corresponds to the amino acid sequence of human glucagon-like peptide-1 (GLP-1[G]); the double-underlined part corresponds to arginine having been converted into another amino acid; and the arrow shows the cleavage site by OmpT protease. The numerical symbols show the amino acid numbers counting from the N-terminus. The protective protein (β-gal117S4H) derived from the N-terminal 117 amino acids of *E. coli* β-galactosidase comprises the amino acid sequence from methionine at the 1-position to arginine at the 127-position. The linker peptide comprises the amino acid sequence from glutamine at the 128-position to arginine at the 153-position. Pre-GLP-1[G] comprises an amino acid sequence from arginine at the +1-position (concerning the cleavage site by OmpT protease) to glycine at the 184-position.

The nucleotide sequence from the transcription initiation site to the codon of the fifth amino acid following the OmpT protease translation initiation is 5'AATTGTGAGCG-GATAACAATTTCACACAGGAA <u>GAATTC</u>ATGCGGGCGAAACTT 3' (SEQ ID NO:65) wherein the underlined part corresponds to the EcoRI recognition site.

With respect to pGP501, see K. Sugimura, Biochem. Biophys. Res. Commun. 153: 753-759, 1988.

Figure 8:
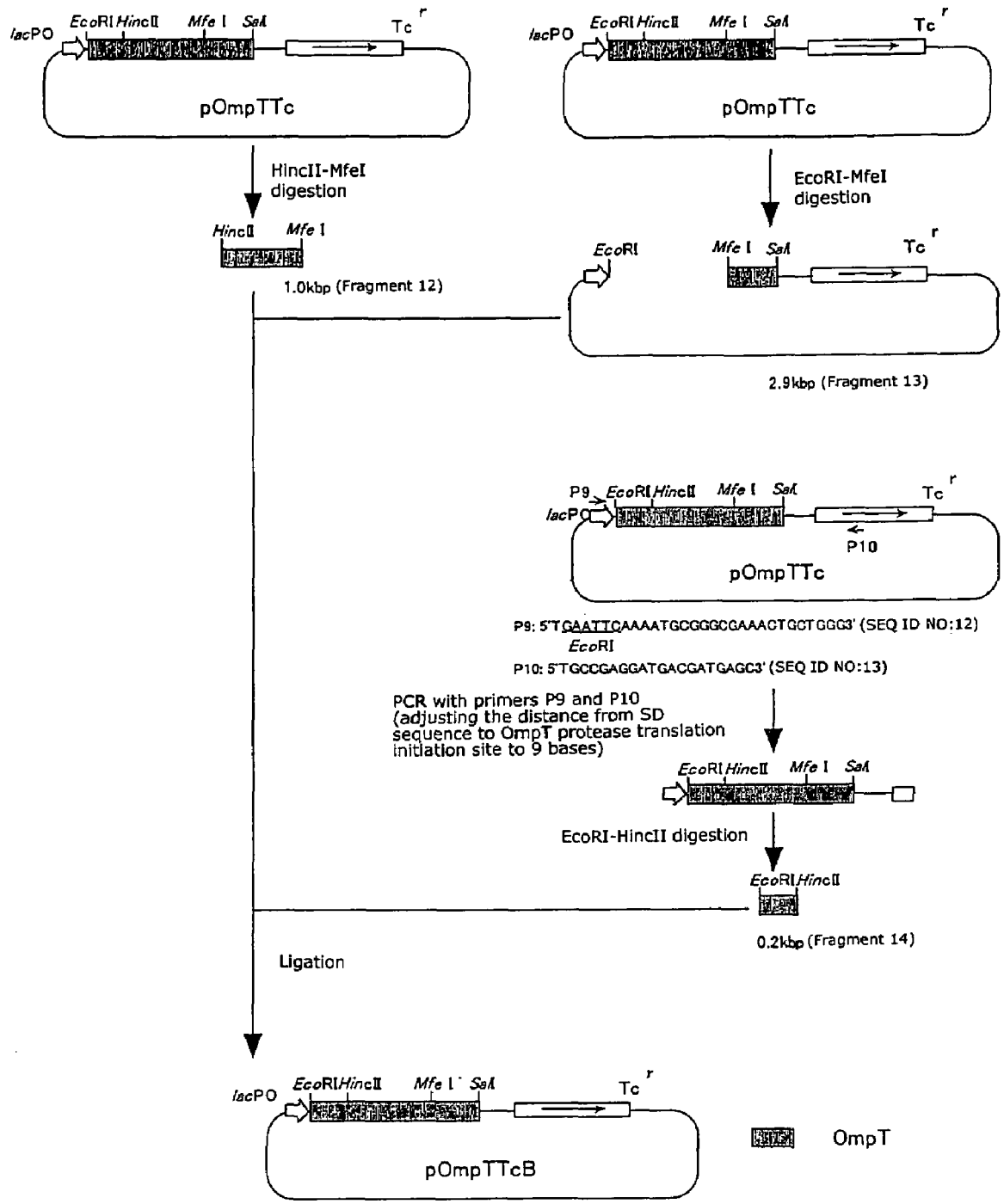

FIG. 8 is a diagrammatic illustration of the construction of pOmpTTcB, wherein OmpT represents OmpT protease gene; Tc^r represents a tetracycline-resistance gene; and lac PO represents *E. coli* lactose promoter operator gene.

The nucleotide sequence from the transcription initiation site to the codon of the fifth amino acid following the OmpT protease translation initiation is 5'AATTGTGAGCG-GATAACAATTTCACACAGGAA <u>GAATTC</u>AAAATGCGGGCGAAA CTG3' (SEQ ID NO:66) wherein the underlined part corresponds to the EcoRI recognition site.

Figure 9:
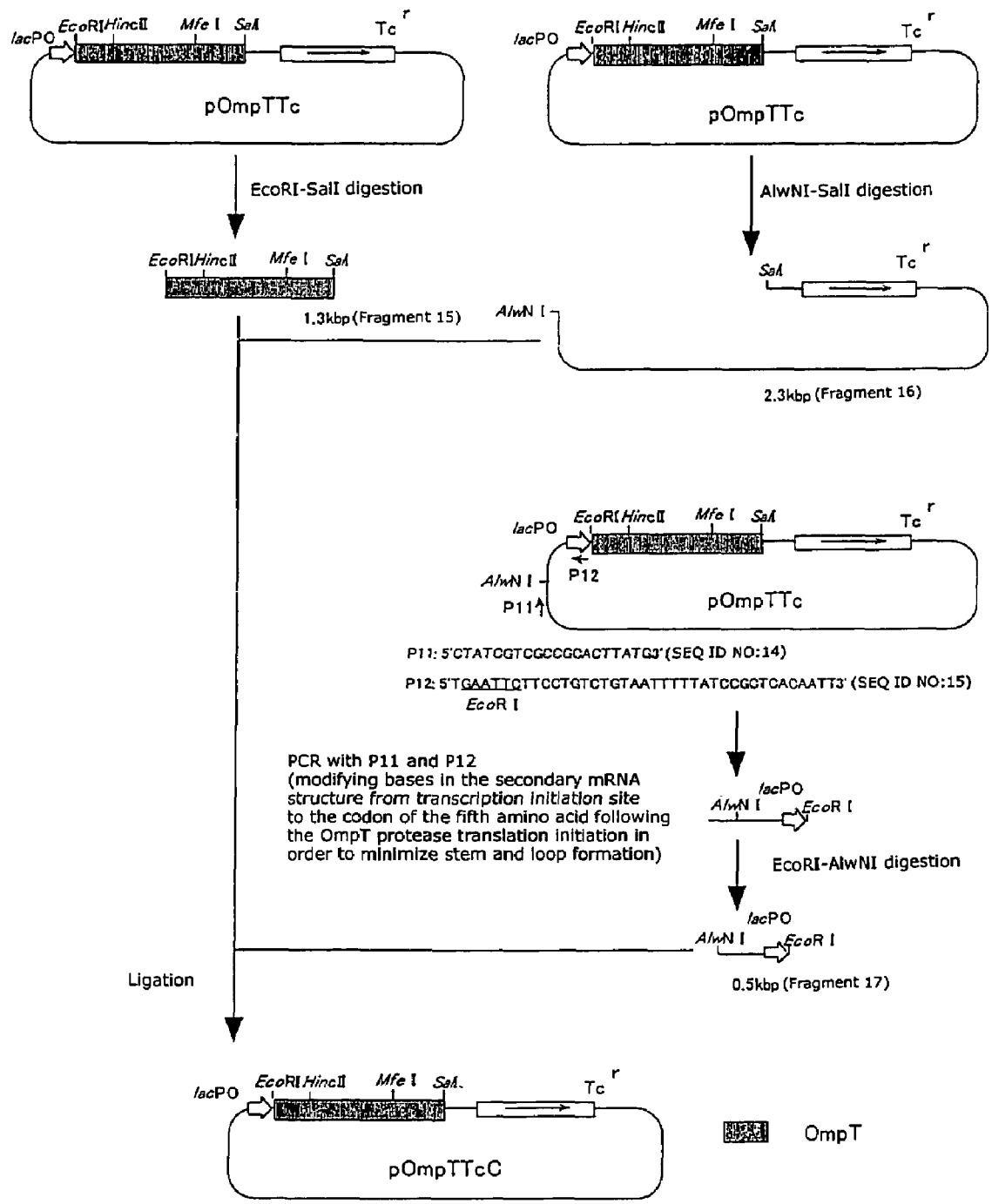

FIG. 9 is a diagrammatic illustration of the construction of pOmpTTcC, wherein OmpT represents OmpT protease gene; Tc^r represents a tetracycline-resistance gene; and lac PO represents *E. coli* lactose promoter operator gene.

The nucleotide sequence from the transcription initiation site to the codon of the fifth amino acid following the OmpT protease translation initiation is 5'AATTGTGAGCG-GATAAAAATTACAGACAGGAA <u>GAATTC</u>ATGCGGGCGAAACTT 3' (SEQ ID NO:67) wherein the underlined part corresponds to the EcoRI recognition site.

Figure 10:
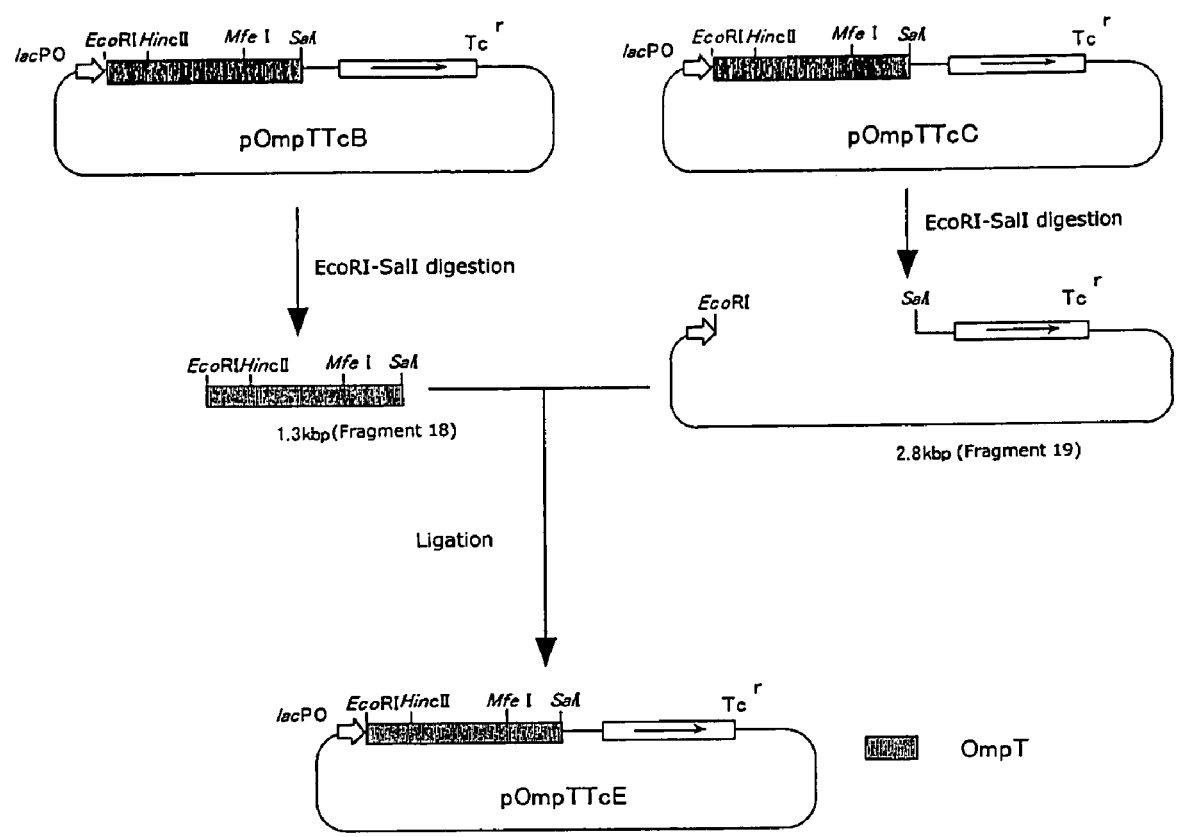

FIG. 10 is a diagrammatic illustration of the construction of pOmpTTcE, wherein OmpT represents OmpT protease gene; Tc^r represents a tetracycline-resistance gene; and lac PO represents *E. coli* lactose promoter operator gene.

The nucleotide sequence from the transcription initiation site to the codon of the fifth amino acid following the OmpT protease translation initiation is 5'AATTGTGAGCG-GATAAAAATTACAGACAGGAA <u>GAATTC</u>AAAATGCGGGCGAAA CTG3' (SEQ ID NO:68) wherein the underlined part corresponds to the EcoRI recognition site.

Figure 11:
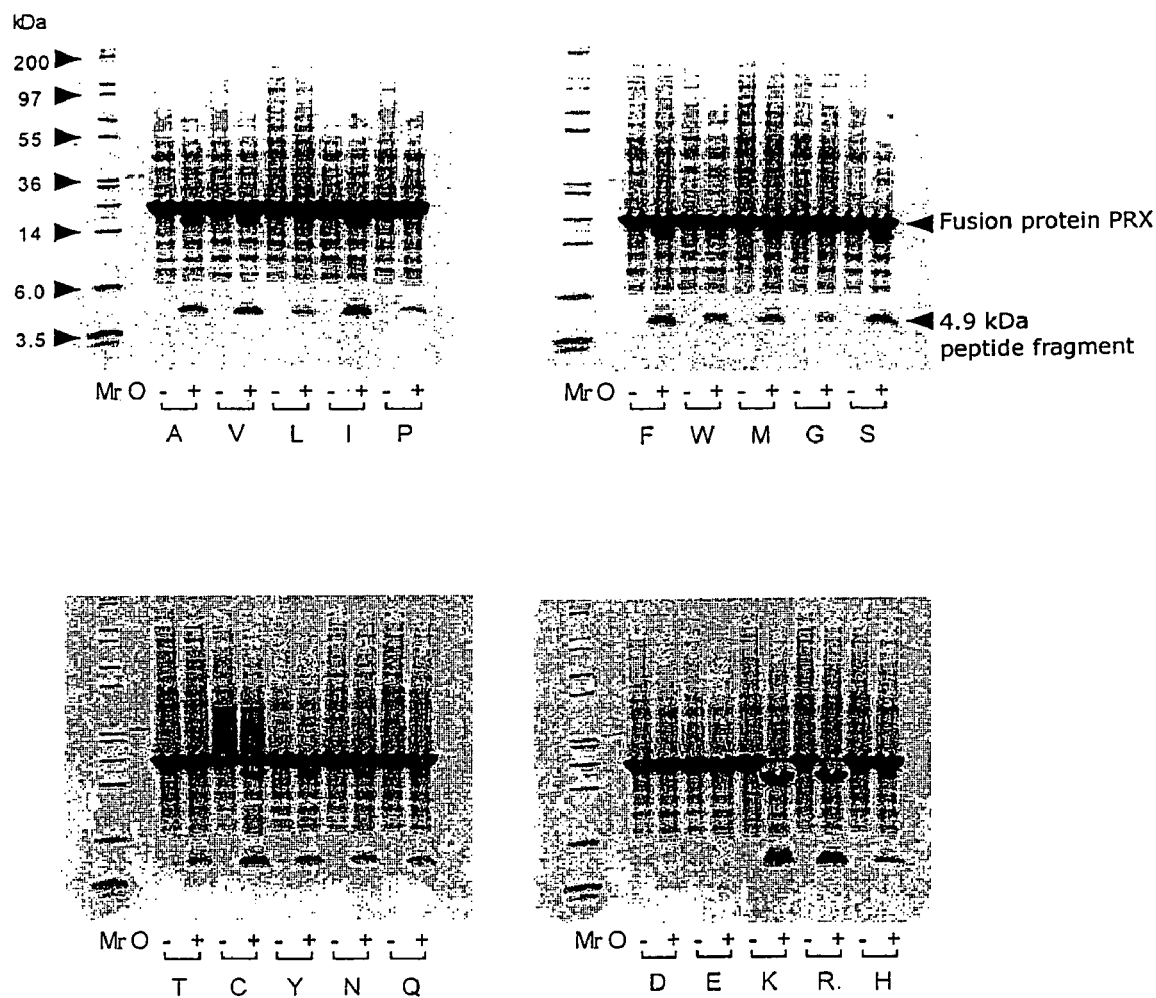

FIG. 11 is an SDS-PAGE (16%) photograph relating to the cleavage of the fusion protein PRX by OmpT protease.

In this figure, Mr represents molecular weight marker proteins; O represents the lane for purified OmpT protease; − represents a lane free from OmpT protease; and +represents a lane with the addition of OmpT protease.

A: PRA, V: PRV, L: PRL, I: PRI, P: PRP, F: PRF, W: PRW, M: PRM, G: PRG, S: PRS, T: PRT, C: PRC, Y: PRY, N: PRN, Q: PRQ, D: PRD, E: PRE, K: PRK, R: PRR, H: PRH.

The 4.9 kDa peptide fragment means a peptide fragment containing GLP-1[G] which has been excised by OmpT protease.

Figure 12:
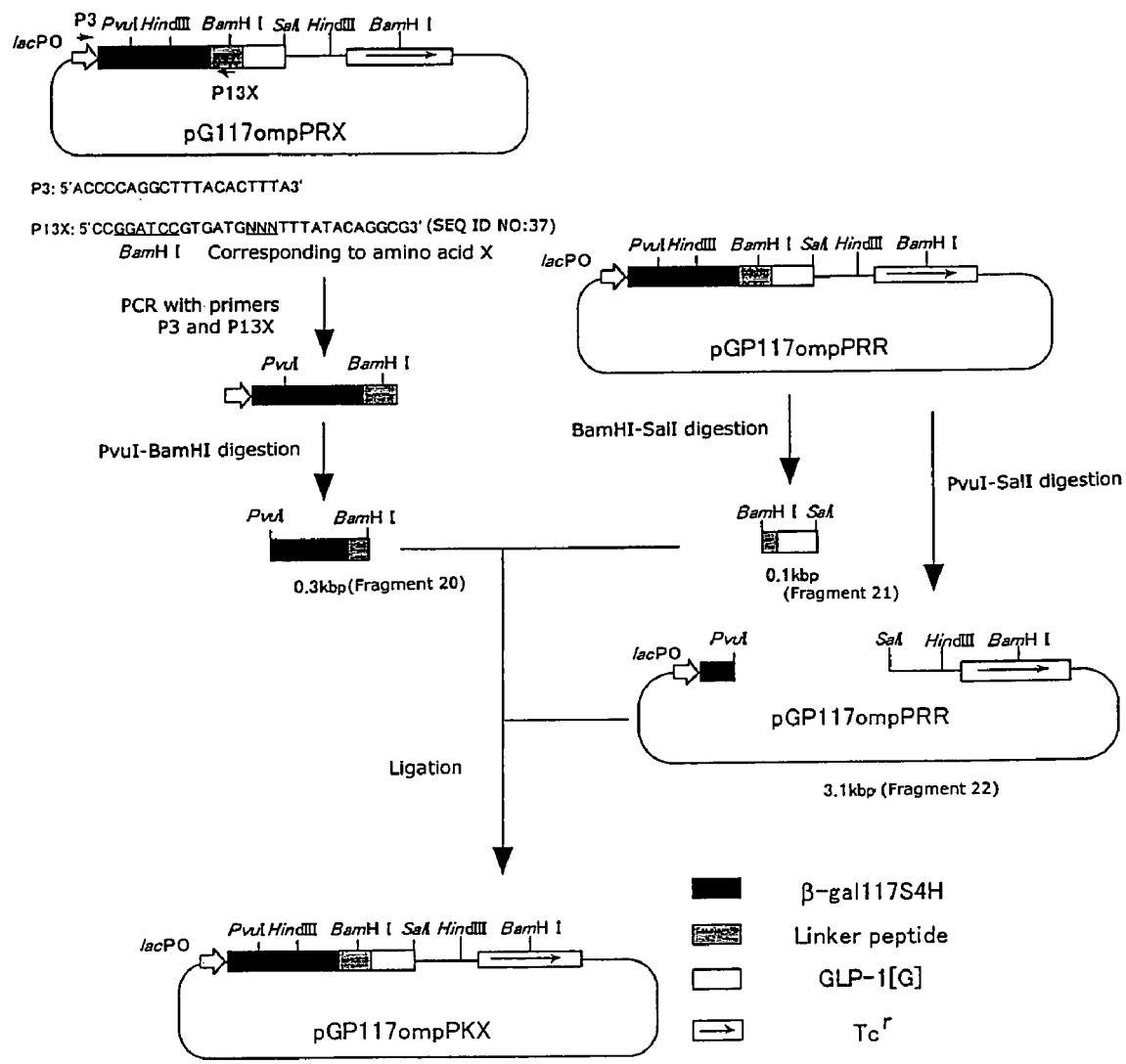

FIG. 12 is a diagrammatic illustration of the construction of pG117ompPKX, wherein β-gal117S4H represents a region encoding a protective protein derived from the N-terminal 117 amino acids of *E. coli* β-galactosidase; GLP-1[G] represents a region encoding human glucagon-like peptide-1; Tc^r represents a tetracycline-resistance gene; Linker peptide represents a region encoding an amino acid sequence from glutamine at the 128-position to arginine at the 153-position; and lac PO represents *E. coli* lactose promoter operator gene. P3 is SEQ ID NO: 6.

Figure 13:
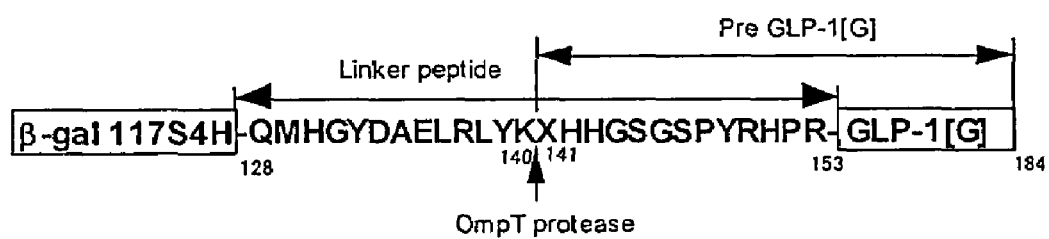

FIG. 13 is a diagrammatic illustration showing the structure of a fusion protein PKX encoded by pG117ompPKX, wherein numerical symbols show the amino acid numbers counting from the N-terminus of the fusion protein PKX. β-gal117S4H represents a protective protein derived from the N-terminal 117 amino acids of *E. coli* β-galactosidase; GLP-1[G] represents a human glucagon-like peptide-1; Pre GLP-1[G] represents a target peptide comprising an amino acid sequence from the 141- to 184-positions (SEQ ID NO: 128) containing GLP-1[G]; and Linker peptide represents the amino acid sequence from glutamine at the 128-position to arginine at the 153-position. A site (lysine 140-X141) corresponding to the OmpT protease cleavage site in the fusion protein PRR is shown in this figure.

Figure 14:
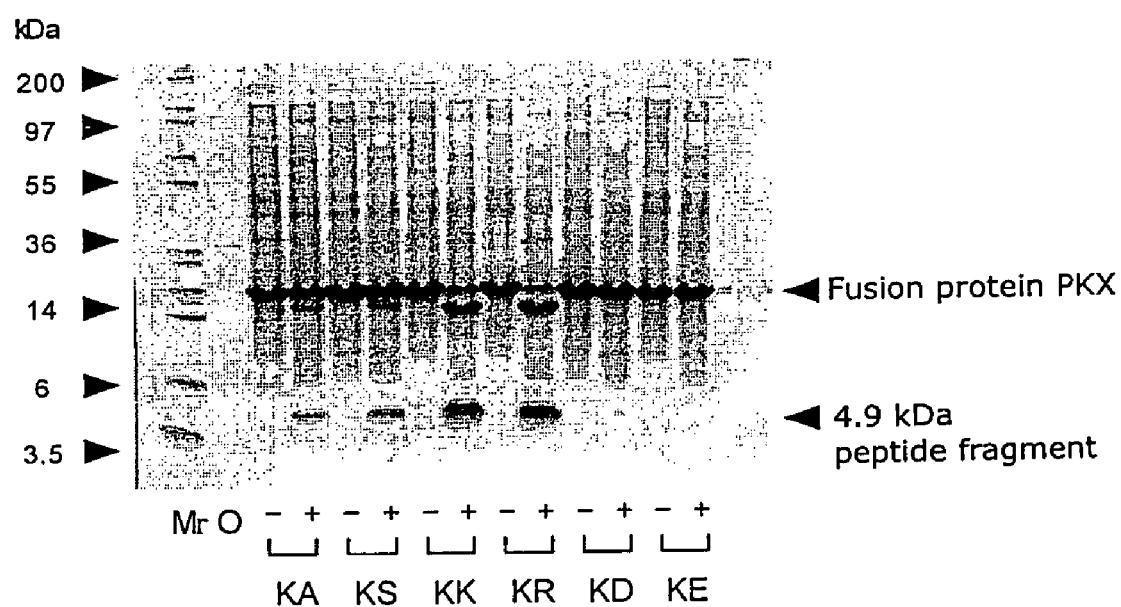

FIG. 14 is an SDS-PAGE (16%) photograph relating to the cleavage of the fusion protein PKX by OmpT protease. In this figure, Mr represents molecular weight marker proteins; O represents purified OmpT protease; – represents a lane free from OmpT protease; and + represents a lane with the addition of OmpT protease.

KA, KS, KK, KR, KD and KE represent respectively PKA, PKS, PKK, PKR, PKD and PKE.

The 4.9 kDa peptide fragment means a peptide fragment containing GLP-1[G] which has been excised by OmpT protease.

Figure 15:
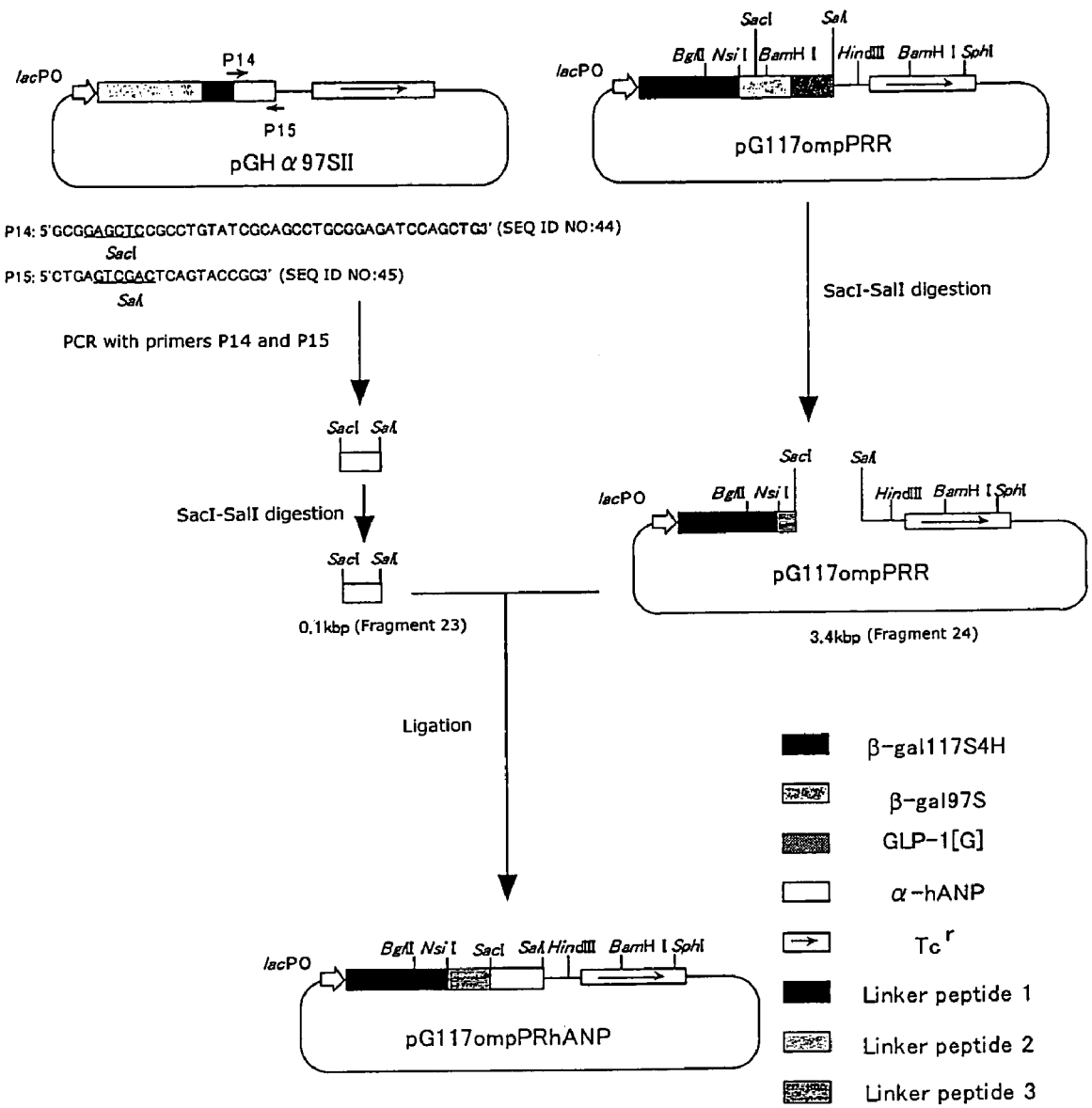

FIG. 15 is a diagrammatic illustration of the construction of pG117ompPRhANP, wherein β-gal117S4H represents a region encoding a protective protein derived from the N-terminal 117 amino acids of *E. coli* β-galactosidase; GLP-1[G] represents a region encoding human glucagon-like peptide-1; α-hANP represents a region encoding α-type human atrial natriuretic peptide; Tc^r represents a tetracycline-resistance gene; Linker peptide 1 represents a region encoding an amino acid sequence QFK (SEQ ID NO:69); linker peptide 2 represents a region encoding an amino acid sequence QMHGYDAELRLYRRHHGSGSPYRHPR (SEQ ID NO:70); Linker peptide 3 represents a region encoding an amino acid sequence QMHGYDAELRLYR (SEQ ID NO:71); and lac PO represents *E. coli* lactose promoter operator gene. With respect to pGH α97SII, see "Daichokin o shukushu toshita seirikassei peputido seisankei ni kansuru kenkyu (Study on Physiologically Active Peptide Production System with the Use of *E. coli* as Host)", Koji Magota, Doctoral Dissertation, Kyushu University, 1991.

Figure 16:
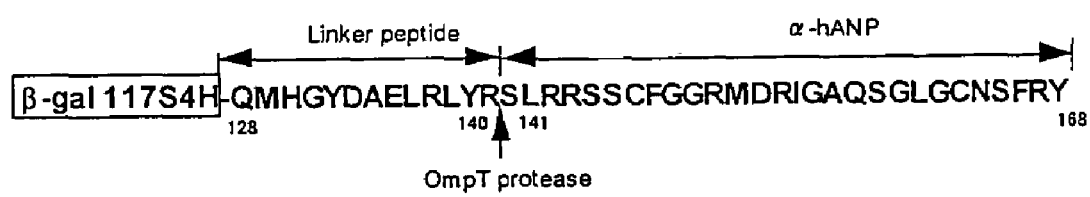

FIG. 16 is a diagrammatic illustration showing the structure of a fusion protein PRhANP encoded by pG117ompPRhANP, wherein numerical symbols show the amino acid numbers counting from the N-terminus of the fusion protein PRhANP (SEQ ID NO: 129). β-gal117S4H represents a protective protein derived from the N-terminal 117 amino acids of *E. coli* β-galactosidase; α-hANP represents an α-human atrial natriuretic peptide; and Linker peptide represents the amino acid sequence from glutamine at the 128-position to arginine at the 140-position. A site (arginine 140-serine 141) corresponding to the OmpT protease cleavage site in the fusion protein PRR is shown in this figure.

Figure 17:
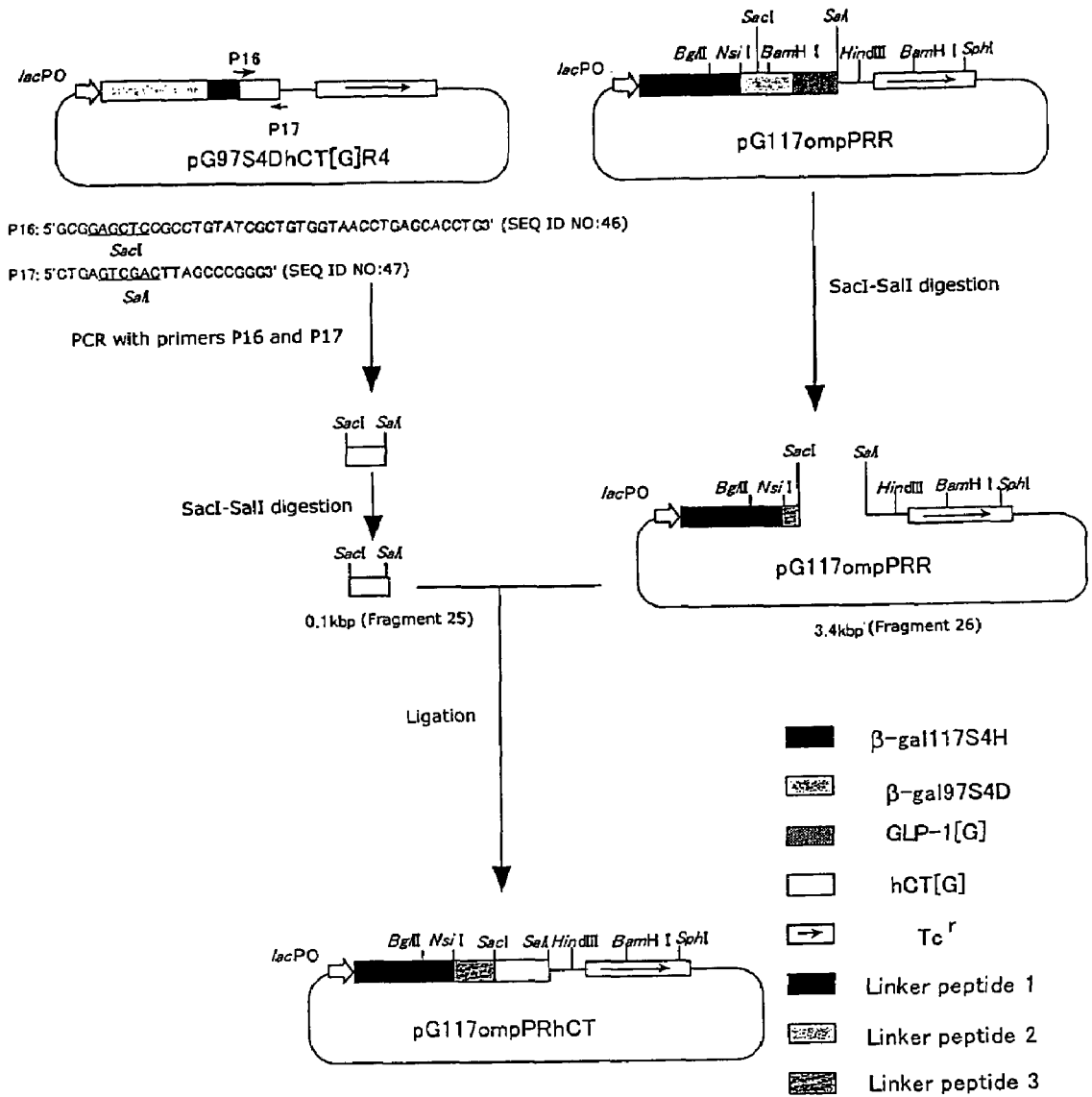

FIG. 17 is a diagrammatic illustration of the construction of pG117ompPRhCT, wherein β-gal117S4H represents a region encoding a protective protein derived from the N-terminal 117 amino acids of *E. coli* β-galactosidase; β-gal 197S4D represents a region encoding a protective protein originating in 97 amino acids from the N-terminus of *E. coli* β-galactosidase; GLP-1[G] represents a region encoding human glucagon-like peptide-1; Tc^r represents a tetracycline-resistance gene; Linker peptide 1 represents a region encoding an amino acid sequence EFRHHRRHRLE (SEQ ID NO:72); Linker peptide 2 represents a region encoding an amino acid sequence QMHGYDAELRLYRRHHGSG-SPYRHPR (SEQ ID NO: 70); Linker peptide 3 represents a region encoding an amino acid sequence QMHGYDAEL-RLYR (SEQ ID NO: 71); and lac PO represents *E. coli* lactose promoter operator gene. With respect to pG97S4DhCT[G]R4, see Yabuta, M., Suzuki, Y. and Ohsuye, K. Appl. Microbiol. Biotechnol. 42: 703-708, 1995.

Figure 18:

FIG. 18 is a diagrammatic illustration showing the structure of the fusion protein PRhCT encoded by pG117ompPRhCT, wherein numerical symbols show the amino acid numbers counting from the N-terminus of the fusion protein PRhCT. β-gal117S4H represents a protective protein derived from the N-terminal 117 amino acids of *E. coli* β-galactosidase; hCT[G] represents a human calcitonin precursor; and Linker peptide represents the amino acid sequence from glutamine at the 128-position to arginine at the 140-position (SEQ ID NO: 130). A site (arginine 140-cysteine 141) corresponding to the OmpT protease cleavage site in the fusion protein PRR is shown in this figure.

Figure 19:
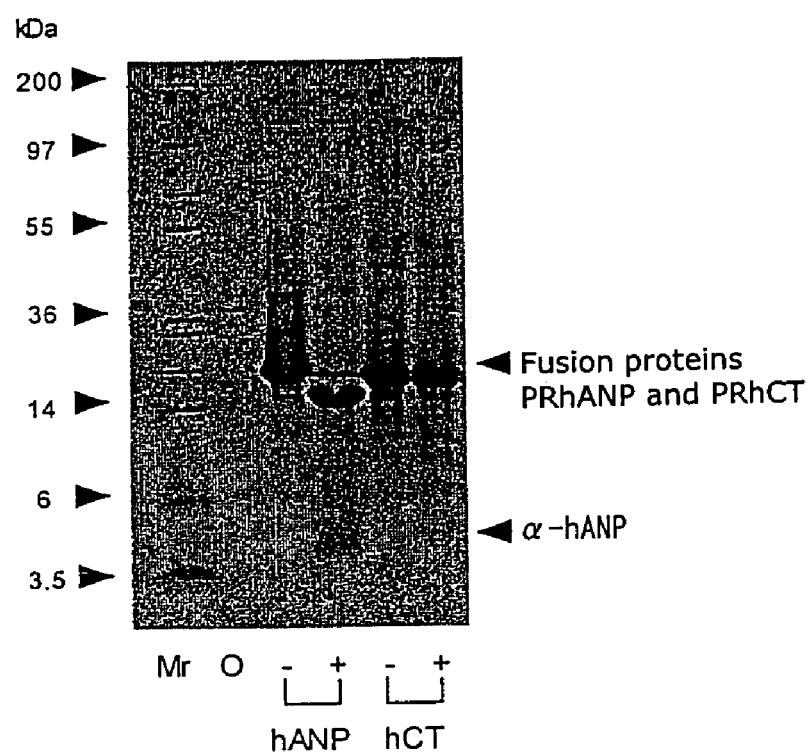

FIG. 19 is an SDS-PAGE (16%) photograph relating to the cleavage of the fusion proteins PRhANP and PRhCT by OmpT protease. In this figure, Mr represents molecular weight marker proteins; O represents purified OmpT protease; – represents a lane free from OmpT protease; and + represents a lane with the addition of OmpT protease.

hANP and hCT represent respectively PRhANP and PRhCT.

Figure 20:
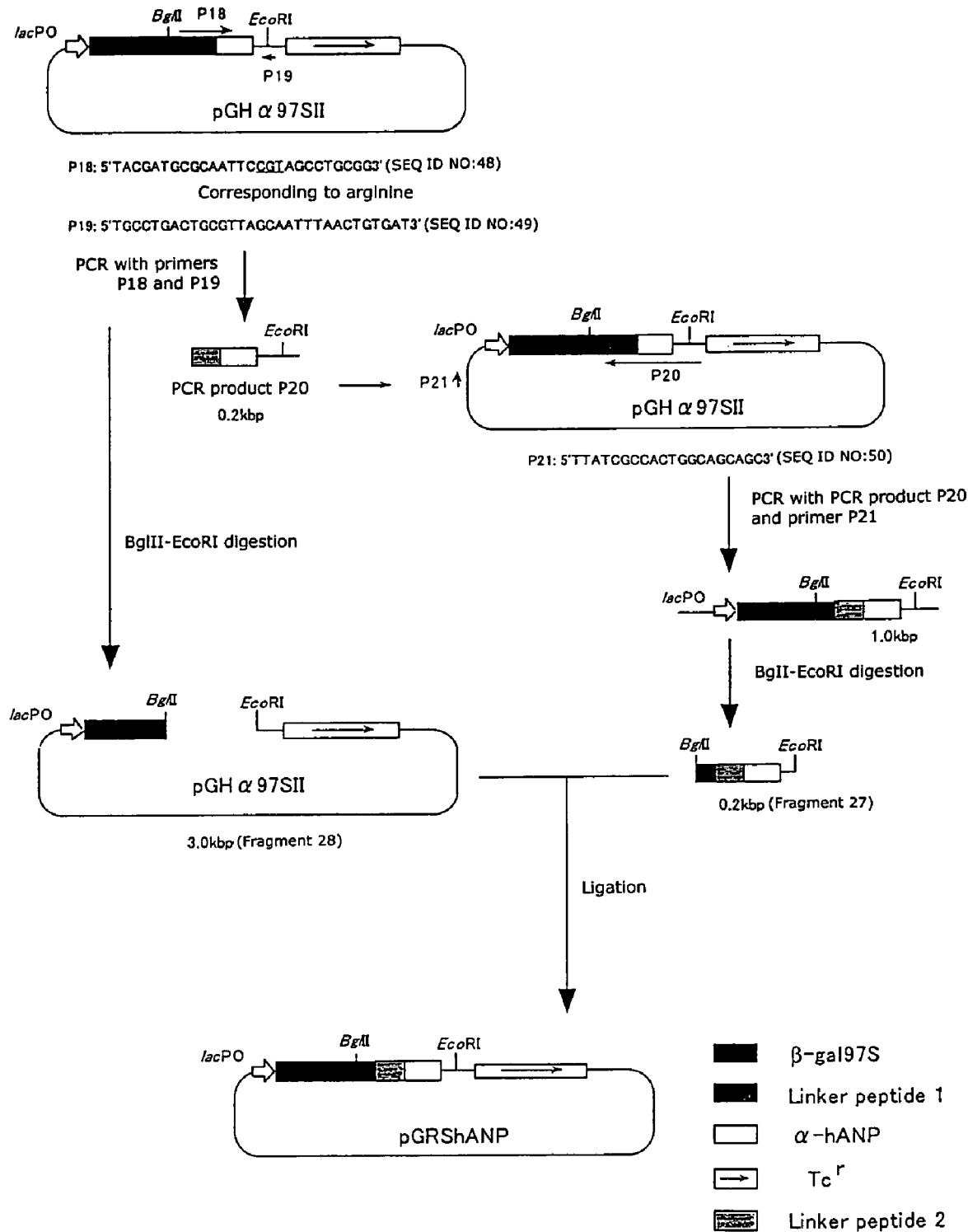

FIG. 20 is a diagrammatic illustration of the construction of pGRShANP, wherein β-gal97S represents a region encoding a protective protein derived from the N-terminal 97 amino acids of *E. coli* β-galactosidase; α-hANP represents a region encoding α-type human atrial natriuretic peptide; Tc^r represents a tetracycline-resistance gene; Linker peptide 1 represents a region encoding an amino acid sequence QFK; Linker peptide 2 represents a region encoding an amino acid sequence QFR (SEQ ID NO:73); and lac PO represents *E. coli* lactose promoter operator gene.

FIG. 21 is a diagrammatic illustration showing the whole amino acid sequence of a fusion protein RShANP encoded by pGRShANP wherein the underlined part represents the amino acid sequence of α-hANP (α-type human atrial natriuretic peptide); the double-underlined part represents serine having been converted into another amino acid; and the arrow shows the cleavage site by OmpT protease (SEQ ID NO: 131). The numerical symbols show the amino acid numbers counting from the N-terminus. The protective protein (β-gal97S) derived from the N-terminal 97 amino acids of *E. coli* β-galactosidase comprises the amino acid sequence from methionine at the 1-position to alanine at the 98-position. The linker peptide comprises the amino acid sequence from glutamine at the 99-position to arginine at the 101-position.

Figure 22:
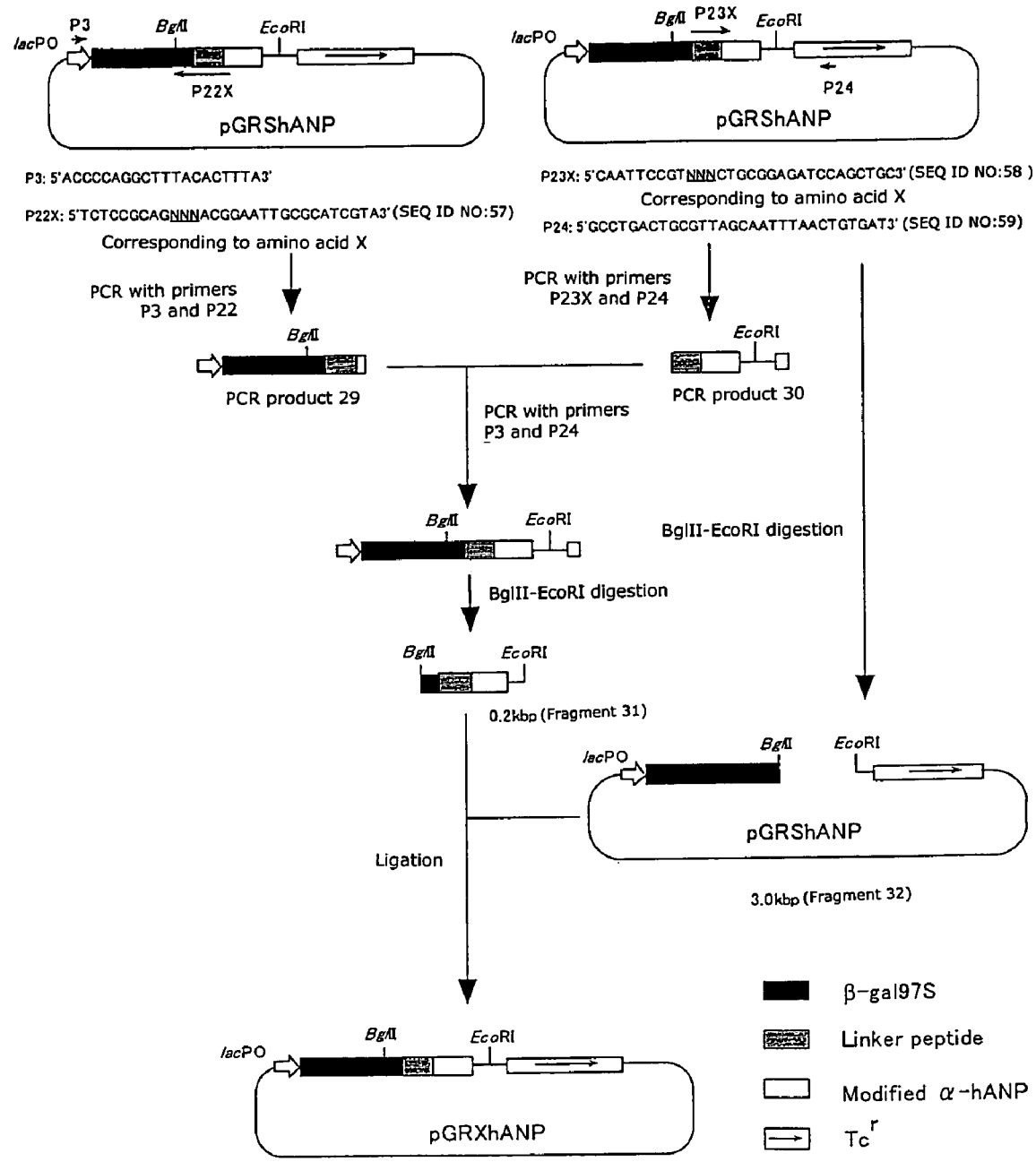

FIG. 22 is a diagrammatic illustration of the construction of pGRXhANP, wherein β-gal97S represents a region encoding a protective protein derived from the N-terminal 97 amino acids of *E. coli* β-galactosidase; Modified α-hANP represents a region encoding an α-type human atrial natriuretic peptide derivative having substitution of the N-terminal amino acid into arginine, alanine or cysteine; Tc$^r$ represents a tetracycline-resistance gene; Linker peptide represents a region encoding an amino acid sequence QFK; and lac PO represents *E. coli* lactose promoter operator gene. P3 is SEQ ID NO: 6.

Figure 23:
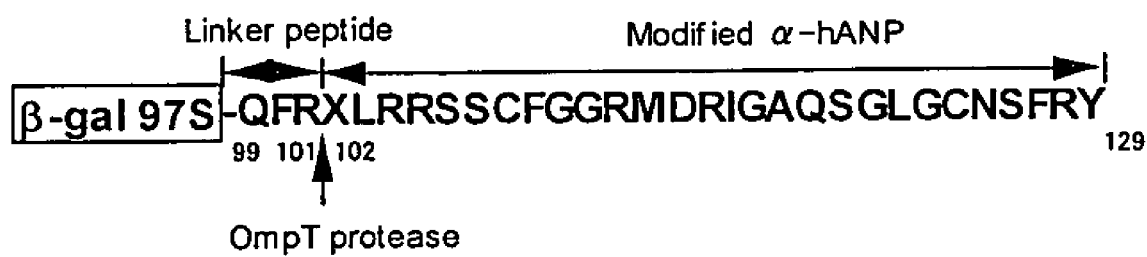

FIG. 23 is a diagrammatic illustration showing the structure of a fusion protein RXhANP, wherein numerical symbols show the amino acid numbers counting from the N-terminus of the fusion protein PRhANP (SEQ ID NO: 132). β-gal97S represents a protective protein derived from the N-terminal 97 amino acids of *E. coli* β-galactosidase; Modified α-hANP represents an α-type human atrial natriuretic peptide derivative having a substitution of the N-terminal amino acid into arginine, alanine or cysteine; and Linker peptide represents the amino acid sequence from glutamine at the 99-position to arginine at the 101-position. A site (arginine 101-X102) corresponding to the OmpT protease cleavage site in the fusion protein RShANP is shown in this figure.

Figure 24:
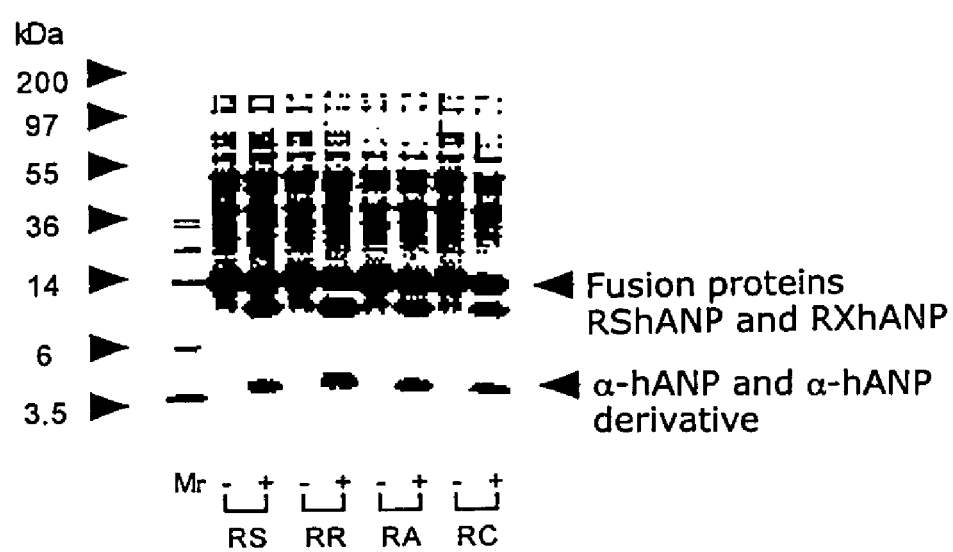

FIG. 24 is an SDS-PAGE (16%) photograph relating to the cleavage of the fusion proteins RShANP and RXhANP by OmpT protease.

In this figure, Mr represents molecular weight marker proteins; – represents a lane free from OmpT protease; and + represents a lane with the addition of OmpT protease. RS, RR, RA and RC respectively represent RShANP, RRhANP, RAhANP and RChANP.

Figure 25:
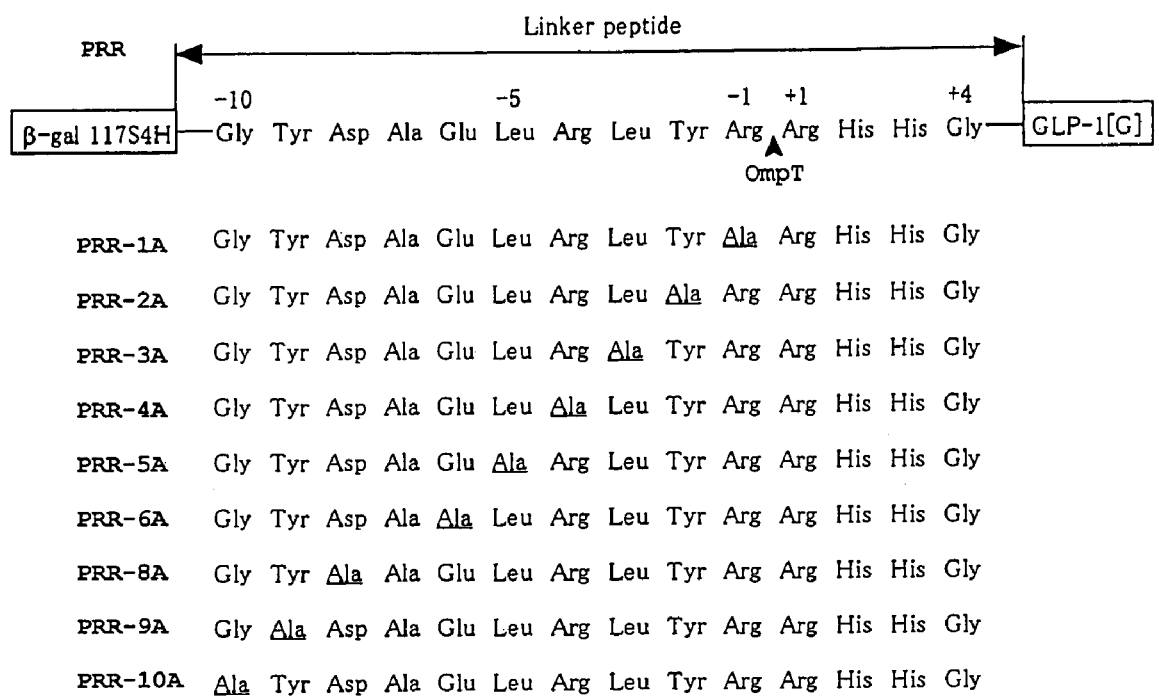

FIG. 25 is a diagrammatic illustration showing the structure of a fusion protein PRRXA encoded by pG117ompPRRXA, wherein –10, –5, –1, +1 and +4 respectively show the –10, –5, –1, +1 and +4-positions concerning the OmpT protease cleavage site of the fusion protein PRR. The amino acid sequence (from –10- to +4-positions) of the fusion proteins PRR and PRRXA are given in the figure. β-gal117S4H represents a protective protein originating in the N-terminal 117 amino acids of *E. coli* β-galactosidase; GLP-1-[G] represents a human glucagon-like peptide-1; and Linker peptide corresponds to the amino acid sequence from glutamine at the 128-position to arginine at the 153-position in the amino acid sequence shown in FIG. 6. The OmpT protease cleavage site in the fusion protein PRR is shown in this figure. The fusion proteins are represented in bold figures and the substituted alanine is underlined. The linker peptide is SEQ ID NO: 101; PRR-1A is SEQ ID NO: 102; PRR-2A is SEQ ID NO: 103; PRR-3A is SEQ ID NO: 104; PRR-4A is SEQ ID NO: 105; PRR-5A is SEQ ID NO: 106; PRR-6A is SEQ ID NO: 107; PRR-8A is SEQ ID NO: 108; PRR-9A is SEQ ID NO: 109; and PRR-10A is SEQ ID NO: 110.

Figure 26:
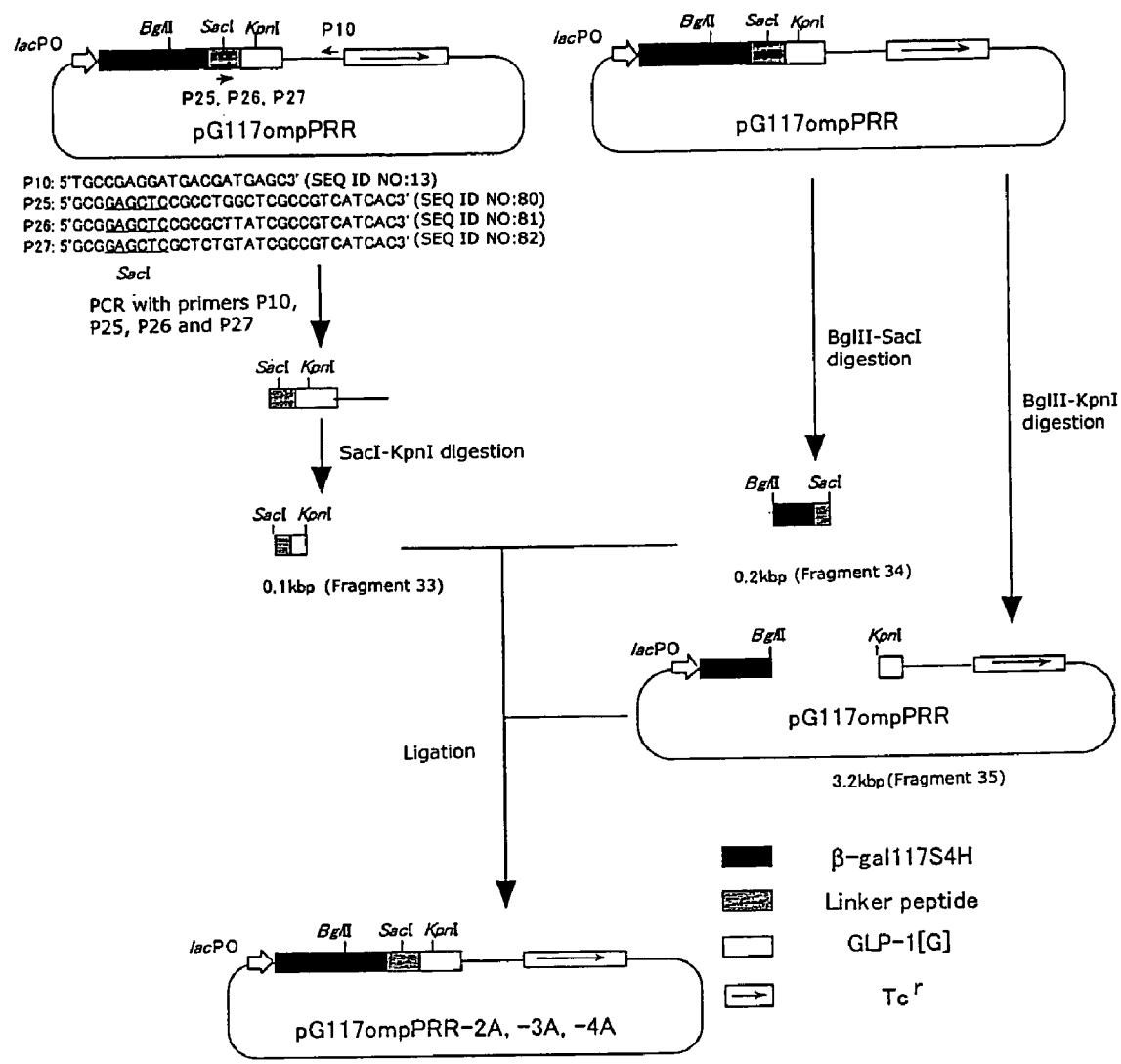

FIG. 26 is a diagrammatic illustration of the construction of pG117ompPRR-2A, -3A and -4A. β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding an amino acid sequence from glutamine at the 128-position to arginine at the 153-position in the amino acid sequence shown in FIG. 6; and lac PO represents *E. coli* lactose promoter operator gene.

Figure 27:
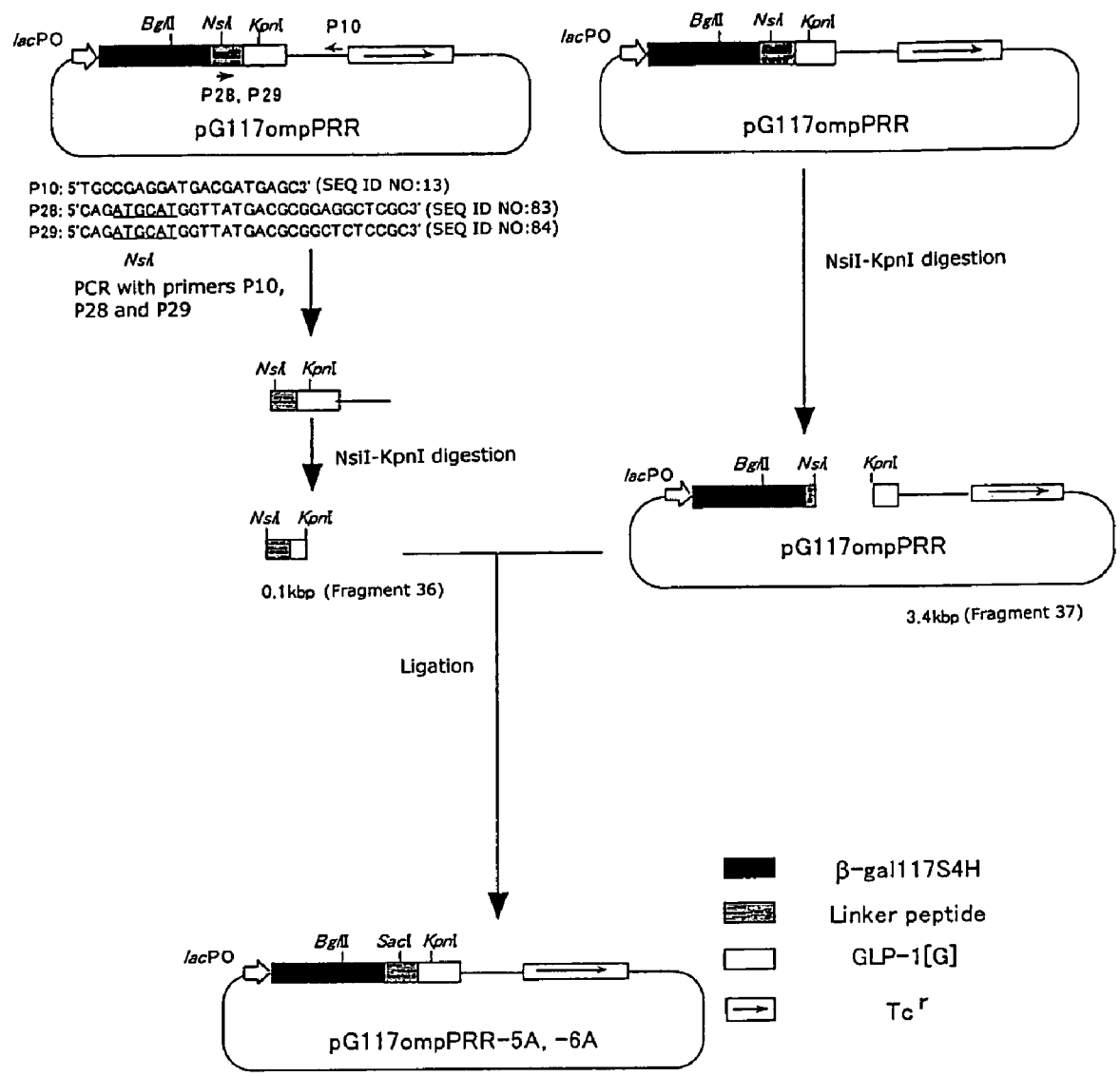

FIG. 27 is a diagrammatic illustration of the construction of pG117ompPRR-5A and -6A, wherein β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding an amino acid sequence from glutamine at the 128-position to arginine at the 153-position in the amino acid sequence shown in FIG. 6; and lac PO represents *E. coli* lactose promoter operator gene.

Figure 28:
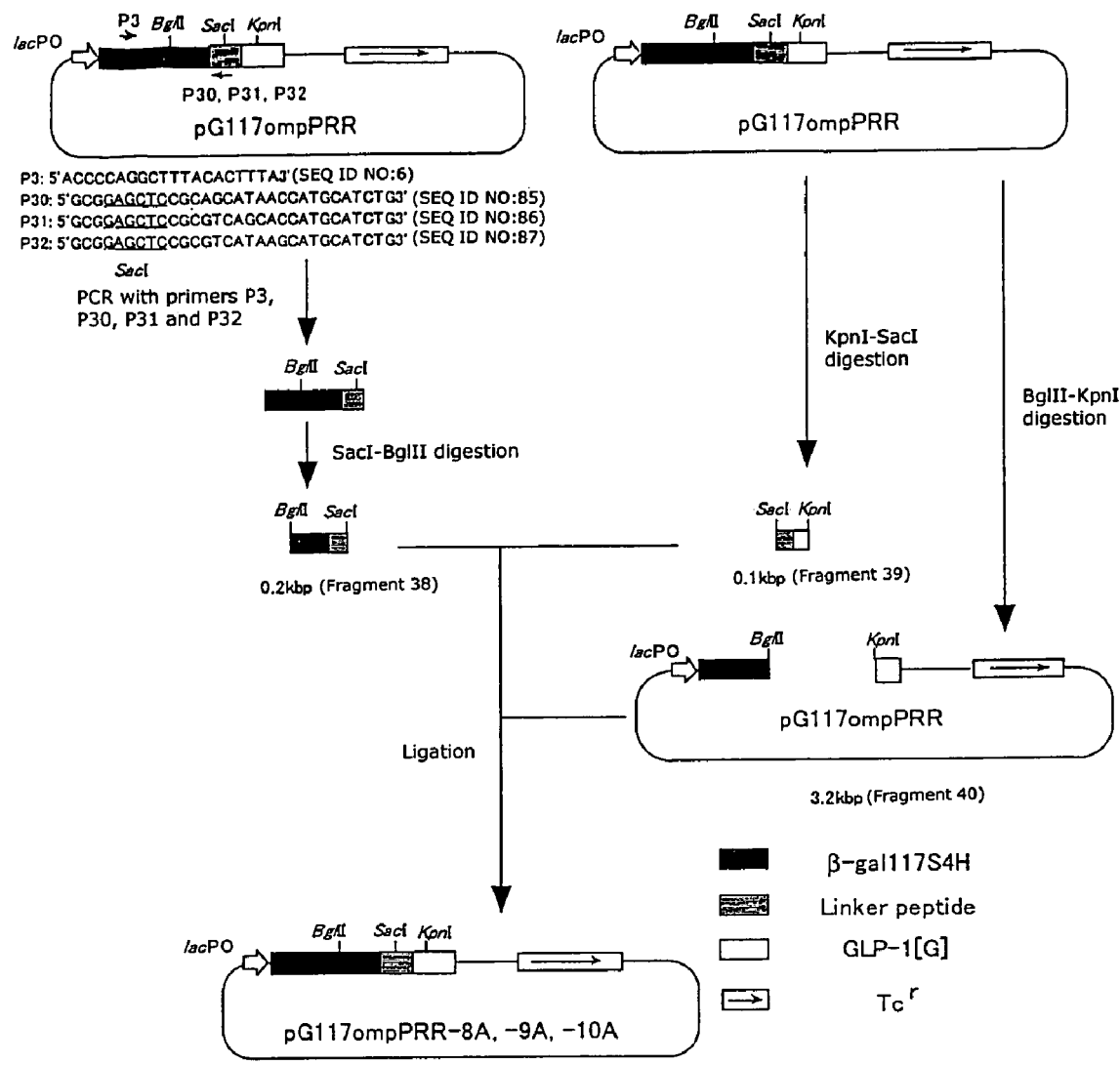

FIG. 28 is a diagrammatic illustration of the construction of pG117ompPRR-8A, -9A and -10A, wherein β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding the amino acid sequence from glutamine at the 128-position to arginine at the 153-position in the amino acid sequence shown in FIG. 6; and lac PO represents *E. coli* lactose promoter operator gene.

Figure 29:
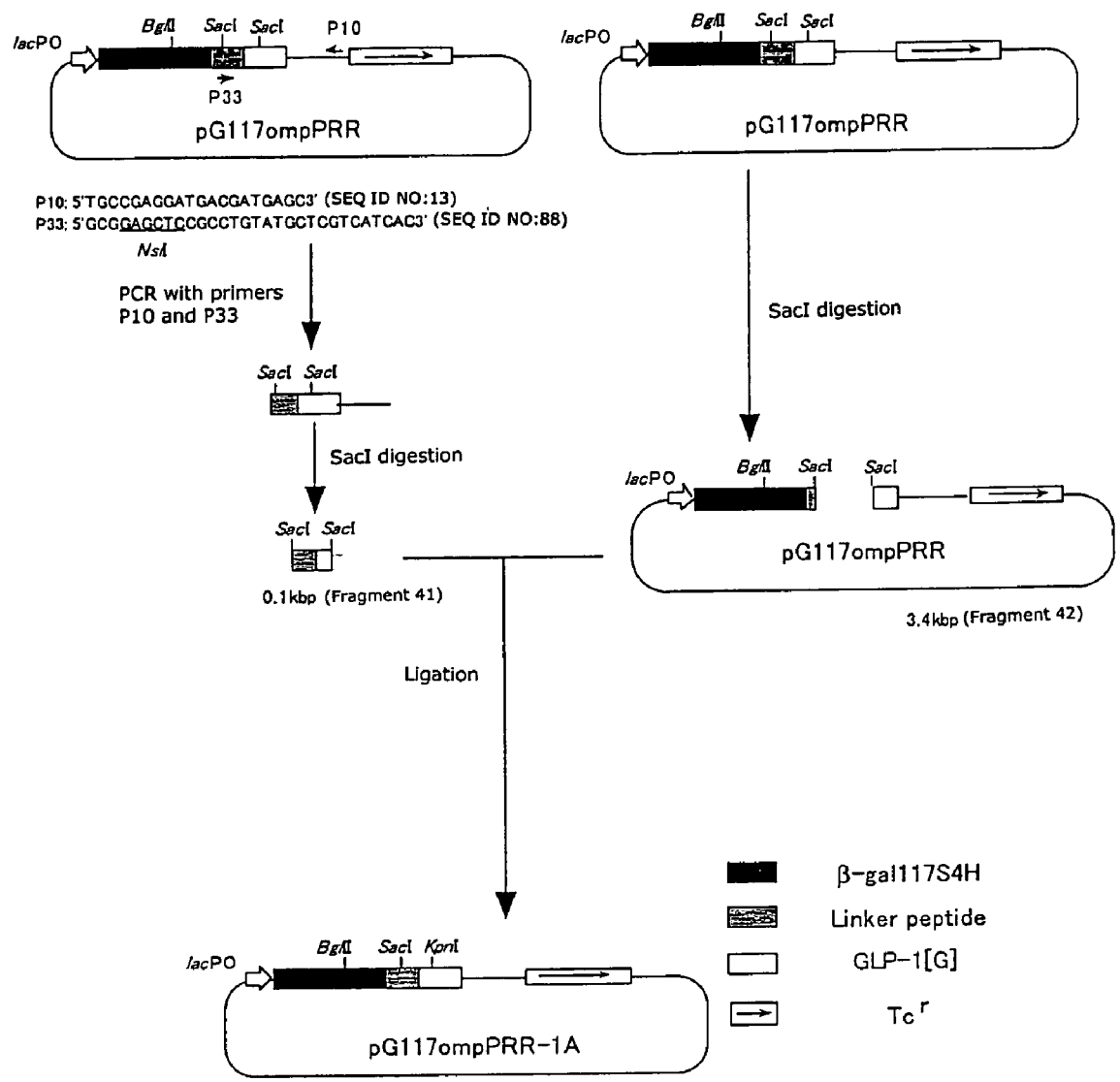

FIG. 29 is a diagrammatic illustration of the construction of pG117ompPRR-1A, wherein β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding the amino acid sequence from glutamine at the 128-position to arginine at the 153-position in the amino acid sequence shown in FIG. 6; and lac PO represents *E. coli* lactose promoter operator gene.

Figure 30:
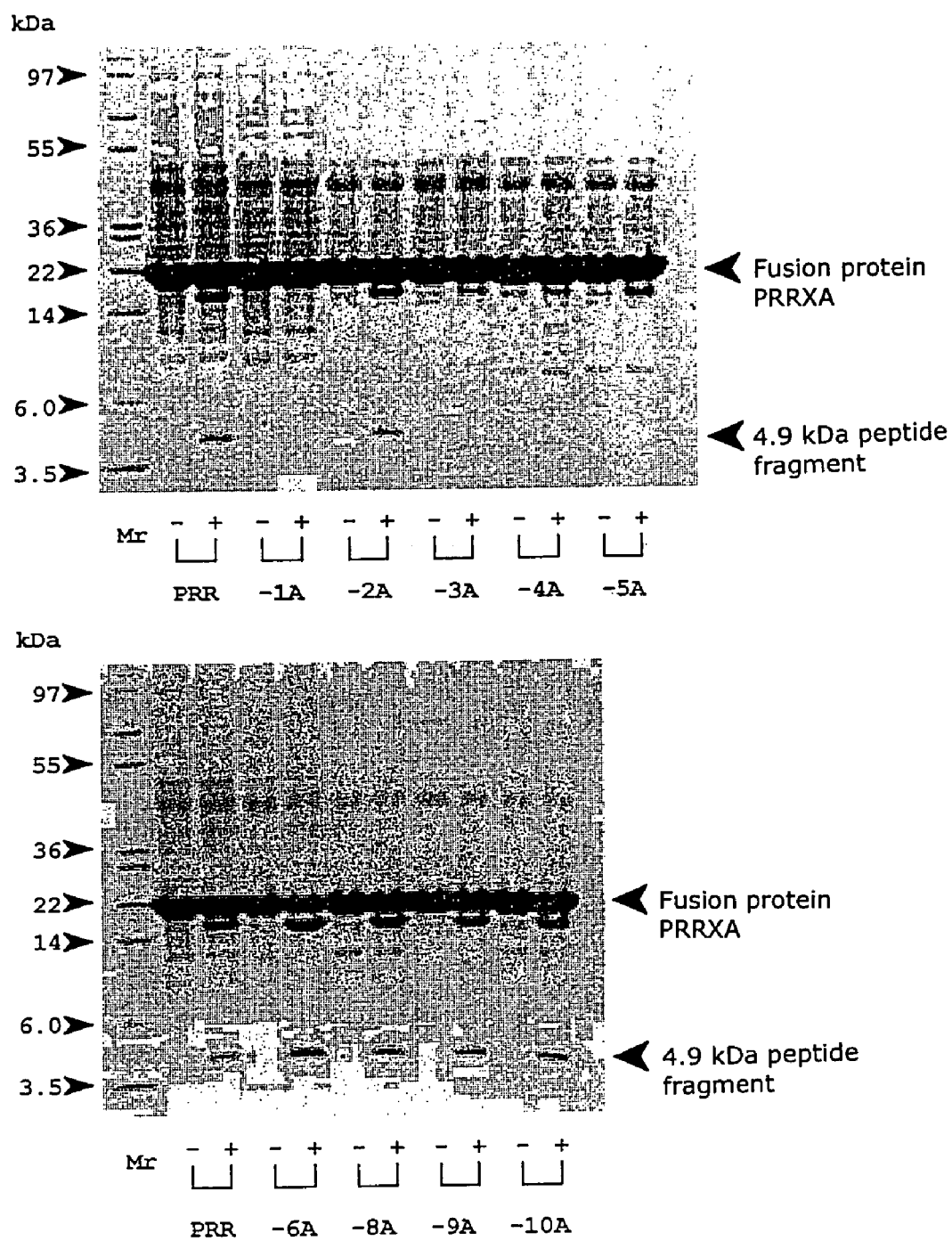

FIG. 30 is an SDS-PAGE (16%) photograph relating to the cleavage of the fusion proteins PRR and PRRXA by OmpT protease. In this figure, Mr represents a protein molecular weight marker; O represents purified OmpT protease; – represents a lane free from OmpT protease; and + represents a lane with the addition of OmpT protease.

-1A: PRR-1A, -2A: PRR-2A, -3A: PRR-3A, -4A: PRR-4A, –5A: PRR-5A -6A: PRR-6A, -8A: PRR-8A, -9A: PRR-9A, -10A: PRR-10A.

The 4.9 kDa peptide fragment means a peptide fragment containing GLP-1[G] which has been excised by OmpT protease.

Figure 31:
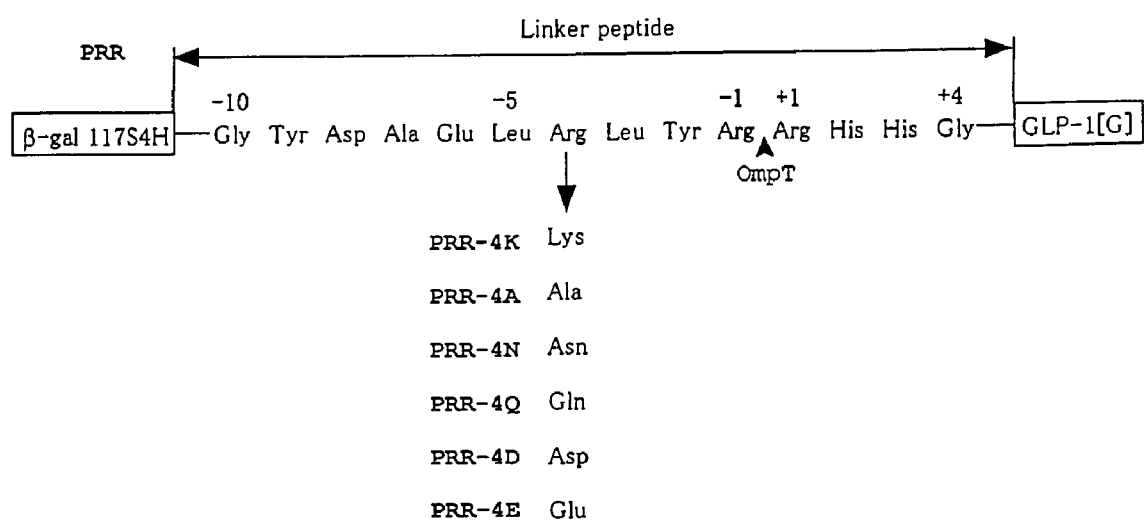

FIG. 31 is a diagrammatic illustration showing the structure of the fusion protein PRR-4X encoded by pG117ompPRR-4X, wherein –10, –5, –1, +1 and +4 respectively show the –10, –5, –1, +1 and +4-positions concerning the OmpT protease cleavage site of the fusion protein PRR. The amino acid sequence (from –10- to +4-positions) of the fusion proteins PRR and the substituted amino acid at the –4-position of the fusion protein PRR-4X are given in the figure. β-gal117S4H represents a protective protein derived from the N-terminal 117 amino acids of *E. coli* β-galactosidase; GLP-1[G] represents a human glucagon-like peptide-1; and Linker peptide (SEQ ID NO: 101) corresponds to an amino acid sequence from glutamine at the 128-position to arginine at the 153-position in the amino acid sequence shown in FIG. 6. The OmpT protease cleavage site in the fusion protein PRR is shown in this figure. The fusion proteins are expressed in bold figures. PRR-4K is SEQ ID NO: 111; PRR-4A is SEQ ID NO: 112; PRR-4N is SEQ ID NO: 113; PRR-4Q is SEQ ID NO: 114; PRR-4D is SEQ ID NO: 115; and PRR-4E is SEQ ID NO: 116.

Figure 32:
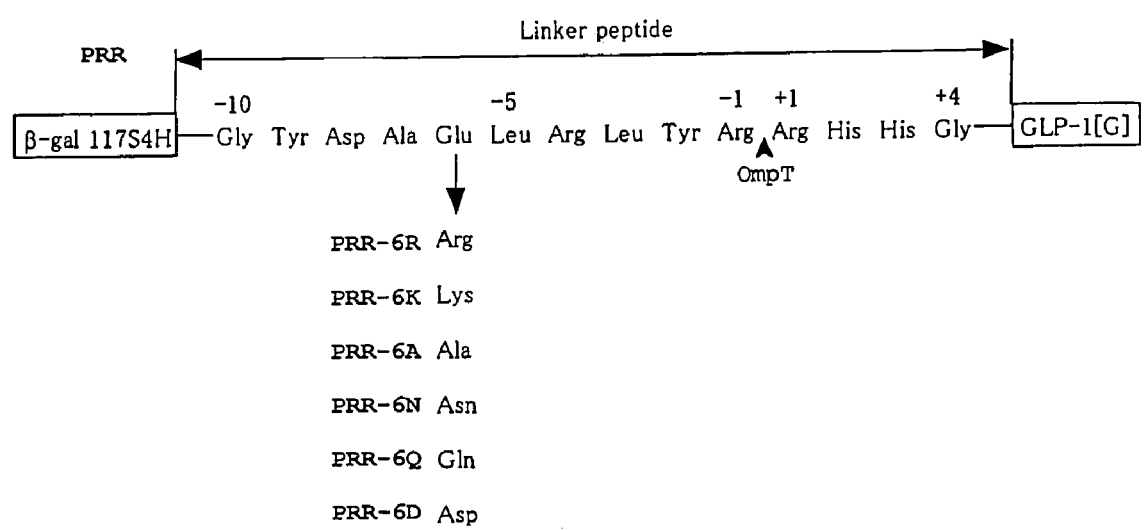

FIG. 32 is a diagrammatic illustration showing the structure of the fusion protein PRR-6X encoded by pG117ompPRR-6X, wherein –10, –5, –1, +1 and +4 respectively show the –10, –5, –1, +1 and +4-positions concerning the OmpT protease cleavage site of the fusion protein PRR. The amino acid sequence (from –10- to +4-positions) of the fusion proteins PRR and the substituted amino acid at the –6-position of the fusion protein PRR-6X are given in the figure. β-gal117S4H represents a protective protein derived from the N-terminal 117 amino acids of *E. coli* β-galactosidase; GLP-1[G] represents a human glucagon-like peptide-1; and Linker peptide (SEQ ID NO: 101) corresponds to an amino acid sequence from glutamine at the 128-position to arginine at the 153-position in the amino acid sequence shown in FIG. 6. The OmpT protease cleavage site in the fusion protein PRR is shown in this figure. The fusion proteins are represented in bold figures. PRR-6R is SEQ ID NO: 117; PRR-6K is SEQ ID NO: 118; PRR-6A is SEQ ID NO: 119; PRR-6N is SEQ ID NO: 120; PRR-6Q is SEQ ID NO: 121; and PRR-6D is SEQ ID NO: 122.

Figure 33:
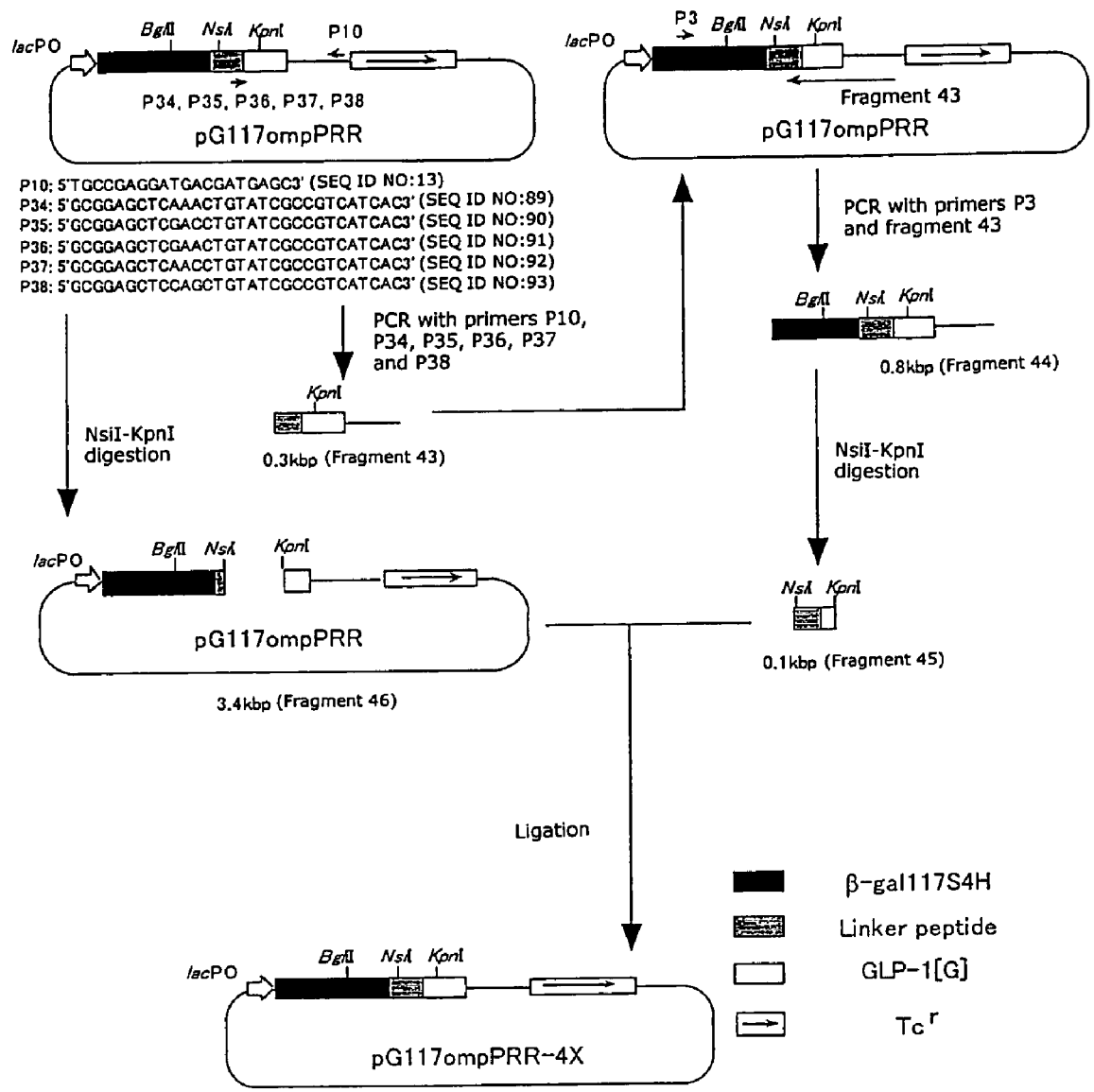

FIG. 33 is a diagrammatic illustration of the construction of pG117ompPRR-4X (wherein X is K, D, E, N or Q). In this figure, β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding the amino acid sequence from glutamine at the 128-position to arginine at the 153-position in the amino acid sequence shown in FIG. 6; and lac PO represents *E. coli* lactose promoter operator gene.

Figure 34:
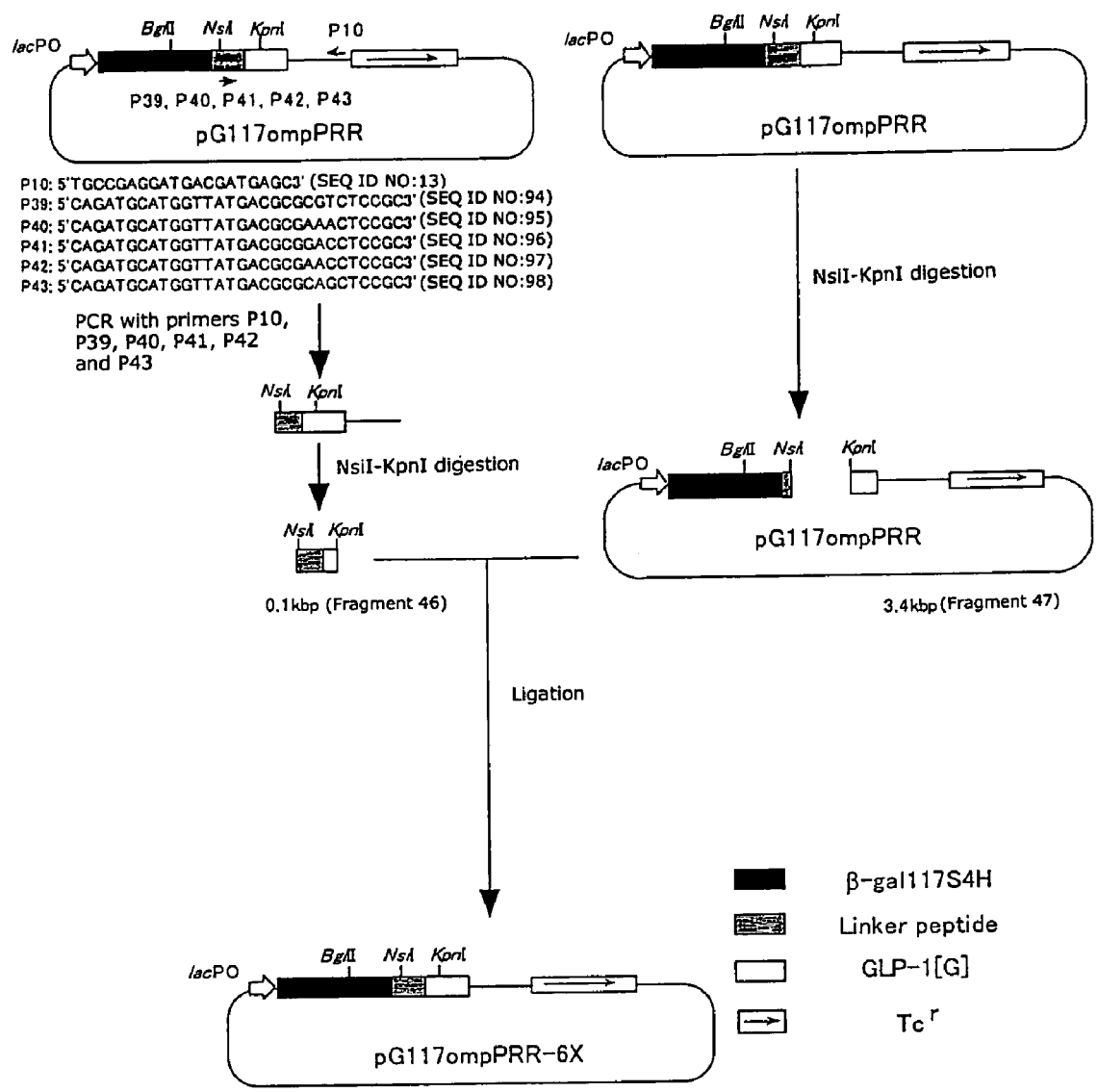

FIG. 34 is a diagrammatic illustration of the construction of pG117ompPRR-6X (wherein X is K, D, E, N or Q). In this figure, β-gal117S4H represents a region encoding a protective protein derived from the N-terminal 117 amino acids of *E. coli* β-galactosidase; GLP-1[G] represents a region encoding human glucagon-like peptide-1; Tc$^r$ represents a tetracycline-resistance gene; Linker peptide corresponds to the region encoding the amino acid sequence from glutamine at the 128-position to arginine at the 153-position in the amino acid sequence shown in FIG. 6; and lac PO represents *E. coli* lactose promoter operator gene.

Figure 35:
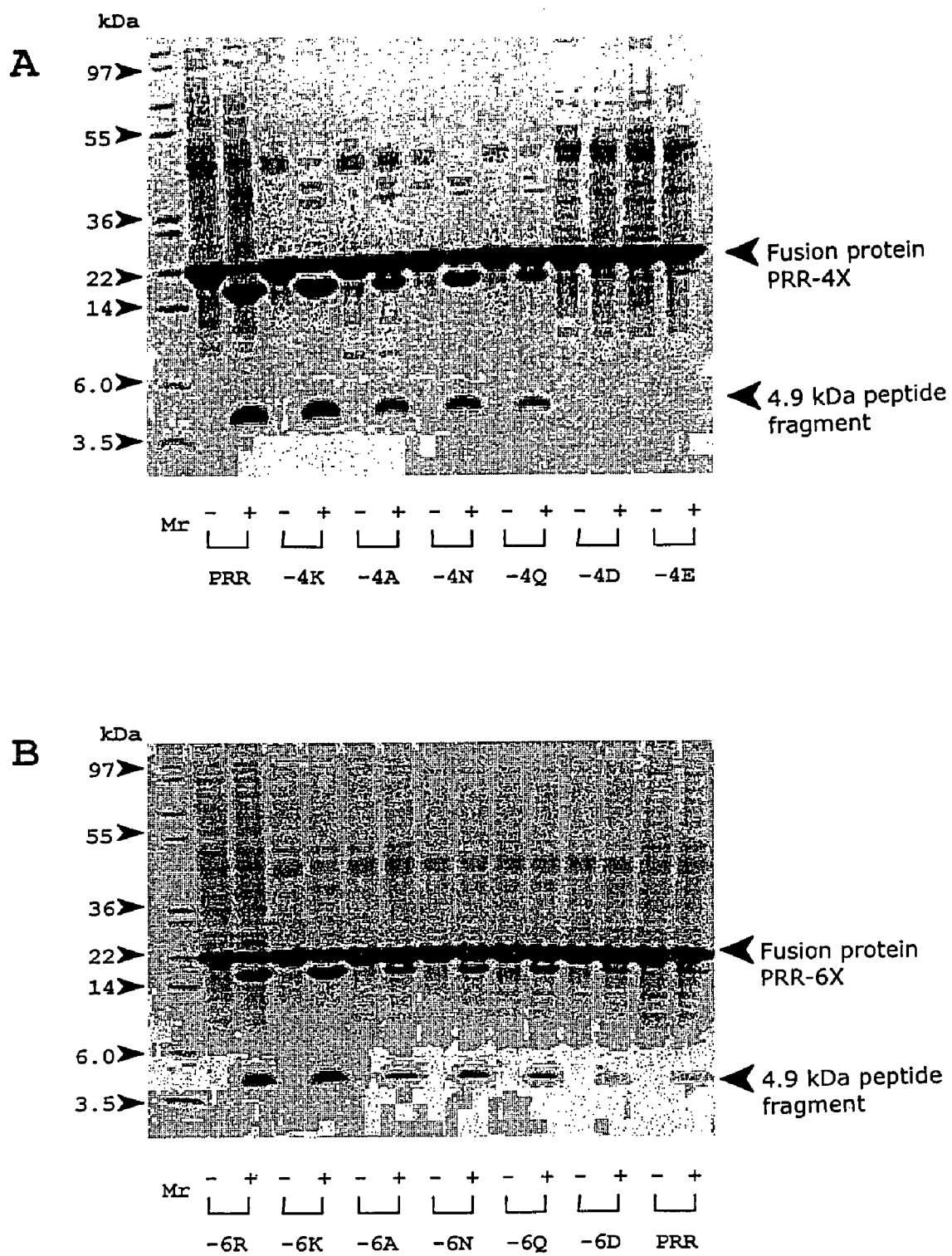

In FIG. 35, A is an SDS-PAGE (16%) photograph relating to the cleavage of the fusion proteins PRR and PRR-4X by OmpT protease. In this figure, Mr represents a protein molecular weight marker; – represents a lane free from OmpT protease; and + represents a lane with the addition of OmpT protease.

-4K: PRR-4K, -4A: PRR-4A, -4N: PRR-4N, -4Q: PRR-4Q, -4D: PRR-4D, -4E: PRR-4E

The 4.9 kDa peptide fragment means a peptide fragment containing GLP-1[G] which has been excised by OmpT protease.

In FIG. 35, B is an SDS-PAGE (16%) photograph relating to the cleavage of the fusion proteins PRR and PRR-6X by OmpT protease. In this figure, Mr represents a protein molecular weight marker; – represents a lane free from OmpT protease; and + represents a lane with the addition of OmpT protease.

-6R: PRR-6R, -6K: PRR-6K, -6A: PRR-6A, -6N: PRR-6N, -6Q: PRR-6Q, -6D: PRR-6D.

The 4.9 kDa peptide fragment means a peptide fragment containing GLP-1-[G] which has been excised by OmpT protease.

Figure 36:
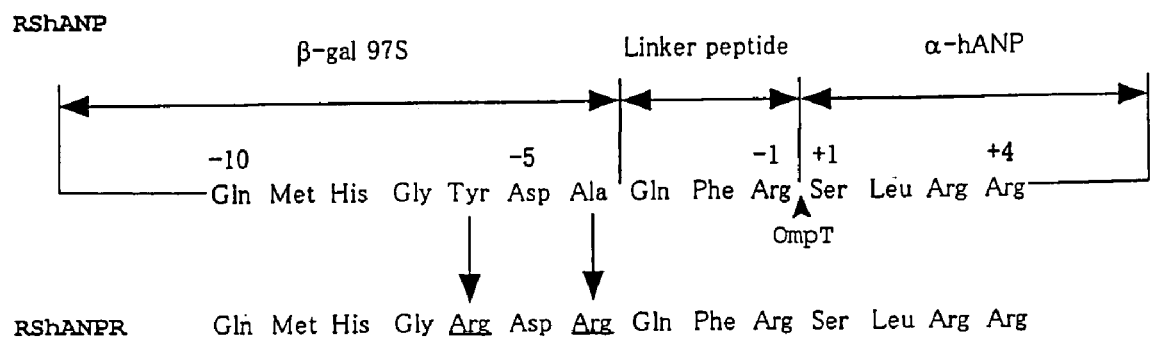

FIG. 36 is a diagrammatic illustration showing the structure of the fusion protein RShANPR encoded by pRShANPR, wherein –10, –5, –1, +1 and +4 respectively show the –10, –5, –1, +1 and +4-positions concerning the OmpT protease cleavage site of the fusion protein RShANP. The amino acid sequences (from –10- to +4-positions) of the fusion proteins RShANP (SEQ ID NO: 123) and RShANPR (SEQ ID NO: 124) are shown in the figure. β-gal97S4H represents a protective protein derived from the N-terminal 97 amino acids of *E. coli* β-galactosidase; α-hANP represents an β-type human atrial natriuretic peptide; and Linker peptide represents the amino acid sequence from glutamine at the 99-position to arginine at the 101-position in the amino acid sequence shown in FIG. 23. The OmpT protease cleavage site in the fusion protein RShANP is shown in this figure. The fusion proteins are expressed in bold figures and the substituted arginines at the –6- and –4-positions are underlined.

Figure 37:
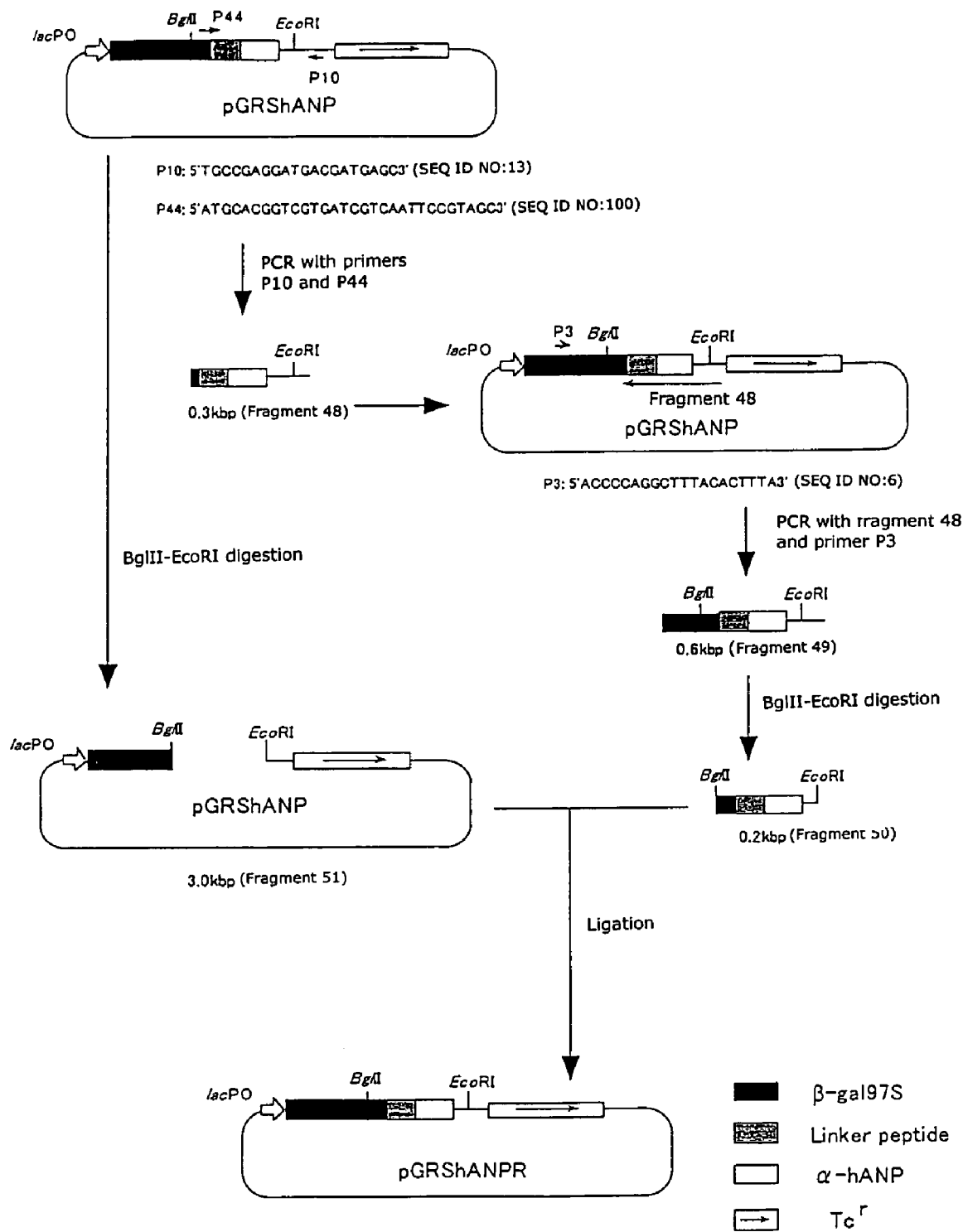

FIG. 37 is a diagrammatic illustration of the construction of pGRShANPR, wherein β-gal97S4H represents a region encoding a protective protein derived from the N-terminal 97 amino acids of *E. coli* β-galactosidase; α-hANP represents a region encoding α-type human atrial natriuretic peptide; Tc$^r$ represents a tetracycline-resistance gene; Linker peptide represents a region encoding an amino acid sequence QFR (SEQ ID NO:73); and lac PO represents *E. coli* lactose promoter operator gene.

DETAILED DESCRIPTION OF THE PREFERRED EMBODIMENTS

From the viewpoint that amino acid sequences in the vicinity of the cleavage sites are important in the substrate recognition and cleavage by OmpT protease, the present inventors examined amino acid sequences at the OmpT cleavage sites and peptides in the vicinity thereto by use of known cleavage sites, and have discovered new substrate specificity profiles of OmpT protease. To apply these new substrate specificity profiles to the cleavage of fusion proteins, the inventors have conducted intensive studies and consequently completed the present invention. More specifically, the present invention makes use of the property of OmpT protease which highly specifically acts so as to exclusively cleave an arginine-X bond or a lysine-X bond (wherein X is an amino acid other than glutamic acid, aspartic acid or proline) existing in specific amino acid sequences including known cleavage sites. The present invention also makes use of the property that cleavage efficiency is affected by the charges on the amino acids at the –6- and –4-positions of the cleavage site.

Accordingly, the present invention provides a method of controlling cleavage of a polypeptide by OmpT protease using the properties as described above, which comprises converting the amino acid(s) of a sequence site consisting of two arbitrary consecutive amino acids and/or amino acid(s) in the vicinity of said site in said polypeptide into another or other amino acid(s), characterized by (1) setting lysine or arginine as the amino acid at the –1-position of said site and setting a specific amino acid as the amino acid at the +1-position; and/or (2) setting specific amino acid(s) as the amino acid(s) at the –4-position and/or the –6-position from said site; so that a desired part of said polypeptide is cleavable by OmpT protease and/or an undesired part of said polypeptide is not cleavable by OmpT protease.

In one aspect, the present invention provides a method of controlling the release of a target polypeptide by OmpT protease which comprises setting lysine or arginine as the amino acid at the –1-position of a cleavage site in an amino acid sequence of a fusion protein containing the target polypeptide, which is cleavable by OmpT protease, and setting an amino acid X (wherein X is an amino acid other than glutamic acid, aspartic acid or proline) as the amino acid at the +1-position of the corresponding amino acid sequence (hereinafter referred to as the corresponding sequence). In another aspect, the present invention provides a method of increasing the cleavage efficiency by excising the target polypeptide while setting amino acid(s) other than acidic amino acid(s) (preferably basic amino acid(s) and still preferably lysine or arginine) as the amino acid(s) at the −6- and/or −4-positions of the cleavage site of the amino acid sequence cleavable by OmpT protease.

In one aspect of the invention, a fusion protein is expressed using genetic engineering techniques and is then cleaved in order to release the target polypeptide. In one example, the fusion protein may be expressed in such a manner as to contain "the corresponding sequence" at least as a part of the fusion protein. Then, OmpT protease is added and the target polypeptide is released. According to the present invention, moreover, the target polypeptide can be more efficiently excised by setting basic amino acids as the amino acids at the −6- and −4-positions of the cleavage site. The term "target polypeptide" as used herein means any polypeptide to be expressed as a fusion protein or a polypeptide obtained by secretory expression, direct expression, or the like. In a case of fusion proteins to be cleaved by OmpT protease, for example, polypeptides which exert physiological activity immediately after the cleavage by OmpT protease or as a result of post-translation modification may be used. Alternatively, production intermediates from which physiologically active peptides are formed after further cleavage following the above-described reaction (i.e., so called precursor peptides) may be employed therefor.

It is considered that the amino acid sequence to be cleaved by OmpT protease is defined as the sequence of from about −20- to +20-positions relative to the cleavage site. Accordingly, the "corresponding sequence" as used herein may be selected from among the amino acid sequences ranging from about −20- to +20-positions relative to the OmpT cleavage site. The OmpT cleavage site of an amino acid sequence may be a site that is already known or is experimentally confirmed as cleavable by OmpT protease. For example, the "corresponding sequence" may be selected from −20- to −1-positions, from −20- to +1-positions, from −1- to +20-positions or from +1- to +20-positions.

When an amino acid sequence cleavable by OmpT protease exists, the cleavage can be prevented in the method of the present invention by converting the amino acid at the +1-position of the cleavage site into glutamic acid, aspartic acid or proline. When such a conversion of the amino acid at the +1-position is impossible, the cleavage efficiency can be lowered by converting one or both of the amino acids at the −6- and −4-positions into acidic amino acid(s).

By combining the above methods, the cleavage by OmpT protease can be controlled. This is particularly convenient in a case wherein a fusion protein containing a target polypeptide is produced in *E. coli* (employed as a host) and the target polypeptide is excised from the fusion protein by the OmpT protease inherently possessed by *E. coli*.

Accordingly, the present invention relates to the following methods.

a) A method of controlling cleavage of a polypeptide by OmpT protease which comprises converting amino acid(s) of a sequence site consisting of two arbitrary consecutive amino acids and/or amino acid(s) in the vicinity of said site in said polypeptide into other amino acid(s), characterized by (1) setting lysine or arginine as the amino acid at the −1-position relative to said site and setting a specific amino acid as the amino acid at the +1-position; and/or (2) setting specific amino acid(s) as the amino acid(s) at the −4-position and/or the −6-position relative to said site; so that a desired part of said polypeptide is cleaved by OmpT protease and/or an undesired part of said polypeptide is not cleaved by OmpT protease.

b) The method as described in the above a) of controlling cleavage of polypeptides by OmpT protease which comprises converting amino acid(s) of a sequence site consisting of two arbitrary consecutive amino acids and/or amino acid(s) in the vicinity of said site in said polypeptide into other amino acids, characterized by (1) setting lysine or arginine as the amino acid at the −1-position relative to said site and setting a specific amino acid as the amino acid at the +1-position; and/or (2) setting specific amino acid(s) as the amino acid(s) at the −4-position and/or the −6-position relative to said site; so that a desired part of said polypeptide is cleaved by OmpT protease.

c) The method as described in the above b) characterized by (1) setting an amino acid other than glutamic acid, aspartic acid or proline as the amino acid at the +1-position; and/or (2) setting amino acid(s) (preferably basic amino acids and still preferably lysine or arginine) other than acidic amino acids as the amino acid(s) at the −4-position and/or the −6-position relative to said site.

d) A method as described in any of the above a) to c), comprising, where the amino acid at the −1-position of the sequence site consisting of two arbitrary consecutive amino acids in said polypeptide is neither lysine nor arginine, converting said amino acid into lysine or arginine and setting an amino acid X (wherein X is an amino acid other than glutamic acid, aspartic acid, proline, arginine, lysine, alanine, methionine or valine) as the amino acid at the +1-position so that a desired part of in said polypeptide is cleaved by OmpT protease.

e) The method as described in the above a) for controlling cleavage of polypeptides by OmpT protease which comprises converting amino acid(s) of a sequence site consisting of two arbitrary consecutive amino acids and/or amino acid(s) in the vicinity of said site in said polypeptide into other amino acids, characterized by (1) setting lysine or arginine as the amino acid at the −1-position relative to said site and setting a specific amino acid as the amino acid at the +1-position; and/or (2) setting specific amino acid(s) as the amino acid(s) at the −4-position and/or the −6-position relative to said site; so that a undesired part in said polypeptide is not cleaved by OmpT protease.

f) The method as described in the above e) characterized by (1) setting glutamic acid, aspartic acid or proline as the amino acid at the +1-position; and/or (2) setting acidic amino acid(s) as the amino acid(s) at the −4-position and/or the −6-position.

g) A method of applying the method as described in the above e) or f), wherein a gene encoding a polypeptide is expressed in host cells and said polypeptide is otherwise cleaved by OmpT protease at an undesired part.

h) A method of producing a polypeptide by expressing a gene encoding said polypeptide in host cells, characterized by converting amino acid(s) as described in the above a) to g), wherein said polypeptide is otherwise cleaved by OmpT protease at an undesired part.

i) A method as described in any of the above a) to f) which comprises expressing in host cells a gene encoding a fusion protein consisting of a target polypeptide fused with a protective peptide via a cleavage site (optionally located in a linker peptide) and being cleavable by OmpT protease at said cleavage site, and cleaving off the protein at said cleavage site by OmpT protease to thereby obtain the target polypeptide from the fusion protein.

j) The method as described in the above i) wherein an amino acid sequence cleavable by OmpT protease exists in the amino acid sequences of the protective peptide, the linker peptide and/or the target polypeptide constituting said fusion protein.

k) A method of producing a target polypeptide which comprises expressing in host cells a gene, which encodes a fusion protein consisting of a target polypeptide fused with a protective peptide via a cleavage site (optionally located in a linker peptide) and being cleavable by OmpT protease at said cleavage site, and cleaving off the protein at said cleavage site by OmpT protease to thereby obtain the target polypeptide from said fusion protein, characterized by using a method as described in any of the above a) to f) in converting the amino acids at the cleavage site and/or in the vicinity thereof.

l) The method as described in the above k) wherein an amino acid sequence cleavable by OmpT protease exists in the amino acid sequences of the protective peptide, the linker peptide and/or the target polypeptide constituting said fusion protein.

m) A method as described in any of the above g) to l) wherein the host cells is *E. coli*.

n) A method as described in any of the above g) to m) wherein the target polypeptide is a natriuretic peptide.

Proteins and peptides to which the method according to the present invention is applicable are as follows: Adrenocorticotropic Hormone, Adrenomedullin, Amylin, Angiotensin I, Angiotensin II, Angiotensin III, A-type Natriuretic Peptide, β-type Natriuretic Peptide, Bradykinin, Calcitonin, Calcitonin Gene Related Peptide, Cholecystokinin, Corticotropin Releasing Factor, Cortistatin, C-type Natriuretic Peptide, α-Defesin 1, β-Defesin 1, β-Defesin 2, Delta Sleep-Inducing Peptide, Dynorphin A, Elafin, α-Endorphin, β-Endorphin, β-Endorphin, Endothelin-1, Endothelin-2, Endothelin-3, Big Endothelin-1, Big Endothelin-2, Big Endothelin-3, Enkephalin, Galanin, Big Gastrin, Gastrin, Gastric Inhibitory Polypeptide, Gastrin Releasing Peptide, Ghrelin, Glucagon, Glucagon-like Peptide 1, Glucagon-like Peptide 2, Growth Hormone Releasing Factor, Growth Hormone, Guanylin, Uroguanylin, Histatin 5, Insulin, Joining Peptide, Luteinizing Hormone Releasing Hormone, Melanocyte Stimulating Hormone, Midkine, Motilin, Neurokinin A, Neurokinin B, Neuromedin B, Neuromedin C, Neuropeptide Y, Neurotensin, Oxytocin, Proadrenomedullin N-terminal 20 Peptide, Parathyroid Hormone, Parathyroid Hormone-Related Protein, Pituitary Adenylate Cyclase Activating Polypeptide 38, Platelet Factor −4, Peptide T, Secretin, Serum Thymic Factor, Somatostatin, Substance P, Thyrotropin Releasing Hormone, Urocortin, Vasoactive Intestinal Peptide, Vasopressin and the like and derivatives thereof (in the case of ANP among the above peptides, for example, use can be made of not only natural ANP consisting of 28 amino acids (i.e., ANP(1-28)) but also derivatives with deletion of amino acids in the amino acid sequence such as ANP(3-28) and ANP(4-28)).

The present invention will be described in greater detail.

pG117S4HompRHPR is an expression plasmid which expresses a fusion protein (PR) containing a glucagon-like peptide-1 (GLP-1[G]). The protective protein of this fusion protein consists of a protective protein originating in 117 amino acids from the N-terminus of *E. coli* β-galactosidase, a linker sequence consisting of 35 amino acids including an arginine-arginine sequence, and human glucagon-like peptide-1 (GLP-1[G]). The present inventors have already found out that *E. coli* OmpT protease cleaves the central peptide bond in the arginine-arginine sequence in the linker sequence so as to release the target peptide consisting of 44 amino acids containing GLP-1[G]. The present inventors converted the arginine-arginine sequence of the fusion protein encoded by pG117S4HompRHPR into arginine-X (wherein X represents the amino acid at the +1-position of the cleavage site) by site-specific mutagenesis based on PCR and examined whether or not the thus substituted fusion protein PRX (wherein X represents one letter code of the amino acid (selected from 20 amino acids in total) was cleaved by OmpT protease at this site. Thus, for example, a fusion protein having a substitution into alanine is represented as PRA. To express each fusion protein, an OmpT protease-deficient *E. coli* strain W3110 M25 was used. Since such a fusion protein was accumulated as an inclusion body in cells, the cells were disrupted and the inclusion body was collected by centrifugation. Then the inclusion body was solubilized with urea and employed in the OmpT protease reaction. The reaction was carried out by adding 20 mU of OmpT protease to a reaction solution containing 4 M of urea, 50 mM of sodium phosphate (pH 7.0), 2 mM of EDTA and each fusion protein inclusion body. The cleavage of the fusion protein was analyzed by SDS-PAGE (16%) and the N-terminal amino acid sequence of the target peptide thus excised was determined by using a protein sequencer.

As a result, it was clarified for the first time by the present inventors that OmpT protease has the activity of cleaving the center peptide bond in the arginine-X sequence wherein X is an amino acid other than aspartic acid, glutamic acid or proline. Thus, the present inventors clarified that OmpT protease has the activity of cleaving not only the amino acid sequences reported so far (namely, arginine-arginine, arginine-lysine, lysine-arginine, lysine-lysine, arginine-alanine, arginine-methionine and arginine-valine) but also the amino acid sequences represented by arginine-X (wherein X is an amino acid other than aspartic acid, glutamic acid and proline).

By using these fusion proteins, it was further examined whether or not the lysine-X (wherein X is located at the +1-position of the cleavage site and represents alanine, serine, lysine, arginine, aspartic acid or glutamic acid) was cleaved and similar results were obtained thereby. It is anticipated that OmpT protease is largely affected by the amino acid sequence in the vicinity of the cleavage site. Therefore, the examination was further carried out to study whether or not fusion proteins PRhANP and PRhCT (wherein the target peptide region of the fusion protein PR was substituted respectively with α-hANP (α-type human atrial natriuretic peptide) and hCT[G] (human calcitonin precursor)) could be cleaved by OmpT protease. As a result, it was found out that PRhANP was cleaved by OmpT protease between arginine and serine and thus α-hANP was excised therefrom. On the other hand, PRhCT was not cleaved by OmpT protease. The fact that the arginine-cysteine sequence of PRhCT was not cleaved by OmpT protease indicates that the recognition and cleavage of a substrate by OmpT protease are affected by the amino acid sequence in the vicinity of the cleavage site, which supports the significance of using known amino acid sequences cleaved by OmpT protease as proposed by the present inventors.

The above-described results were obtained by a series of studies with the use of the fusion protein PR having amino acid sequences of known cleavage sites. Moreover, it was examined whether or not similar results would be obtained by substituting the amino acid at the +1-position of another fusion protein RShANP (i.e., an α-hANP fusion protein having an amino acid sequence different from PR around the cleavage site). The fusion protein RShANP employed in this examination consists of β-gal197S, which originates in 97 amino acids from the N-terminus of E. coli β-galactosidase, as a protective protein, and α-hANP bonded thereto via a linker consisting of three amino acids (glutamine-phenylalanine-arginine). Attempts were made to cleave fusion proteins by OmpT protease wherein the amino acid at the +1-position of this fusion protein had been substituted by arginine, alanine and cysteine. As a result, it was found out that these fusion proteins having been substituted the amino acid at the +1-position were also cleaved by OmpT protease to give the N-terminal derivative of α-hANP.

These results indicate that when a region having a known OmpT protease-cleavage sequence (wherein the −1- and +1-positions at the cleavage site are represented by Arginine-X or lysine-X) is employed and said X is substituted by an amino acid other than aspartic acid, glutamic acid or proline, the fusion protein thus substituted is still cleaved by OmpT protease. Therefore, when a fusion protein consisting of a protective peptide, the amino acid sequence of an OmpT protease-cleavage site and a target peptide in this order is to be cleaved by this enzyme, it is possible to select the amino acid added to the N-terminus of the target peptide from among amino acids other than aspartic acid, glutamic acid and proline. By using this method, a derivative having a different amino acid at the N-terminus of a target peptide can be constructed. It is also possible to substitute the N-terminal amino acid so as to increase the separation/purification efficiency. It is also possible to convert a sequence which is not cleaved to a cleavable sequence.

By using the results that a peptide having X as aspartic acid, glutamic acid or proline is not cleavable by OmpT protease, moreover, it is possible to convert a fusion protein or protein into one which cannot be digested by OmpT protease. More specifically, it is sometimes observed that, in the process of producing a protein expressed in E. coli, the target protein can be hardly isolated due to digestion by OmpT protease. In such a case, the protein can be converted into a fusion protein or protein by substituting the recognition amino acid at the +1-position of the cleavage site into aspartic acid, glutamic acid or proline, which obviously facilitates the production.

The present inventors further substituted amino acids at the −10- to −1-positions of the OmpT protease cleavage site of the fusion protein PRR and examined the cleavage of these fusion proteins by OmpT protease. As a result, they have found that the N-terminal amino acid sequence of the cleavage site affected the cleavage efficiency. In particular, the cleavage efficiency was elevated by setting a basic amino acid such as arginine or lysine as the amino acid at the −4-position but lowered by setting an acidic amino acid such as aspartic acid or glutamic acid. Similar results were obtained concerning the amino acid at the −6-position. Based on these results, it is considered that OmpT protease recognizes the electric charges of the amino acids at these positions. When arginine at the −1-position was substituted by alanine, no cleavage occurred. This fact indicates again that the amino acid at this position serves an important role in the cleavage.

In addition, RShANP which is an α-hANP fusion protein having a different amino acid sequence around the cleavage site form PRR was used, and the increase in the cleavage efficiency was observed in a fusion protein RShANPR wherein tyrosine and alanine at the −6- and −4-positions respectively in the cleavage site had been substituted both by arginine.

Accordingly, the cleavage efficiency can be improved by converting either or both of the amino acids at the −6- and −4-positions into a basic amino acid, while the cleavage efficiency can be lowered by converting these amino acids into an acidic one. Thus, the cleavage efficiency can be controlled to a certain extent without substituting the amino acids at the cleavage site (i.e., −1- or +1-position).

Moreover, experimental operations not described in the Examples will be first described in detail.

(1) Materials and Methods

Unless otherwise stated in the Examples, the experimental operations were carried out as follows.

Synthesis of DNA primers was entrusted to Pharmacia. Nucleotide sequences were determined by using a A.L.F. DNA Sequencer (manufactured by Pharmacia) with the use of a Thermo Sequenase florescent labeled primer cycle sequencing kit with 7-deaze dGTP (manufactured by Amersham). Plasmid DNAs were isolated from E. coli by using a PI-100Σ (manufactured by Kurabo). To cleave DNA with restriction enzymes, the reaction was carried out at 500 to 2000 U/ml for 2 hours. The structure of a plasmid was analyzed in 10 µl of a liquid reaction mixture with the use of 0.5 to 1 µg of DNA. A DNA fragment was prepared in 30 µl of a liquid reaction mixture with the use of 5 to 10 µg of DNA. The reaction conditions (temperature, buffer, etc.) were determined according to the manufacturer's instructions.

Samples for agarose gel electrophoresis were prepared by adding a 1/10 volume of sample buffer to the liquid reaction mixture. As the buffer for agarose gel electrophoresis, use was made of TAE buffer (40 mM Tris-acetic acid, 1 mM EDTA). The electrophoresis was effected at 100 V for 30 minutes to 1 hour. After staining with an aqueous ethidium bromide solution, the gel was UV-irradiated to detect DNA bands. The concentration of the agarose gel was adjusted to 0.8 or 2.0% (w/v) depending on the size of the DNA fragment to be fractionated. After the agarose gel electrophoresis, the target DNA band was cut out and the DNA was extracted from the gel by using SUPREC-01 (manufactured by Takara Shuzo). This DNA solution was treated with phenol/chloroform, then precipitated from ethanol and dissolved in TE buffer (10 mM Tris-HCl (pH 8.0), 1 mM EDTA). Ligation reaction was carried out by using Ligation high (manufactured by Toyobo) at a predetermined reaction mixture composition at 16° C. for 30 minutes or overnight. PCR was carried out by using KOD Dash or KOD DNA polymerase (manufactured by Toyobo). The PCR conditions (temperature, buffer, etc.) and the composition of the liquid reaction mixture were determined each according to the manufacturer's instructions.

Transformation of E. coli with a plasmid was carried out by the calcium chloride method by using JM109 strain purchased from Takara Shuzo as competent cells. The transformant was selected with the use of tetracycline (10 µg/ml). Unless otherwise stated in Examples, JM109 was employed for the transformation of E. coli.

(2) Measurement of Enzymatic Activity of OmpT Protease

Activity of OmpT protease was measured by using Dynorphine A as a substrate (manufactured by Peptide Institute Inc.).

A 5 µg aliquot of 1 mg/ml Dynorphine A was added to 40 µl of 50 mM sodium phosphate (pH 6.0) containing 0.1% Triton X-100. Then 5 µl of a sample for measuring OmpT protease activity was added thereto and the reaction was initiated. The reaction was carried out at 25° C. for 10 minutes and then stopped by adding 5 µl of 1 N HCl. The liquid reaction mixture was centrifuged (10000×g, 2 minutes). The supernatant was collected and a 20 µl portion thereof was analyzed by HPLC. The HPLC analysis was carried out by using YMC PROTEIN RP column at column temperature of 40° C. and at flow rate of 1 ml/min. After washing with 10% acetonitrile containing 0.1% of trifluoroacetic acid for 3 minutes, the mixture was subjected to linear gradient elution with 10-15% acetonitrile containing 0.1% trifluoroacetic acid for 10 minutes. The absorption at 220 nm was monitored and thus the digestion product peptide YGGFLR was detected. The unit of OmpT protease activity was defined as the cleavage of 1 µmol Dynorphine A at 25° C. per minute under these conditions.

(3) SDS-Polyacrylamide Gel Electrophoresis

SDS-polyacrylamide gel electrophoresis was carried out by using 16% Wide-PAGEmini (manufactured by Tefco) as a gel, Tricine electrophoretic buffer (manufactured by Tefco) as an electrophoretic buffer, and molecular weight marker proteins (manufactured by Tefco) as molecular weight markers. The equivalent amount of 2×SDS-PAGE sample buffer containing 4 M urea (provided that the urea is not contained in a case of analyzing OmpT protease protein) was added to a sample and the mixture was heated to 100° C. for 2 minutes. Then 10 µl portion thereof was electrophoresed under the conditions according to Tefco's instructions. After the completion of the electrophoresis, the gel was stained with a staining solution containing Coomassie Brilliant Blue R-250.

(4) Preparation of Inclusion Body

Fusion proteins PRX, PKX, PRhANP, PRhCT, RShANP, RXhANP, PRRXA, PRR-4X, PRR-6X and RShANPR were each prepared as an inclusion body in the following manner.

E. coli expressing each of PRX, PKX, PRhANP, PRhCT, RShANP, RXhANP, PRRXA, PRR-4X, PRR-6X and RShANPR was cultured under rotation at 150 rpm, 37° C. overnight in 2 l Erlenmeyer flasks containing 400 ml of an LB liquid medium (0.5% (w/v) yeast extract, 1% (w/v) tryptone, 0.5% sodium chloride) containing 10 mg/l tetracycline. On the next day, the cells were collected by centrifugation (4° C., 6000×g, 10 minutes) and disrupted by ultrasonication. Deionized water was added to this disrupted cell solution to give a total volume of 30 ml. Then the mixture was centrifuged (4° C., 25000×g, 15 minutes) and the supernatant was discarded. The precipitate fraction (inclusion body) was recovered and further suspended in 30 ml of 50 mM Tris HCl (pH 8.0) containing 5 mM EDTA and 1% Triton X-100. The suspension was centrifuged (4° C., 25000×g, 15 minutes). The precipitate thus obtained was suspended in deionized water and centrifuged (4° C., 25000×g, 15 minutes). Then the precipitate was recovered and deionized water was added thereto to give a total volume of 1.5 ml. After suspending the precipitate, the suspension was centrifuged (4° C., 10000×g, 30 minutes) to give precipitate. Then the above procedure was repeated so as to give a suspension of the precipitate in deionized water of $OD_{660}=100$ or $OD_{660}=200$. The inclusion bodies thus prepared were employed as substrates in the OmpT protease reaction.

(5) OmpT Protease Reaction

By using as the substrate PRX, PKX, PRhANP, PRhCT, PRRXA, PRR-4X and PRR-6X, the OmpT protease reaction was carried out in the following manner. To 20 µl of 10 M urea were added 2.5 µl of 1 M sodium phosphate (pH 7.0) and 2 µl of 50 mM EDTA. Then 10 µl of a fusion protein inclusion body ($OD_{660}=100$) was added thereto and the inclusion body was dissolved. After adding 10.5 µl of water, 5 µl of 4 U/ml (20 U/ml in the case of PRR-4X, 1 U/ml in the case of PRR-6X) of OmpT protease was added thereto and the reaction was initiated at a liquid reaction mixture volume of 50 µl. The reaction was carried out at 25° C. for 30 or 60 minutes.

The peptides obtained by the OmpT protease reaction with the use of PRX, PKX, PRRXA, PRR-4X and PRR-6X as the substrates were each isolated and quantitated by HPLC under the conditions as specified below. To the OmpT protease reaction mixture, the equivalent amount of 12% acetic acid and 4 M urea were added to thereby cease the reaction. Then the liquid reaction mixture was centrifuged (10000×g, 2 minutes) and 20 µl portion or a 50 µl portion of the supernatant was treated with YMC PROTEIN RP column. HPLC was carried out at column temperature of 40° C. at a flow rate of 1 ml/min. After performing linear gradient elution with 30-50% acetonitrile containing 0.1% trifluoroacetic acid for 16 minutes, the absorption at 214 nm was monitored and thus the peptide was isolated and quantitated.

By using as the substrates RShANP and RXhANP, the OmpT protease reaction was carried out in the following manner. To 20 µl of 10 M urea were added 2.5 µl of 1 M sodium phosphate (pH 7.0) and 2 µl of 50 mM EDTA. Then 5 µl of a fusion protein inclusion body ($OD_{660}=200$) was added thereto and the inclusion body was dissolved. After adding 15.5 µl of water, 5 µl of 10 U/ml of OmpT protease was added thereto and the reaction was initiated at 50 µl of a liquid reaction mixture volume. The reaction was carried out at 37° C. for 120 minutes.

By using as the substrates RShANP and RShANPR, the OmpT protease reaction was carried out in the following manner. To 8 µl of 10 M urea were added 1.0 µl of 1 M sodium phosphate (pH 7.0) and 0.8 µl of 50 mM EDTA. Then 4 µl of the fusion protein inclusion body ($OD_{660}=100$) was added thereto and the inclusion body was dissolved. After adding 4.2 µl of water, 2 µl of 20 U/ml OmpT protease was added thereto and the reaction was initiated at a liquid reaction mixture volume of 20 µl. The reaction was carried out at 25° C. for 90 minutes.

The peptides obtained by the OmpT protease reaction with the use of PRhANP, RShANP, RXhANP and RShANPR as the substrates were each isolated and quantitated by HPLC under the conditions as specified below. To the OmpT protease reaction mixture, the equivalent amount of 12% acetic acid and 4 M urea were added to thereby cease the reaction. Then the liquid reaction mixture was centrifuged (10000×g, 2 minutes) and 20 µl portion or 50 µl portion of the supernatant was treated with YMC A-302 ODS column. HPLC was carried out at a column temperature of 40° C. and a flow rate of 1 ml/min. After performing linear gradient elution with 21.5-32% acetonitrile containing 0.1% trifluoroacetic acid for 15 minutes, the absorption at 214 nm was monitored and thus the peptide was isolated and quantitated.

(6) Analysis of N-Terminal Amino Acid Sequence of Peptide

The N-terminal amino acid sequence of each peptide thus obtained was determined with respect to 5 amino acid residues by using Protein Sequencer 477A-120A or PROCISE 492 (manufactured by ABI).

EXAMPLES

The present invention will be described in greater detail by reference to the following Examples.

Example 1

Preparation of Fusion Protein PRX

OmpT protease is an endoprotease which exists in E. coli outer membrane. Although this enzyme has a high substrate specificity, the characteristics of the amino acid sequences in the substrate recognized by the enzyme have not been sufficiently clarified so far. It is known that OmpT protease cleaves the center bond of basic amino acid pairs (arginine-arginine, arginine-lysine, lysine-arginine and lysine-lysine). In addition, it is reported that OmpT protease cleaves the C-terminal peptide bond of basic amino acid (arginine-methionine, arginine-alanine and arginine-valine). However, OmpT protease does not always cleave these sites in the amino acid sequences of proteins and peptides, and the cleavage by this enzyme is greatly affected by the amino acid sequence in the vicinity of the cleavage site. It is therefore estimated that the enzyme has a high substrate specificity and cleaves exclusively specific sites. The present inventors expected that a novel substrate specificity of this enzyme would be found by examining the amino acid sequence at the +1-position of the cleavage site with the use of known cleavage sites of this enzyme. From this viewpoint, they conducted the following experiments.

Figure 6:
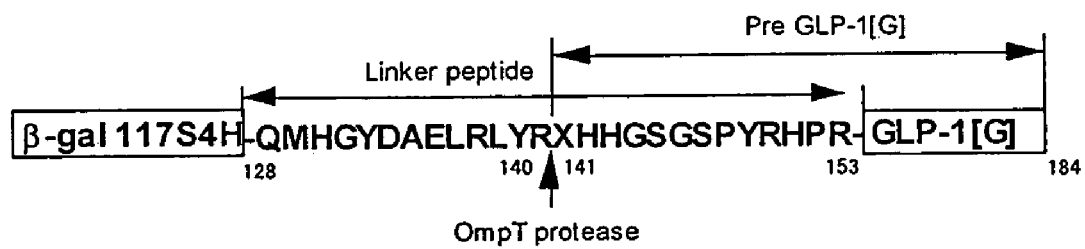
FIG. 6 is a diagrammatic illustration showing the structure of a fusion protein PRX encoded by pG117ompPRX, wherein numerical symbols show the amino acid numbers counting from the N-terminus of the fusion protein PRX. β-gal117S4H represents a protective protein derived from the N-terminal 117 amino acids of *E. coli* β-galactosidase; GLP-1[G] represents a human glucagon-like peptide-1; Pre GLP-1[G] represents a target peptide comprising an amino acid sequence from the 141- to 184-positions containing GLP-1[G]; and Linker peptide represents an amino acid sequence from glutamine at the 128-position to arginine at the 153-position (SEQ ID NO: 127). A site (arginine 140-X141) corresponding to the OmpT protease cleavage site in the fusion protein PR is shown in this figure.

At the +1-position of a fusion protein PR (i.e., a fusion protein consisting of a protective protein (β-gal117S4H) derived from the 117 amino acids in the N-terminus of E. coli β-galactosidase and human glucagon-like peptide-1 (GLP-1[G])) having the structure as shown in FIG. 4 which is cleavable by OmpT protease, an amino acid substitution was made to thereby form fusion protein PRX (FIG. 6: wherein X represents one letter code of the amino acid substituted (20 types in total); namely, a fusion protein having substitution into alanine is represented as PRA). In the fusion protein PRX, the OmpT protease cleavage site -RLYR↓RHHG- (SEQ ID NO: 1) of the original fusion protein PR was converted into -RLYRXHHG- (SEQ ID NO: 2). Then cleavage by OmpT protease was examined.

The fusion protein PRX was prepared by the following five steps.

Figure 1:
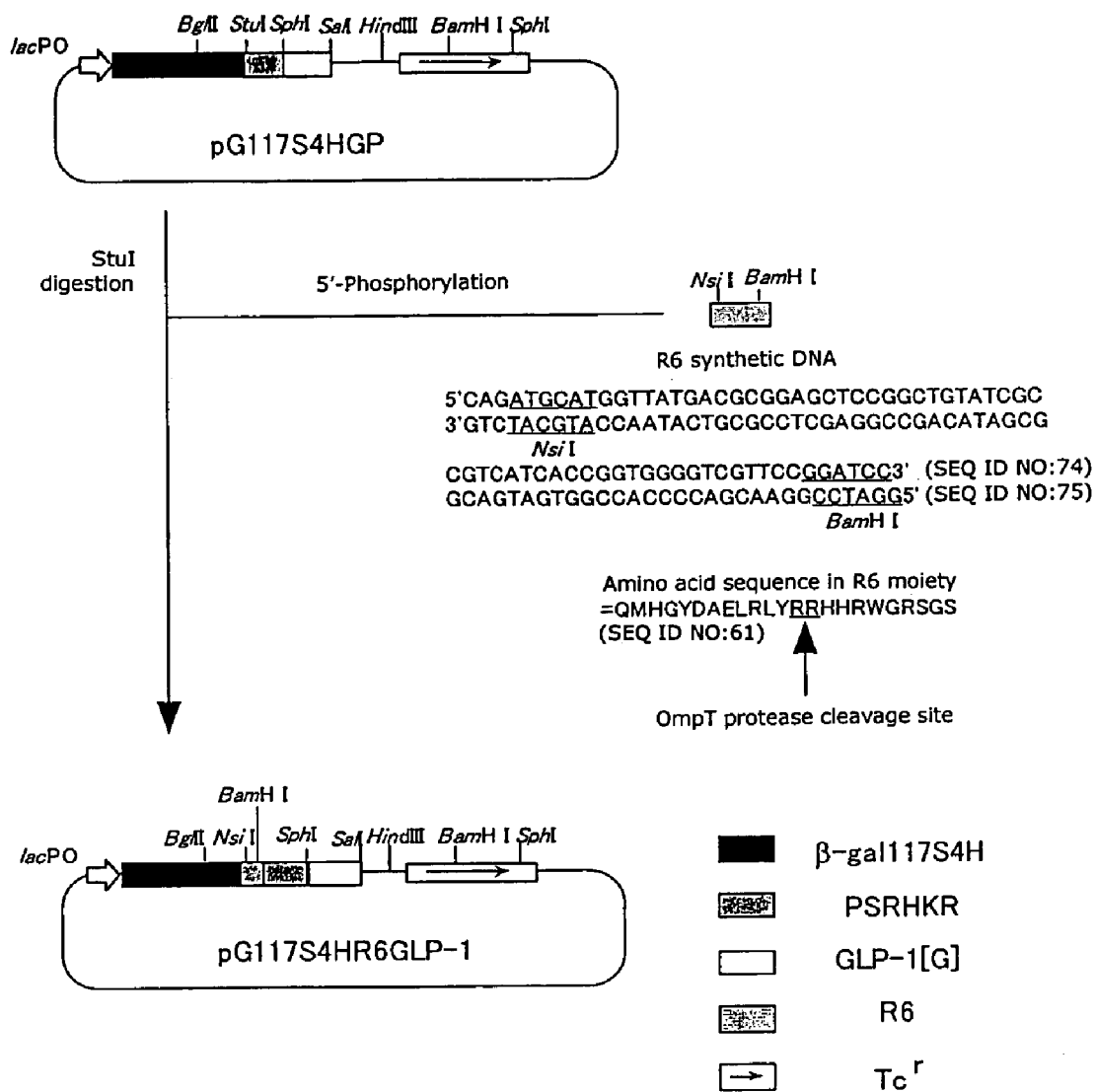
FIG. 1 is a diagrammatic illustration of the construction of pG117S4HR6GLP-1, wherein β-gal117S4H represents a region encoding a protective protein derived from the N-terminal 117 amino acids of E. coli β-galactosidase; PSRHKR represents a region encoding an amino acid sequence PSRHKR (SEQ ID NO:60); GLP-1[G] represents a region encoding human glucagon-like peptide-1; R6 represents a region encoding an amino acid sequence QMHGYDAEL-RLYRRHHRWGRSGS (SEQ ID NO:61); Tc$^r$ represents a tetracycline-resistance gene; and lac PO represents E. coli lactose promoter operator gene. With respect to pG117S4HGP, see Japanese Laid-Open Patent Publication No. 9-296000 and EP 794255.

(1) Step 1: Construction of pG117S4HR6GLP-1 (FIG. 1)

First, plasmid pG117S4HR6GLP-1 was constructed.

This plasmid carried a sequence arginine-arginine which was inserted as the OmpT protease recognition/cleavage site into the linker moiety of the fusion protein. In the construction, the R6 synthesis DNA sequence (See FIG. 1) was inserted into the StuI site of pG117S4HGP (see Japanese laid-Open Patent Publication No. 9-296000 and EP 794255) to thereby give pG117S4HR6GLP-1. In FIG. 1, β-gal117S4H represents a protective protein derived from the 117 amino acids in the N-terminus of E. coli β-galactosidase and GLP-1 [G] represents human glucagon-like peptide-1.

Figure 2:
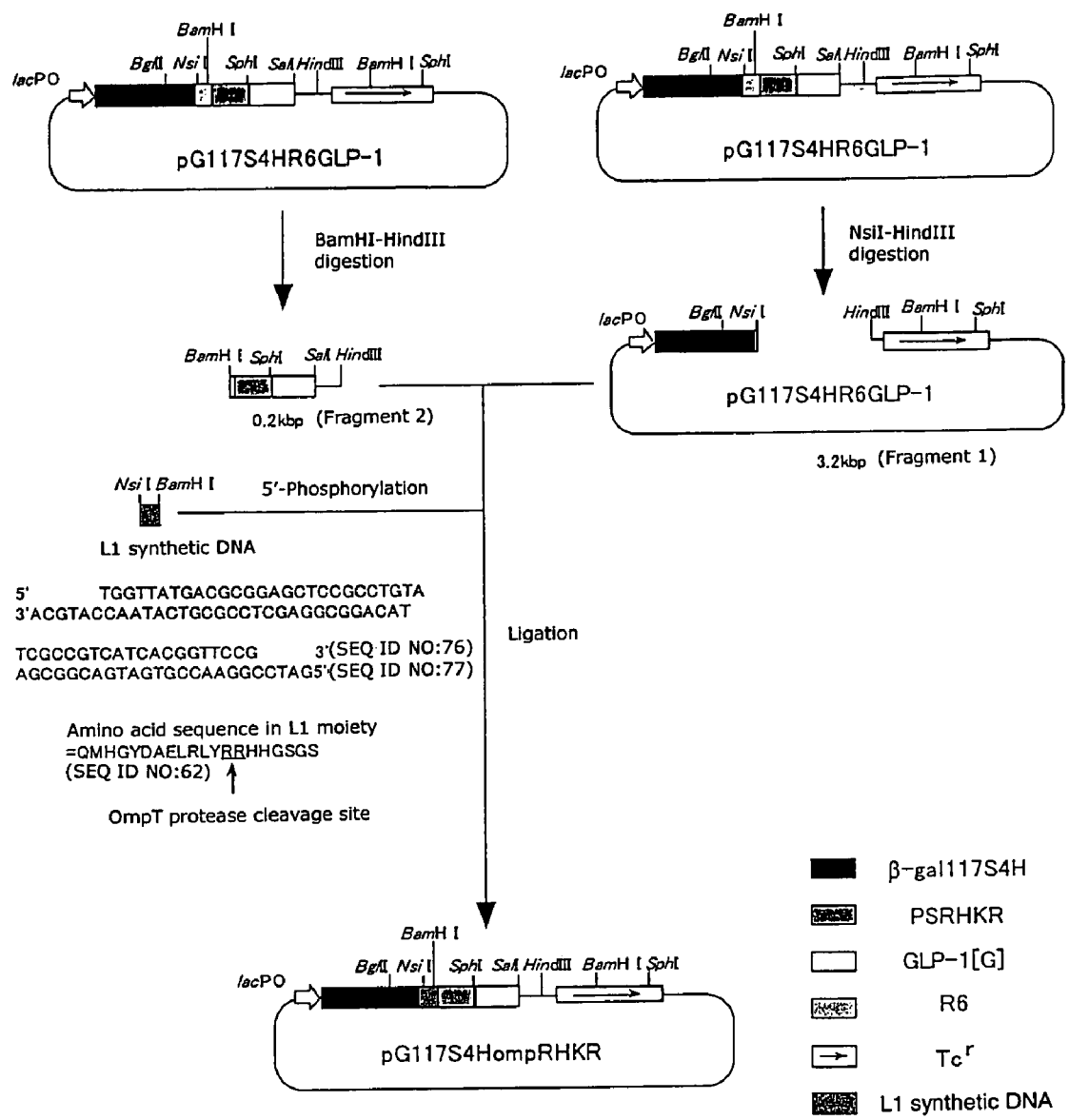
FIG. 2 is a diagrammatic illustration of the construction of pG117S4HompRHKR, wherein β-gal117S4H represents a region encoding a protective protein derived from the N-terminal 117 amino acids of E. coli β-galactosidase; PSRHKR (SEQ ID NO: 60) represents a region encoding an amino acid sequence PSRHKR (SEQ ID NO: 60); GLP-1[G] represents a region encoding human glucagon-like peptide-1; R6 represents a region encoding an amino acid sequence QMHGYDAELRLYRRHHRWGRSGS (SEQ ID NO:61); TC^r represents a tetracycline-resistance gene; L1 represents an amino acid sequence QMHGYDAELRLYRRHHGSGS (SEQ ID NO:62); and lac PO represents *E. coli* lactose promoter operator gene.

(2) Step 2: Construction of pG117S4HompRHKR (FIG. 2)

To further enhance the cleavage efficiently by OmpT protease, the sequence in the R6 moiety was modified in the following manner. A 3.2 kbp fragment (fragment 1) obtained by cleaving pG117S4HR6GLP-1 by NsiI and HindIII, a 0.2 kbp fragment (fragment 2) obtained by pG117S4HR6GLP-1 by BamHI and HindIII, and an L1 synthesis DNA (see FIG. 2) encoding an amino acid sequence L1 (see FIG. 2) having an arginine-arginine sequence (i.e., the recognition/cleavage site of OmpT protease) were ligated together to thereby construct pG117S4HompRHKR.

Figure 3:
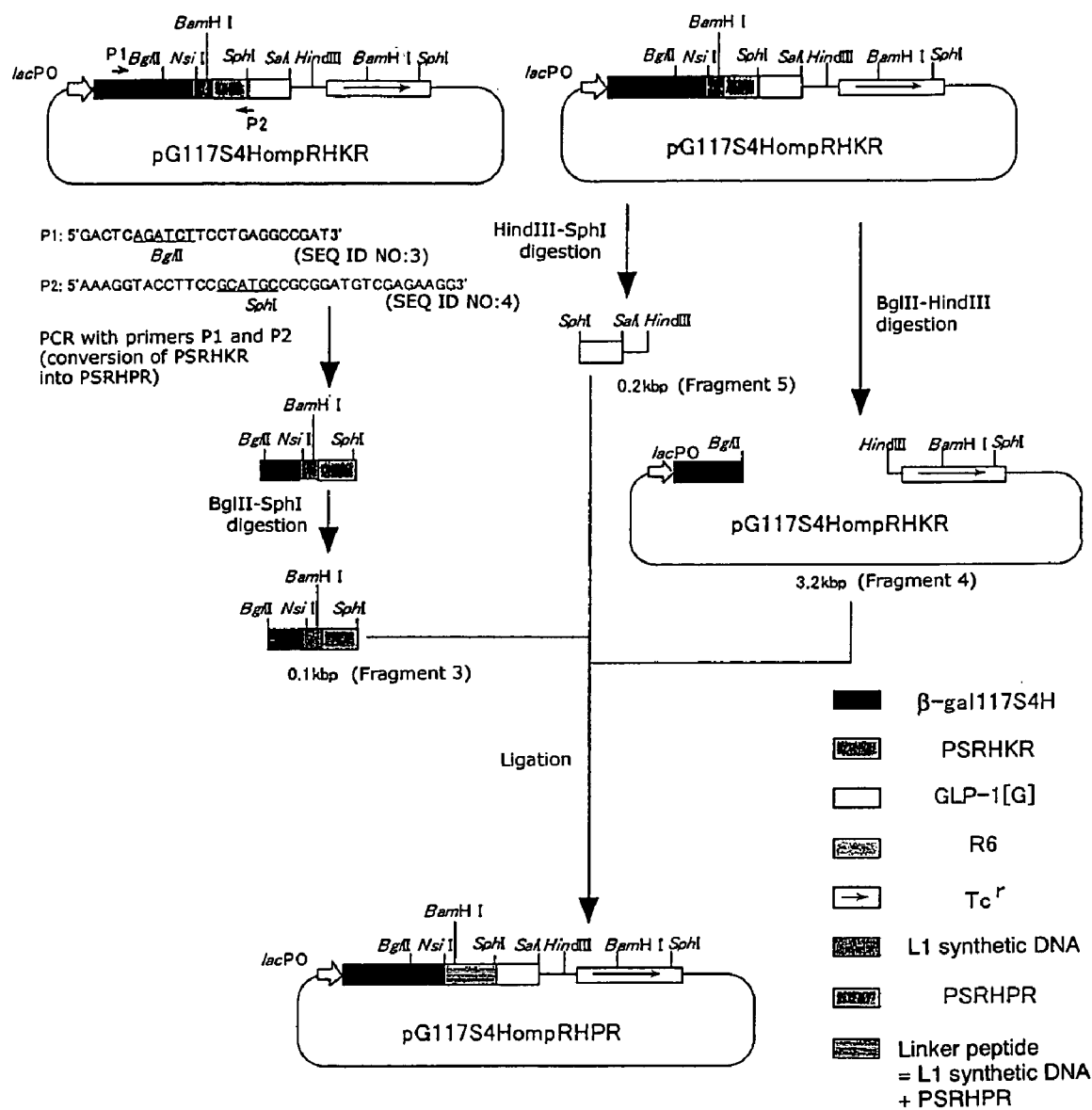
FIG. 3 is a diagrammatic illustration of the construction of pG117S4HompRHPR, wherein β-gal117S4H represents a region encoding a protective protein derived from the N-terminal 117 amino acids of *E. coli* β-galactosidase; PSRHKR (SEQ ID NO: 60) represents a region encoding an amino acid sequence PSRHKR (SEQ ID NO: 60); GLP-1[G] represents a region encoding human glucagon-like peptide-1; R6 represents a region encoding an amino acid sequence QMHGYDAELRLYRRHHRWGRSGS (SEQ ID NO: 61); Tc^r represents a tetracycline-resistance gene; L1 represents an amino acid sequence QMHGYDAELRLYRRHHGSGS (SEQ ID NO: 62); PSRHPR (SEQ ID NO: 63) represents a region encoding an amino acid sequence PSRHPR(SEQ ID NO:63); Linker peptide represents a region encoding an amino acid sequence QMHGYDAELRLYRRHHGSG-SPSRHPR (SEQ ID NO:64) wherein L1 is a synthetic DNA ligated to PSRHPR (SEQ ID NO: 63); and lac PO represents *E. coli* lactose promoter operator gene.

(3) Step 3: Construction of pG117S4HompRHPR (FIG. 3)

Since a lysine-arginine (KR) sequence (corresponding to the 152- and 153-positions in FIG. 4) positioned immediately before the N-terminus of the fusion protein GLP-1-[G] expressed by pG117S4HompRHKR is cleavable by OmpT protease, it has been known by preliminarily experiments that this fusion protein is cleaved at two sites when treated with OmpT protease. To facilitate the analysis, therefore, this sequence was substituted by proline-arginine (PR) to thereby to prevent it from cleavage by OmpT protease. Primers P1:5'-GACTCAGATCTTCCTGAGGCCGAT-3' (SEQ ID NO: 3) and P2:5'-AAAGGTACCTTCCGCATGC-CGCGGATGTCGAGAAGG-3' (SEQ ID NO: 4) were synthesized and PCR was performed with the use of pG117S4HompRHKR as a template to give a 0.1 kbp DNA fragment. The obtained fragment was treated with BglII and SphI (fragment 3) and then ligated to a 3.2 kbp fragment (fragment 4) obtained by cleaving pG117S4HompRHKR by BglII and HindIII and a 0.2 kbp fragment (fragment 5) obtained from pG117S4HompRHKR by SphI and HindIII to thereby construct pG117S4HompRHPR. FIG. 4 shows the whole amino acid sequence of the fusion protein PR encoded by pG117S4HompRHPR.

Figure 5:
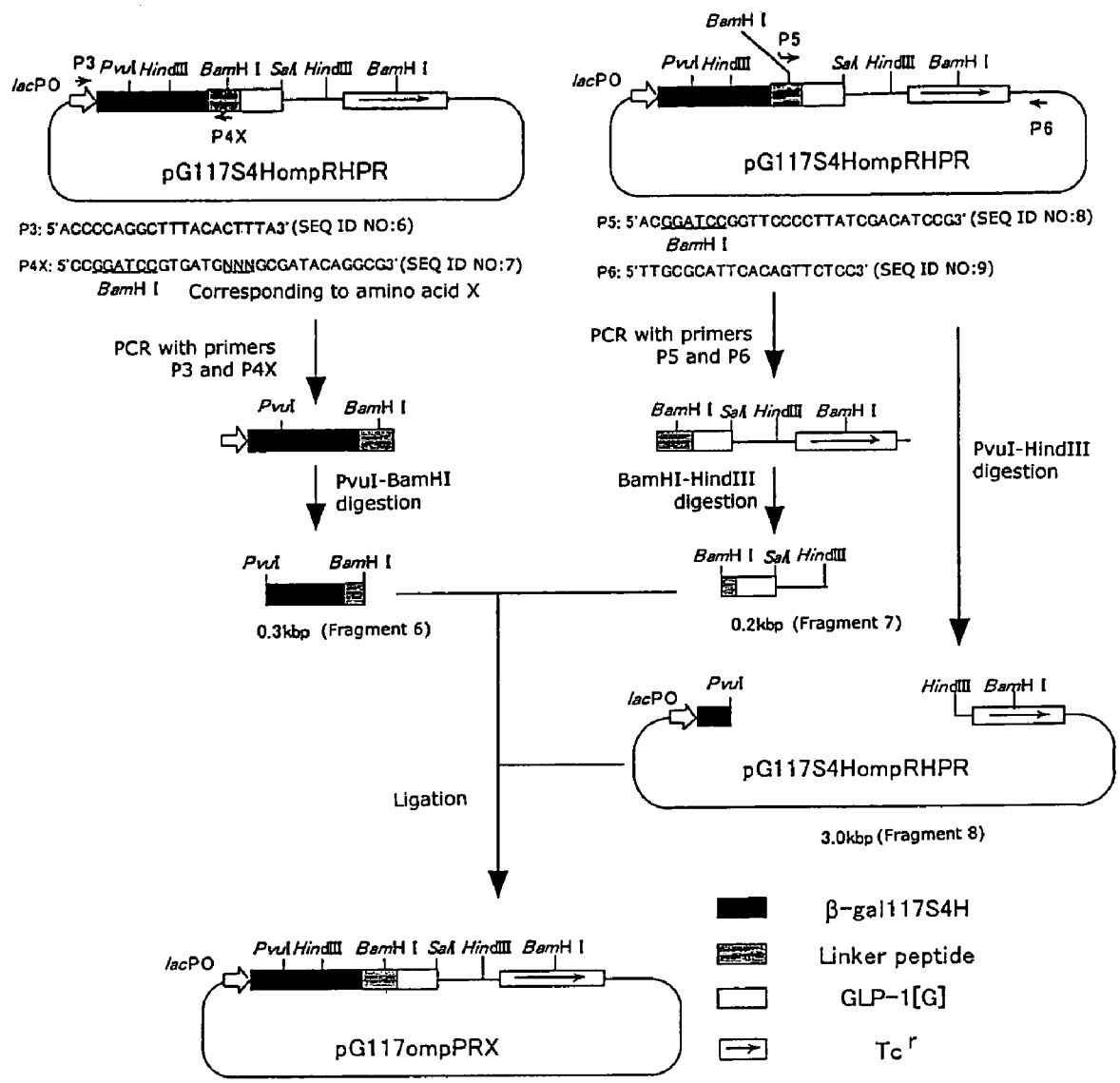
FIG. 5 is a diagrammatic illustration of the construction of pG117ompPRX, wherein β-gal117S4H represents a region encoding a protective protein derived from the N-terminal 117 amino acids of *E. coli* β-galactosidase; GLP-1[G] represents a region encoding human glucagon-like peptide-1; Tc^r represents a tetracycline-resistance gene; Linker peptide represents a region encoding an amino acid sequence from glutamine at the 128-position to arginine at the 153-position; and lac PO represents *E. coli* lactose promoter operator gene.

(4) Step 4: Construction of pG117ompPRX (FIG. 5)

The OmpT protease cleavage site -RLYR↓RHHG- (SEQ ID NO: 1) of the fusion protein PR encoded by pG117S4HompRHPR was converted into -RLYRXHHG- (SEQ ID NO: 2) (wherein X represents an amino acid selected from the 20 types). This conversion was carried out by introducing a mutation into pG117S4HompRHPR.

The mutation was introduced by PCR by using pG117S4HompRHPR as a template. As primers, use was made of P3:5'-ACCCCAGGCTTTACACTTTA-3' (SEQ ID NO: 6) and P4X:5'-CCGGATCCGTGATGNNNGCGATA-CAGGCG-3' (SEQ ID NO: 7) (wherein X represents one letter code of the amino acid (20 types in total); and NNN represents AGC, AAC, CAG, GAT, CGG, GAA, CCA, CAT, GCC, AGA, GGT, GCA, GTA, GTT, CTG, GTC, TTC, TTT, ACG or ATG when conversion into alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine or histidine is intended respectively). The PCR product thus obtained was digested by PvuI and BamHI to give a 0.3 kb fragment (fragment 6). Furthermore, PCR was carried out by using pG117S4HompRHPR as a template and P5:5' ACGGATCCGGTTCCCCTTATCGACATCCG-3' (SEQ ID NO: 8) and P6:5' TTGCGCATTCACAGTTCTCC-3' (SEQ ID NO: 9) as primers. The PCR product thus obtained was digested by BamHI and HindIII to give a 0.2 kbp fragment (fragment 7). These fragments 6 and 7 and a 3.0 kbp fragment (fragment 8) obtained by digesting pG117S4HompRHPR by PvuI and HindIII were ligated so as to carry out transformation. Plasmids were isolated from each clone thus obtained and restriction enzyme analysis and nucleotide sequencing at the mutated site were performed so that it was identified as the expression plasmid of the target fusion protein PRX. These plasmids were collectively referred to as pG117ompPRX (wherein X represents one letter code of the amino acid (20 types in total); namely, a fusion protein having the substitution into alanine is expressed by pG117ompPRA) (FIG. 5).

(5) Step 5: Preparation of Fusion Protein PRX

When pG117ompPRX is expressed in E. coli, the fusion protein PRX (FIG. 6) is expressed as inclusion body. In a case where OmpT protease is expressed in E. coli, the inclusion body is cleaved by OmpT protease merely by dissolving with urea. To avoid the cleavage, therefore, pG117ompPRX was transfected into W3110 M25 (i.e., an OmpT protease-deficient *E. coli* strain) and thus the fusion protein PRX was prepared in the form of inclusion body.

Example 2

Preparation of Purified OmpT Protease Specimen

To prepare purified OmpT protease, the OmpT protease expression plasmid was transfected into an *E. coli* W3110 strain to construct an OmpT protease high-expression *E. coli* strain. From the membrane fraction of this strain, OmpT protease was purified by the following five steps.

Figure 7:
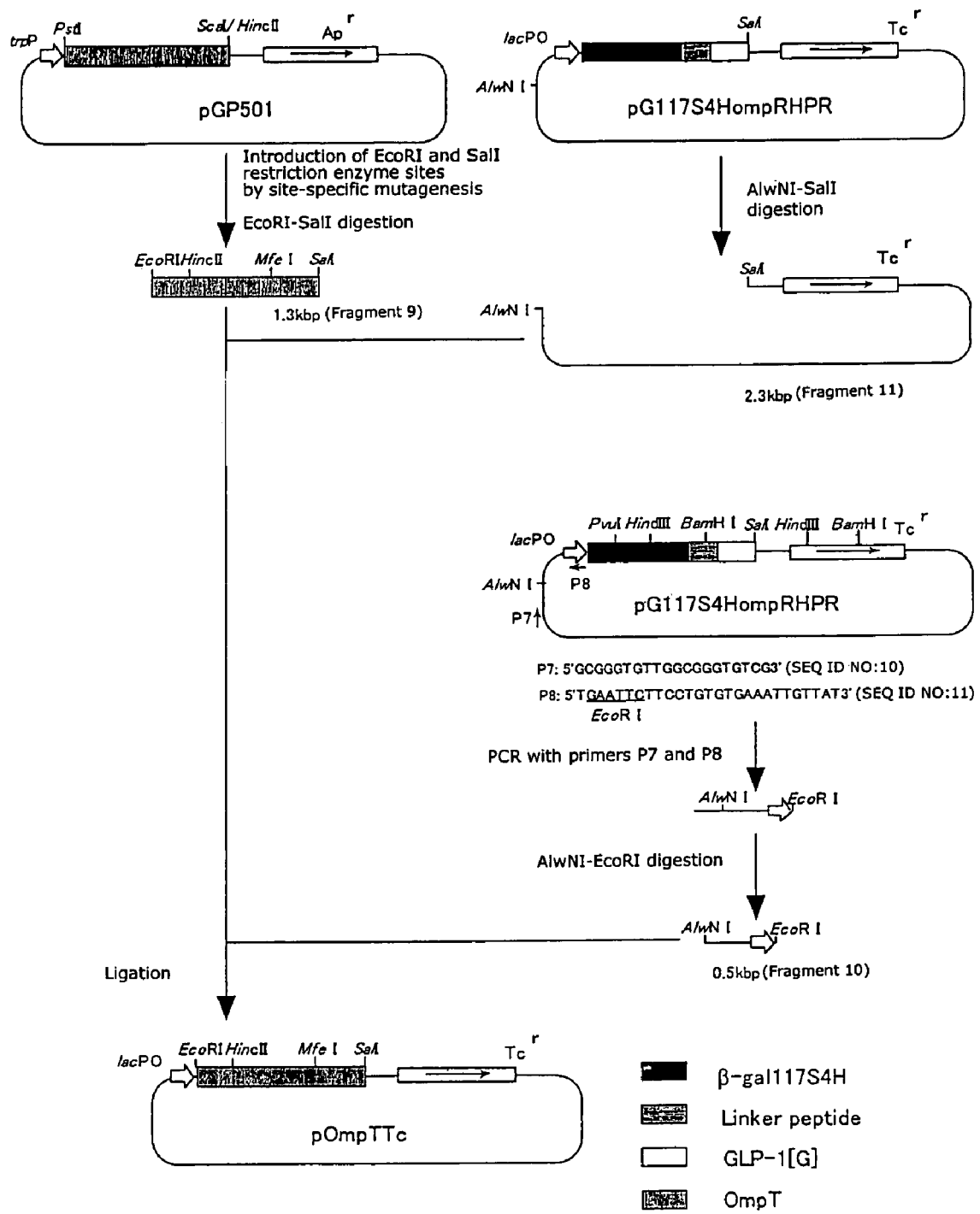
FIG. 7 is a diagrammatic illustration of the construction of pOmpTTc, wherein β-gal117S4H represents a region encoding a protective protein derived from the N-terminal 117 amino acids of *E. coli* β-galactosidase; GLP-1[G] represents a region encoding human glucagon-like peptide-1; Tc^r represents a tetracycline-resistance gene; Ap^r represents an ampicillin-resistance gene; Linker peptide represents a region encoding an amino acid sequence QMHGYDAEL-RLYRRHHGSGSPSRHPR (SEQ ID NO: 64); OmpT represents OmpT protease gene; lac PO represents *E. coli* lactose promoter operator gene; and trpP represents *E. coli* tryptophan promoter gene.

(1) Step 1: Construction of pOmpTTc (FIG. 7)

To enhance the expression level of OmpT protease, an OmpT protease expression plasmid pOmpTTc was constructed. EcoRI- and SalI-restriction enzyme sites were introduced by site-specific mutagenesis respectively into immediately before the translation initiation site and the 3'-end of the OmpT gene in plasmid pGP501 (Sugimura, K. Biochem. Biophys. Res. Commun. 153: 753-759, 1988) containing an OmpT protease gene. By digesting the plasmid by these restriction enzymes, a 1.3 kbp fragment (fragment 9) was obtained.

To introduce an EcoRI restriction enzyme site into the downstream of lac promoter, PCR was carried out by using pG117S4HompRHPR as a template and P7:5'-GCGGGT-GTTGGCGGGTGTCG-3' (SEQ ID NO: 10) and P8:5'-TGAATTCTTCCTGTGTGAAATTGTTAT-3' (SEQ ID NO: 11) as primers. The PCR product thus obtained was digested by EcoRI and AlwNI to give a 0.5 kbp fragment (fragment 10). These fragments 9 and 10 and a 2.3 kbp fragment (fragment 11) obtained from pG117S4HompRHPR by AlwNI and SalI were ligated to thereby construct pOmpTTc.

(2) Step 2: Construction of pOmpTTcB (FIG. 8)

In a method for constructing plasmids showing expression of proteins at high level in *E. coli* (Shunji Natori, Yoshinobu Nakanishi, Zoku Iyakuhinn no Kaihatsu (Sequel To Development of Drugs), vol. 7, 29-61, 1991, Hirokawa Shoten), attempts were made to improve pOmpTTc in the following two points. ① To place the OmpT protease translation initiation site 9 bases down stream of the SD sequence. ② To modify nucleotides so as to minimize the formation of stems or loops in the secondary structure of mRNA between the transcription initiation site and the fifth amino acid from the initiation of OmpT protease translation. After constructing pOmpTTcB (FIG. 8) by the improvement ① and oPmpTTcC (FIG. 9) by the improvement ②, pOmpTTcE (FIG. 10) having been subjected to both of the improvements ① and ② was constructed.

pOmpTTcB with the improvement ① was constructed in the following manner (FIG. 8).

pOmpTTc was digested by HincII and MfeI to give a 1.0 kbp fragment (fragment 12) and pOmpTTc was digested by EcoRI and MfeI to give a 2.9 kbp fragment (fragment 13).

To perform the improvement ①, PCR was carried out by using pOmpTTc as a template and P9:5'-TGAAT-TCAAAATGCGGGCGAAACTGCTGGG-3' (SEQ ID NO: 12) and P10:5'-TGCCGAGGATGACGATGAGC-3' (SEQ ID NO: 13) as primers. The PCR product thus obtained was digested by EcoRI and HincII and the resulted 0.2 kbp fragment (fragment 14) was ligated to the fragments 12 and 13 to thereby construct pOmpTTcB.

(3) Step 3: Construction of pOmpTTcC (FIG. 9)

pOmpTTcC with the improvement ① was constructed in the following manner.

pOmpTTc was digested by EcoRI and SalI to give a 1.3 kbp fragment (fragment 15), and by AlwNI and SalI to give another 2.3 kbp fragment (fragment 16).

To perform the improvement ②, PCR was carried out by using pOmpTTc as a template and P11:5'-CTATCGTCGC-CGCACTTATG-3' (SEQ ID NO: 14) and P12:5'-TGAAT-TCTTCCTGTCTGTAATTTTTATCCGCTCACAATT-3' (SEQ ID NO: 15) as primers. The PCR product thus obtained was digested by EcoRI and AlwNI. The resulted 0.5 kbp fragment (fragment 17) was ligated to the fragments 15 and 16 to thereby construct pOmpTTcC.

(4) Step 4: Construction of pOmpTTcE (FIG. 10)

To improve the expression level of OmpT protease, pOmpTTcE with the improvements of ① and ② was constructed in the following manner.

The 1.3 kbp fragment (fragment 18) obtained by digesting pOmpTTcB by EcoRI and SalI was ligated to a 2.8 kbp fragment (fragment 19) obtained by digesting pOmpTTcC by EcoRI and SalI to thereby construct pOmpTTcE.

(5) Step 5: Preparation of Purified OmpT Protease Specimen

To obtain a purified OmpT protease specimen, pOmpT-TcE was transfected into *E. coli* W3110 strain to thereby give an OmpT protease high expression *E. coli* strain. Next, the OmpT protease high expression *E. coli* strain was cultured in the following manner and OmpT protease was purified.

The W3110/pOmpTTcE strain was incubated under rotation at 37° C. overnight in a 500 ml Erlenmeyer flask with the use of 100 ml of a liquid LB medium containing 10 mg/l of tetracycline. On the next day, it was transferred into an culture vessel equipped with a stirrer containing a medium 21 containing 4 g/l $K_2HPO_4$, 4 g/l $KH_2PO_4$, 2.7 g/l $Na_2HPO_4$, 0.2 g/l $NH_4Cl$, 1.2 g/l $(NH_4)_2SO_4$, 4 g/l yeast extract, 2 g/l $MgSO_4.7H_2O$, 40 mg/l $CaCl_2.2H_2O$, 40 mg/l $FeSO_4.7H_2O$, 10 mg/l $MnSO_4.nH2O$, 10 mg/l $AlCl_3.6H_2O$, 4 mg/l $COCl_2.6H_2O$, 2 mg/l $ZnSO_4.7H_2O$, 2 mg/l $Na_2MoO_4.2H_2O$, 1 mg g/l $CuCl_2.2H_2O$, 0.5 mg/l $H_3BO_4$, 1 g/l glucose, 10 g/l glycerol and 10 mg/l tetracycline and cultivated therein at 37° C. for 12 hours. After the completion of the cultivation, the culture medium was centrifuged (4° C., 6000×g, 10 minutes) to give 80 g of packed cells. These cells were suspended in 600 ml of 50 mM Tris-HCl (pH 7.5) and the suspension was centrifuged (4° C., 6000×g, 10 minutes) to thereby collect the cells. After repeating this procedure, the cells were suspended in 600 ml of 50 mM Tris-HCl (pH 7.5) and disrupted with a Manton-Gorlin. The suspension of the disrupted cells was centrifuged (4° C., 1000×g, 10 minutes) and the precipitate was discarded and the supernatant was recovered. The supernatant was further centrifuged (4° C., 36000×g, 40 minutes). The precipitate was recovered, suspended in 150 ml of 50 mM Tris-HCl (pH 7.5) and centrifuged again (4° C., 36000×g, 40 minutes). To a ⅙ portion of the precipitate thus obtained was added 120 ml of 50 mM Tris-HCl (pH 7.5) containing 0.1% salcosyl. After suspending, the mixture was shaken at 110° C. for 1 hour. After 1 hour, it was centrifuged (4° C., 36000×g, 40 minutes) and the precipitate was recovered. Further, it was suspended in 120 ml of 50 mM Tris-HCl containing 0.1% of Triton X-100 and 5 mM of EDTA and shaken at room temperature for 1 hour. Next, it was centrifuged (4° C., 36000×g, 40 minutes) and the supernatant was recovered to give a crude enzyme specimen.

120 ml of this crude enzyme specimen was applied onto Benzamidine Sepharose 6B Column (12 mm in diameter×70 mm, 8 ml) having been equilibrated with 50 mM Tris-HCl (pH 7.5) containing 0.1% Triton X-100 (hereinafter referred to as the buffer A) at a flow rate of 4 ml/min and then washed with 80 ml of the buffer A. Then the column was eluted with the buffer A containing 0.3 M NaCl and the eluate was taken up in 10 ml portions to give 8 fractions in total.

The fifth fraction, which was proved as being homogeneous by 16% SDS-PAGE, was referred to as a purified OmpT protease specimen. When determined by using a Coomassie Plus Protein Assay Reagent (manufactured by PIERCE) and bovine serum albumin as a standard, the protein concentration of the purified OmpT protease specimen was 120 µg/ml. The OmpT protease activity measured by using Dynorphine A as a substrate was 40 U/ml.

Example 3

Cleavage of PRX by OmpT Protease

It was examined whether or not the fusion protein PRX (FIG. 6), which was constructed by substituting the amino acid at the +1-position (141-position from the N-terminus) of the fusion protein PR having a structure cleavable by OmpT protease (FIG. 4), was cleaved by OmpT protease. PRX was reacted with the purified OmpT protease specimen at pH 7.0 for 30 minutes at 25° C. After the enzymatic reaction, SDS-PAGE analysis was performed. FIG. 11 shows the results wherein – represents a lane free from OmpT protease, and + represents a lane of fusion protein treated with OmpT protease.

In PRD and PRE, no cleavage by OmpT protease was observed (FIG. 11, lanes D and E). In contrast, cleavage by OmpT protease was observed in the proteins other than PRD and PRE.

To identify the cleavage site, peptide digestion products obtained after the OmpT protease treatment were isolated by HPLC and the N-terminal amino acid sequences were determined. The OmpT protease cleavage sites thus identified are listed in Table 1.

TABLE 1

| OmpT protease cleavage site of fusion protein PRX | |
|---|---|
| PRX | Cleavage site |
| PRA | LYR↓AHHGSG (SEQ ID NO:16) |
| PRV | LYR↓VHHGSG (SEQ ID NO:17) |
| PRL | LYR↓LHHGSG (SEQ ID NO:18) |
| PRI | LYR↓IHHGSG (SEQ ID NO:19) |
| PRP | LYRPHHGSG (SEQ ID NO:20) |
| PRF | LYR↓FHHGSG (SEQ ID NO:21) |
| PRW | LYR↓WHHGSG (SEQ ID NO:22) |
| PRM | LYR↓MHHGSG (SEQ ID NO:23) |
| PRG | LYR↓GHHGSG (SEQ ID NO:24) |
| PRS | LYR↓SHHGSG (SEQ ID NO:25) |
| PRT | LYR↓THHGSG (SEQ ID NO:26) |
| PRC | LYR↓CHHGSG (SEQ ID NO:27) |
| PRY | LYR↓YHHGSG (SEQ ID NO:28) |
| PRN | LYR↓NHHGSG (SEQ ID NO:29) |
| PRQ | LYR↓QHHGSG (SEQ ID NO:30) |
| PRD | LYRDHHGSG (SEQ ID NO:31) |
| PRE | LYREHHGSG (SEQ ID NO:32) |

TABLE 1-continued

| OmpT protease cleavage site of fusion protein PRX | |
|---|---|
| PRX | Cleavage site |
| PRK | LYR↓KHHGSG (SEQ ID NO:33) |
| PRR | LYR↓RHHGSG (SEQ ID NO:34) |
| PRH | LYR↓HHHGSG (SEQ ID NO:35) |

↓ stands for an OmpT protease cleavage site. The region from leucine at the 138-position (from the N-terminus) to glycine at the 146-position in the fusion protein PRX is shown as the amino acid sequence at the cleavage site.

In PRP, cleavage was observed not at -RX- but exclusively at -ELR↓LYRPHHG- (SEQ ID NO: 126). In all of the proteins other than PRD, PRE and PRP, however, cleavage was observed at R↓X- (Table 1). Based on these results, it is assumed that amino acid sequences having one of the 17 amino acids [namely, those other than aspartic acid and glutamic acid (acidic amino acids) and proline (an imino acid)] at the +1-position are cleavable by OmpT protease.

Example 4

Preparation of Fusion Protein PKX

Similarly, to examine whether or not the cleavage by OmpT protease can be performed after substituting the amino acid at the +1-position by one of the amino acids other than aspartic acid and glutamic acid (acidic amino acids) and proline also in the case when the OmpT protease cleavage site has a lysine as the basic amino acid at the −1-position, PKX wherein -RLYRXHHG- (SEQ ID NO: 2) of the fusion protein PRX was converted into -RLYKXHHG-, (SEQ ID NO: 36) was constructed (FIG. 13). In the following example, X was selected from alanine, serine, lysine, arginine, aspartic acid and glutamic acid (represented in one letter code of each amino acid). Among these amino acids, lysine and arginine, which formed a basic amino acid pair, were employed as a positive control. Alanine and serine were employed because they showed relatively high cleavage efficiency in Example 3. Aspartic acid and glutamic acid were employed to examine whether PKD and PKE were cleavable or not, since PRD and PRE containing these amino acids were not cleavable.

The fusion protein PKX was prepared by the following two steps.

(1) Step 1: Construction of pG117ompPKX (FIG. 12)

The plasmid pG117ompPKX (wherein X is A, S, K, R, D or E) (FIG. 12) encoding the fusion protein PKX (wherein X is A, S, K, R, D or E) (FIG. 13) was formed in the following manner.

The conversion of -RLYRXHHG- (SEQ ID NO: 2) into -RLYKXHHG- (SEQ ID NO: 36) (wherein X is A, S, K, R, D or E) was conducted by PCR. PCR was carried out by using pG117ompPRA, pG117ompPRS, pG117ompPRK, pG117ompPRR, pG117ompPRD and pG117ompPRE as templates and P3:5'-ACCCCAGGCTTTACACTTTA-3' (SEQ ID NO: 6) and P13X:5'-CCGGATCCGTGAT-GNNNTTTATACAGGCG-3' (SEQ ID NO: 37) as primers (NNN: AGC in case of using pG117ompPRA as a template; AGA in case of using pG117ompPRS; TTT in case of using pG117ompPRK; ACG in case of using pG117ompPRR; GTC in case of using pG117ompPRD; and TTC in case of using pG117ompPRE). A 0.3 kbp fragment (fragment 20) obtained by digesting the PCR product obtained above by PvuI and BamHI was ligated to a 0.1 kbp fragment (fragment 21) obtained by digesting pG117ompPRR by BamHI and SalI and a 3.1 kbp fragment (fragment 22) obtained by pG117ompPRR by PvuI and SalI, and transformation was carried out. The plasmids were isolated from each clone thus obtained and restriction enzyme analysis and nucleotide sequencing at the mutated site were performed in order to confirm that the plasmids express the target fusion proteins. These plasmids were collectively referred to as pG117ompPKX (wherein X represents one letter code of the amino acid substituted, for example, pG117ompPKA represents a plasmid with the substitution into alanine). (FIG. 12).

(2) Step 2: Preparation of Fusion Protein PKX

When pG117ompPKX is expressed in *E. coli*, the fusion protein PKX (FIG. 13) is expressed as inclusion body. In a case wherein OmpT protease is expressed in *E. coli*, the inclusion body is cleaved by OmpT protease merely by solubilizing with urea. To avoid this phenomenon, pG117ompPKX was transformed into the OmpT protease-deficient *E. coli* strain W3110 M25 and thus the fusion protein PKX was prepared as inclusion body.

Example 5

Cleavage of PKX by OmpT Protease

It was examined whether or not the fusion protein PKX (FIG. 13) could be cleaved by OmpT protease.

PKX was reacted with the purified OmpT protease specimen at 25° C. for 30 minutes. FIG. 14 shows the results of SDS-PAGE analysis thereof wherein − represents a lane free from OmpT protease; and + represents a lane of fusion protein treated with OmpT protease.

It was confirmed that PKK and PKR employed as positive controls were cleaved by OmpT protease (FIG. 14, lanes KK and KR). Also, PKA and PKS forming no basic amino acid pair were cleaved by OmpT protease (FIG. 14, lanes KA and KS). In contrast, PKD and PKE were not cleaved by OmpT protease (FIG. 14, lanes KD and KE).

To identify the cleavage sites, the peptide digestion products were isolated by HPLC after the OmpT protease treatment and the N-terminal amino acid sequences were then determined. The OmpT protease cleavage sites thus identified are listed in Table 2.

PKK, PKR, PKA and PKS, which was cleaved by OmpT protease, showed cleavage at -K↓X- (Table 2).

TABLE 2

OmpT protease cleavage site of fusion protein PKX

| PKX | Cleavage site |
|---|---|
| PKA | LYK↓AHHGSG (SEQ ID NO:38) |
| PKS | LYK↓SHHGSG (SEQ ID NO:39) |
| PKK | LYK↓KHHGSG (SEQ ID NO:40) |
| PKR | LYK↓RHHGSG (SEQ ID NO:41) |
| PKD | LYKDHHGSG (SEQ ID NO:42) |
| PKE | LYKEHHGSG (SEQ ID NO:43) |

↓ stands for an OmpT protease cleavage site. The region from leucine at the 138-position (from the N-terminus) to glycine at the 146-position in the fusion protein PKX is shown as the amino acid sequence at the cleavage site.

Accordingly, the results of Examples 3 and 5 indicate that there exist OmpT protease cleavage sites not only in the case of basic amino acid pairs (-RR-, -RK-, -KR- and -KK-) but also in the case of pairs including one basic amino acid (-RX-, -KX-). When X is aspartic acid or glutamic acid (an acidic amino acid) or proline (an imino acid), however, no cleavage arises in this site.

Example 6

Preparation of Fusion Proteins PRhANP and PRhCT

The results of Example 3 indicated that OmpT protease can cleave -R↓X- (wherein X represents an amino acid (17 types in total) other than aspartic acid, glutamic acid (acidic amino acids) and proline) in the amino acid sequences in the vicinity of the OmpT protease cleavage sites shown in Example 3. Also, similar results were obtained concerning the cleavage at -K↓X- in Example 5.

With respect to the recognition of substrate by this enzyme, however, it seems insufficient to merely examine on the amino acid sequences reported hitherto and the amino acid sequences in the vicinity of the cleavage sites (i.e., in the N- and C-terminal sides) are also important. In the above Examples, the present inventors substituted the amino acid at the +1-position of the cleavage site by this enzyme. In view of the fact that the amino acid sequences in the vicinity of the cleavage sites might be important in the substrate recognition and cleavage, the present inventors further examined how the cleavage by OmpT protease occurred in the case of the target peptide moiety of the fusion proteins employed into Examples 3 and 5 was substituted with other peptides (i.e., altering the amino acid sequence in the C-terminal side from the amino acid at the +1-position).

A fusion protein PRhANP (FIG. 16), wherein α-hANP (β-type human atrial natriuretic peptide) was arranged following arginine at the 140-position from the N-terminus of the fusion protein PR (FIG. 4), and another fusion protein PRhCT (FIG. 18), wherein hCT[G] (human calcitonin precursor) was provided, were constructed and reacted with OmpT protease so as to examine whether or not (α-hANP and hCT[G] could be excised.

An expression plasmid pG117ompPRhANP of the fusion protein PRhANP and an expression plasmid of pG117ompPRhCT of the fusion protein PRhCT were constructed by using pG118ompPRR (FIG. 5). The fusion proteins PRhANP and PRhCT were prepared by the following three steps.

(1) Step 1: Construction of pG117ompPRhANP (FIG. 15)

The expression plasmid pG117ompPRhANP of the fusion protein PRhANP (FIG. 16), wherein α-hANP was arranged following arginine at the 140-position of the N-terminus of the fusion protein PR (FIG. 4), was constructed. PCR was carried out by using pGHα97II ("Daichokin o shukushu toshita seirikassei peputido seisankei ni kansuru kenkyu (Study on Physiologically Active Peptide Production System with the Use of *E. coli* as Host)", Koji Magota, Doctoral Dissertation, Kyushu University, 1991) as a template P14: 5'-GCGGAGCTCCGCCTGTATCGCAGCCT-GCGGAGATCCAGCTG-3' (SEQ ID NO: 44) and P15:5'-CTGAGTCGACTCAGTACCGG-3' (SEQ ID NO: 45) as primers. The PCR product thus obtained was isolated and digested by SacI and SalI. The 0.1 kbp fragment (fragment 23) thus obtained was ligated to a 3.4 kbp fragment (fragment 24) obtained by digesting pG117ompPRR by SacI and SalI and transformation was performed. A plasmid was isolated from each clone thus obtained and restriction enzyme analysis and nucleotide sequencing at the mutated site were performed so that it was identified as the expression plasmid of the target fusion protein. This plasmid was referred to as pG117ompPRhANP.

(2) Step 2: Construction of pG117ompPRhCT (FIG. 17)

An expression plasmid pG117ompPRhCT of the fusion protein PRhCT (FIG. 18) wherein hCT[G] was arranged following arginine at the 140-position from the N-terminus of the fusion protein PR (FIG. 4) was constructed. PCR was carried out by using pG97S4DhCT[G]R4 (Yabuta, M., Suzuki, Y. and Ohsuye, K. Appl. Microbiol. Biotechnol. 42: 703-708, 1995) as a template and P16:5'-GCGGAGCTC-CGCCTGTATCGCTGTGGTAACCTGAGCACCTG-3' (SEQ ID NO: 46) and P17:5'-CTGAGTCGACTTAGC-CCGGG-3' (SEQ ID NO: 47) as primers. The PCR product thus obtained was digested by SacI and SalI. The 0.1 kbp fragment (fragment 25) thus obtained was ligated to a 3.4 kbp fragment (fragment 26) obtained by digesting pG117ompPRR using SacI and SalI and transformation was carried out. The plasmid was isolated from each clone thus obtained, and the restriction enzyme analysis and the nucleotide sequencing at the mutated site were performed so that it was identified as the expression plasmid of the target fusion protein. This plasmid was referred to as pG117ompPRhCT.

(3) Step 3: Preparation of Fusion Proteins PRhANP and PRhCT pG117ompPRhANP and pG117ompPRhCT prepared above were transformed into the OmpT protease-deficient *E. coli* strain W3110 M25 to thereby give fusion protein-producing strains. By cultivating these strains, the fusion proteins PRhANP (FIG. 16) and PRhCT (FIG. 18) were prepared as an inclusion body.

Example 7

Cleavage of PRhANP and PRhCT by OmpT Protease

It was examined whether or not the fusion proteins PRhANP (FIG. 16) and PRhCT (FIG. 18) could be cleaved by OmpT protease.

PRhANP and PRhCT were reacted with the purified OmpT protease specimen at 25° C. for 30 minutes at pH 7.0. The FIG. 19 shows the results of SDS-PAGE analysis wherein − represents a lane free from OmpT protease; and + represents a lane with the addition of OmpT protease. As a result, PRhANP was cleaved by OmpT protease (FIG. 19, lane α-hANP), while PRhCT was not cleaved thereby (FIG. 19, lane hCT).

Furthermore, in order to identify the cleavage site of PRhANP, the peptide digestion product after the OmpT protease treatment was isolated by HPLC and the N-terminal amino acid sequence was determined. Thus, it was confirmed that α-hANP had been excised.

Taking the results of this Example into consideration, it is obvious that α-hANP having serine as the N-terminal amino acid was excised from the fusion protein employed, while hCT[G] having cysteine as the N-terminal amino acid was not cleaved. In the results of Example 3, PRC having cysteine at the +1-position could be cleaved by OmpT protease but hCT[G] was not cleaved. Therefore, it has been confirmed that the cleavage by this enzyme does not depend merely on the amino acid sequence at the −1- and +1-positions of the cleavage site but is largely affected by the amino acid sequence in the vicinity of the cleavage site.

Example 8

Preparation of Fusion Protein RShANP

The fusion protein RShANP (FIG. 21) encoded by the expression plasmid pGRShANP (FIG. 20) is a fusion protein wherein β-gal97S originating in 97 amino acids from the N-terminus of *E. coli* β-galactosidase, serving as a protective protein, is ligated to α-hANP via a linker consisting of three amino acids (glutamine-phenylalanine-arginine). In the course of studies on OmpT protease, the present inventors found out that the fusion protein RShANP is cleaved by OmpT protease at the bond between arginine in the linker sequence and serine at the N-terminus of (α-hANP. The fusion protein RShANP was prepared by the following two steps.

(1) Construction of pGRShANP (FIG. 20)

The pGHα97 μl is a plasmid constructed as a β-gal97S/α-hANP fusion protein expression plasmid. A plasmid pGR-ShANP expressing the fusion protein RShANP, wherein lysine located immediately before the N-terminal serine of the fusion protein x-hANP expressed by pGHα97II was converted into arginine, was constructed in the following manner.

PCR was carried out by pGHα97SII as a template and P18:5'-TACGATGCGCAATTCCGTAGCCTGCGG-3' (SEQ ID NO: 48) and P19:5'-TGCCTGACTGCGTTAG-CAATTTAACTGTGAT-3' (SEQ ID NO: 49) as primers and thus 0.2 kbp PCR product (P20) wherein lysine located as the amino acid codon immediately before the N-terminal serine of α-hANP had been converted into arginine was obtained.

Then, PCR was carried out again by using the thus obtained PCR product (P20) and P21:5'-TTATCGC-CACTGGCAGCAGC-3' (SEQ ID NO: 50) as primers and pGHα97 μl as a template to thereby give a 1.0 kbp PCR product containing a linker DNA sequence with the substitution by arginine. This 1.0 kbp PCR product was digested by BglII and EcoRI and thus a 0.2 kbp DNA fragment (Fragment 27) was isolated. The α-hANP expression plasmid pGHα97SII was digested by BglII and EcoRI and the 3.0 kbp fragment (fragment 28) thus obtained was ligated to the fragment 27, thereby constructing pGRShANP.

(2) Step 2: Preparation of Fusion Protein RShANP

When pGRShANP is expressed in *E. coli*, the fusion protein RShANP (FIG. 21) is expressed as inclusion body. In a case wherein OmpT protease is expressed in *E. coli*, the inclusion body is cleaved by OmpT protease merely by solubilizing with urea. To avoid this phenomenon, pGRS-hANP was transformed into the OmpT protease-deficient *E. coli* strain W3110M25 and thus the fusion protein RShANP was prepared as an inclusion body.

Example 9

Cleavage of RShANP by OmpT Protease

The physiologically active peptide α-hANP was excised from the fusion protein RShANP (FIG. 21) in the following manner. RShANP was reacted with OmpT protease at pH7.0 at 37° C. for 2 hours followed by SDS-PAGE analysis. The result is shown in FIG. 24 (lane RS) wherein − represents a lane free from OmpT protease; and + represents a lane with the addition of OmpT protease. Based on this result, it was confirmed that RShANP could be cleaved by OmpT protease. To identify the cleavage site, the peptide digestion product obtained after the OmpT protease reaction was isolated by HPLC and the N-terminal amino acid sequence was determined. The OmpT protease cleavage site thus identified is listed in Table 3 (RShANP). As Table 3 shows, RShhANP was cleaved by OmpT protease at -AQFR↓SLRR- and thus the physiologically active peptide α-hANP was directly excised. Also, cleavage at -AQFRSLR↓R- was partly detected and the excision of α-hANP(3-28) was also confirmed.

TABLE 3

OmpT protease cleavage sites of fusion proteins RShANP and RXhANP

| RXhANP | Cleavage site |
| --- | --- |
| RShANP | QFR↓SLRRS (SEQ ID NO:52) |
| RRhANP | QFR↓RLRRS (SEQ ID NO:53) |
| RAhANP | QFR↓ALRRS (SEQ ID NO:54) |
| RChANP | QFR↓CLRRS (SEQ ID NO:55) |

↓ stands for an OmpT protease cleavage site. The region from glutamine at the 99-position (from the N-terminus) to serine at the 106-position in the fusion protein RShANP or RXhANP is shown as the amino acid sequence at the cleavage site.

Example 10

Preparation of Fusion Protein RXhANP

In case of using the fusion protein PRX as a substrate, it was confirmed that the amino acid sequence -RLYRXHHG- (SEQ ID NO: 2) (wherein X represents an amino acid selected from the types) having as X an amino acid other than aspartic acid and glutamic acids (i.e., acidic amino acids) and proline (i.e., an imino acid) was cleavable by OmpT protease. Thus, it was examined whether or not cleavage similar to PRX arose in the OmpT protease cleavage site of other amino acid sequences. First, an expression plasmid pGRXhANP (wherein X is R, A or C) of the fusion protein RXhANP (wherein X is R, A or C), which had been constructed by transferring mutation into the expression plasmid pGRShANP (FIG. 20) to thereby convert the OmpT protease cleavage site -AQFR↓SLRR- (SEQ ID NO: 125) into -AQFRXLRR- (SEQ ID NO: 56) (wherein X is arginine, alanine or cysteine), was constructed (FIG. 22). With respect to X, arginine was selected as a positive control forming a basic amino acid pair. Alanine and cysteine were selected because they provided relatively high cleavage efficiency in Example 3. RXhANP (FIG. 23) was constructed by the following two steps.

(1) Step 1: Construction of pGRXhANP (FIG. 22)

pGRXhANP was constructed by introducing a mutation into pGRShANP. pGRShANP was employed as a template, while P3:5'-ACCCCAGGCTTTACACTTTA-3' (SEQ ID NO: 6) and P22X:5'-TCTCCGCAGNNNACGGAAT-TGCGCATCGTA-3' (SEQ ID NO: 57) (NNN: AGC in case of converting into alanine; GCA in case of converting the resine into cysteine; and ACG in case of converting into arginine) were employed as primers. From the PCR product thus obtained, the target PCR product was isolated (PCR product 29). Similarly, PCR was carried out by using pGR-ShANP as a template and P23X:5'-CAATTCCGTNNNCT-GCGGAGATCCAGCTGC-3' (SEQ ID NO: 58) (NNN: GCT in the case of converting into alanine; TGC in the case of converting into cysteine; and CGT in the case of converting into arginine) and P24:5'-GCCTGACTGCGTTAG-CAATTTAACTGTGAT-3' (SEQ ID NO: 59) as primers and the target PCR product (PCR product 30) was isolated. PCR was carried out by using the PCR products 29 and 30 obtained above as templates and P3:5'-ACCCCAGGCTT-TACACTTTA-3' (SEQ ID NO: 6) and P24:5'-GCCTGACT-GCGTTAGCAATTTAACTGTGAT-3' (SEQ ID NO: 59) as primers. The PCR product was collected and digested by EcoRI and BglII to thereby isolate a 0.2 kbp DNA fragment (fragment 31). This fragment 31 was ligated to a 3.0 kbp fragment (Fragment 32), which had been obtained by digesting pGRShANP with EcoRI and BglII, and transformation was performed. A plasmid was isolated from each clone thus obtained and restriction enzyme analysis and nucleotide sequencing at the mutated site were performed so that it was identified as the expression plasmid of the target fusion protein. This plasmid was referred to as pGRXhANP (wherein X represents one letter code of the amino acid converted; namely, a fusion protein having substitution into alanine is expressed as pGRAhANP).

(2) Step 2: Preparation of Fusion Protein RXhANP

When pGRXhANP is expressed in E. coli, the fusion protein RXhANP (FIG. 23) is expressed as inclusion body. In a case where OmpT protease is expressed in E. coli, the inclusion body is cleaved by OmpT protease merely by dissolving with urea. To avoid this phenomenon, therefore, pGRXhANP was transformed into the OmpT protease-deficient E. coli strain W3110 M25 and thus the fusion protein RXhANP was prepared in the form of inclusion body.

Example 11

Cleavage of RXhANP by OmpT Protease

The fusion protein RXhANP (FIG. 23), wherein the OmpT protease -AQFR↓SLRR- of the fusion protein RShANP (FIG. 21) had been converted into -AQFRXLRR- (wherein X is arginine, alanine or cysteine) was treated with OmpT protease at pH7.0, 37° C. for 2 hours. FIG. 24 shows the result of SDS-PAGE analysis.

Similarly to the cases of using PRR, PRA and PRC as a substrate, cleavage by OmpT protease was observed in RRhANP, RAhANP and RChANP. To identify the cleavage sites, the peptide digestion products were isolated by HPLC after the OmpT protease treatment and the N-terminal amino acid sequences were determined. The OmpT protease cleavage sites thus identified are listed in Table 3. As Table 3 shows, RRhANP, RAhANP and RChANP were each cleaved by OmpT protease at -AQFRK↓XLRR-. Furthermore, taking the results in the fusion protein PRX into consideration too, it is suggested that there exist OmpT protease cleavage sites comprising one basic amino acid in the case wherein the amino acid sequence in the vicinity the OmpT protease cleavage site is altered.

In this Example, arginine-arginine alone was slightly cleaved, among the four sites (arginine-arginine, arginine-methionine, arginine-isoleucine and arginine-tyrosine) existing in α-hANP molecule consisting of 28 amino acids, while the other bonds were scarcely cleaved. These facts suggest that the cleavage sequences reported hitherto and the sequences proposed by the present inventors (i.e., arginine-X or lysine-X wherein X is one of the 17 amino acids other than aspartic acid and glutamic acid (acidic amino acids) and proline (an imino acid)) alone are not sufficient to be cleaved by OmpT protease. That is to say, it is indicated that a method for creating a novel cleavage site by utilizing a region containing the known cleavage sites of this enzyme, as performed by the present inventors, is industrially useful.

Example 12

Preparation of Fusion Protein PRRXA

As described above, it is pointed out that OmpT protease cleaves the central bond of arginine-X or lysine-X wherein X is one of the 17 amino acids other than aspartic acid and glutamic acid (acidic amino acids) and proline (an imino acid). However, OmpT protease does not always cleave all of these bonds in proteins and peptides. It is estimated that the cleavage by OmpT protease is largely affected by the amino acid sequences in the vicinity of the cleavage sites. It is rather considered that this enzyme has high substrate specificity because it cleaves exclusively specific sites. The present inventors expected that the substrate specificity of this enzyme might be further clarified by examining the effect of the amino acid sequence in the N-terminal side of the known cleavage site of the enzyme and, therefore, conducted the following experiment.

The fusion protein PRR (shown in FIG. 25) having a structure cleavable by OmpT protease consists of a protective protein (β-gal117S4H) originating in 117 amino acids from the N-terminus of *E. coli* β-galactosidase and human glucagon-like peptide-1 (GLP-1[G]). As shown in FIG. 25, a fusion protein PRRXA (wherein X corresponds to the position of the amino acid of the cleavage site and represented in −1, −2 - - - −10 excluding −7), wherein an amino acid in the amino acid sequence at the −10- to −1-positions (i.e., GYDAELRLYR) (SEQ ID NO: 79) of the OmpT protease cleavage site -QMHGYDAELRLYR↓RHHG- (SEQ ID NO: 78) existing in the linker peptide of the fusion protein PRR had been converted one by one into alanine, was prepared and the cleavage of these fusion proteins by OmpT protease was examined.

The fusion protein PRRXA was prepared by the following two steps.

(Step 1) Construction of pG117ompPRRXA (FIGS. 26, 27, 28, 29)

The expression plasmid of the fusion protein PRRXA was referred to as pG117ompPRRXA (corresponding to the fusion protein PRRXA). However, alanine at the −7-position was not substituted. These substitutions were carried out by introducing DNA mutations info pG117ompPRR.

The PCR method was employed in order to induce mutation. As shown in FIG. 26, the plasmids pG117ompPRR-2A, pG117ompPRR-3A and pG117ompPRR-4A were constructed by using pG117ompPRR as a template and P10: 5'-TGCCGAGGAT-GACGATGAGC-3' (SEQ ID NO: 13), P25: 5'-GCG-GAGCTCCGCCTGGCTCGCCGTCATCAC-3', (SEQ ID NO: 80) P26: 5'-GCGGAGCTCCGCGCTTATCGCCGT-CATCAC-3' (SEQ ID NO: 81) and P27: 5'-GCG-GAGCTCGCTCTGTATCGCCGTCATCAC-3' (SEQ ID NO: 82) as primers. The PCR products obtained by using the combinations of the primers P10/P25, P10/P26 and P10/P27 were digested by SacI and KpnI to give each 0.1 kbp fragment (fragment 33) in each combination. Separately, pG117omoPRR was digested by BglII and SacI to give a 0.2 kbp fragment (fragment 34). These fragments 33 and 34 were ligated to a 3.2 kbp fragment (fragment 35) obtained by digesting pG117ompPRR by BglII and KpnI and transformation was carried out. A plasmid was isolated from each clone thus obtained.

As shown in FIG. 27, expression plasmids pG117ompPRR-5A and pG117ompPRR-6A were constructed by using the pG117ompPRR as a template and P10, P28: 5'-CAGATGCATGGTTATGACGCGGAGGCTCGC-3', (SEQ ID NO: 83) and P29: 5'-CAGATGCATGGTTAT-GACGCGGCTCTCCGC-3' (SEQ ID NO: 84) as primers. The PCR product obtained by using the combinations of the primers P10/P28 and P10/P29 was digested by NsiI and KpnI to give a 0.1 kbp fragment (fragment 36) in each combination. Separately, pG117ompPRR was digested by NsiI and KpnI to give a 3.4 kbp fragment (fragment 37). These fragments 36 and 37 were ligated together and transformation was carried out. A plasmid was isolated from each clone thus obtained.

Further, expression plasmids pG117ompPRR-8A, pG117ompPRR-9 and pG117ompPRR-10A were constructed as shown in FIG. 28. pG117ompPRR was used as a template and P3: 5'-ACCCCAGGCTTTACACTTTA-3' (SEQ ID NO: 6) P30: 5'-GCGGAGCTCCGCAGCATAAC-CATGCATCTG-3', (SEQ ID NO: 85) P31: 5'-GCG-GAGCTCCGCGTCAGCACCATGCATCTG-3' (SEQ ID NO: 86) and P32: 5'-GCGGAGCTCCGCGTCATAAGCAT-GCATCTG-3' (SEQ ID NO: 87) were used as primers. The PCR products obtained by the combinations of the primers P3/P30, P3/P31 and P3/P32 were digested by SacI and BglII to give a 0.2 kbp fragment (fragment 38) in each combination. Separately, pG117ompPRR was digested by KpnI and SacI to give a 0.1 kbp fragment (fragment 39). These fragments 38 and 39 were ligated to a 3.2 kbp fragment (fragment 40) obtained by digesting pG117ompPRR with BglII and KpnI and transformation was carried out. A plasmid was isolated from each clone thus obtained. pG117ompPRR-1A was constructed as shown in FIG. 29 by using pG117ompPRR as a template and P10 and P33: 5' GCGGAGCTCCGCCTGTATGCTCGTCATCAC-3' (SEQ ID NO: 88) as primers. The PCR product obtained by the combination of the primers P10/P33 was digested by SacI to give a 0.1 kbp fragment (fragment 41). Separately, pG117ompPRR was digested by Sac to give a 3.4 kbp fragment (fragment 42). These fragments 41 and 42 were ligated together and transformation was carried out. A plasmid was isolated from each clone thus obtained.

These expression plasmids pG117ompPRRXAs thus constructed were all subjected to restriction enzyme analysis and nucleotide sequencing at the mutation site and thus confirmed as being the expression plasmids of the target fusion proteins PRRXAs.

(Step 2) Preparation of Fusion Proteins PRR and PRRXA

When pG117ompPRR and pG117ompPRRXA are expressed in *E. coli*, the fusion proteins PRR and PRRXA are expressed as inclusion bodies. In a case where OmpT protease is expressed in *E. coli*, the inclusion body is cleaved by OmpT protease merely by dissolving with urea. To avoid the cleavage, therefore, pG117ompPRR and pG117ompPRRXA were transformed into the OmpT protease-deficient *E. coli* strain W3110M25 and thus the fusion proteins PRR and PRRXA were prepared in the form of inclusion body.

Example 13

Cleavage of Fusion Proteins PRR and PRRXA by OmpT Protease

PRR and PRRXA were reacted with the purified OmpT protease specimen at 25° C. for 60 minutes at pH 7.0. After the completion of the enzymatic reaction, SDS-PAGE analysis was carried out. The results are shown in FIG. 30.

The PRR-1A was not cleaved by OmpT protease (FIG. 30, lane 1A). Although the cleavage by OmpT protease was confirmed in the fusion proteins other than PRR-1A, the amount of the 4.9 kDa peptide fragment formed by the cleavage differed from protein to protein.

In order to quantitate the 4.9 kDa peptide fragment, the liquid reaction mixture of the above-described OmpT protease reaction was subjected to HPLC. In the OmpT protease reaction of each of the fusion proteins other than PRR-1A, a peak was detected at a retention time of 8.8 minutes. The N-terminal amino acid sequence of this peak at 8.8 minutes detected in PRR had been determined and it had been clarified as a 4.9 kDa peptide fragment formed by the cleavage at -QMHGYDAELRLYR↓RHHG- (Table 4) (SEQ ID NO: 78). Thus, it is assumed that the peak at 8.8 minutes formed by reacting each fusion protein with OmpT protease corresponds to the 4.9 kDa peptide fragment.

The relative peak area at the retention time of 8.8 minutes indicates the amount of the 4.9 kDa peptide fragment formed by the cleavage. Table 4 shows the data of the relative amounts of the 4.9 kDa peptide fragment calculated by referring the amount in the case of PRR as to 100. Excluding PRR-1A, PRR-4A showed the smallest amount of the 4.9 kDa peptide fragment and PRR-6A showed the largest one. Based on these results, it is considered that the −4- and −6-positions (other than −1-position) largely affect the cleavage by OmpT protease.

TABLE 4

Cleavage of fusion protein PRRXA (X ranging from −10- to −1, excluding −7)

| PRRXA | Relative amount of 4.9 kDa peptide |
| --- | --- |
| PRR | 100 |
| PRR-1A | ND |
| PRR-2 | 150 |
| PRR-3A | 44 |
| PRR-4A | 24 |
| PRR-5A | 89 |
| PRR-6A | 330 |
| PRR-8A | 200 |
| PRR-9A | 160 |
| PRR-10A | 160 |

The 4.9 kDa peptide is formed by the cleavage of the fusion proteins by OmpT protease.
The amount of the 4.9 kDa peptide of PRR is referred to as 100.
ND means not detectable.

Example 14

Preparation of Fusion Proteins PRR-4X and PRR-6X

The OmpT protease is an endoprotease which recognizes and cleaves mainly basic amino acid pairs. The substrate specificity of mammalian furin, which is also an endoprotease recognizing and cleaving basic amino acid pairs (cleaving the C-terminal side of basic amino acid pairs), has been studied in detail and it is reported that furin recognizes arginine at the −1-position and basic amino acids at the −2-, −4- and −6-positions concerning the cleavage site.

The results of Example 13 indicate that the substitution of arginine which is the basic acid at the −4-position into alanine makes the cleavage by OmpT protease difficult, while the substitution of glutamic acid which is the acidic amino acid at the −6-position into alanine facilitates the cleavage by OmpT protease.

Based on these facts, it was assumed that the cleavage by the OmpT protease might be affected by the charges on the amino acids at the −6- and −4-positions of the cleavage site.

Thus, the cleavage by OmpT protease was examined by forming fusion proteins wherein the amino acids at these positions were substituted by arginine and lysine (basic amino acids), aspartic acid and glutamic acid (acidic amino acids) and asparagine and glutamine (neutral amino acids being similar in structure to acidic amino acids).

A fusion protein with the substitution at the −4-position was referred to PRR-4X (FIG. 31), while a fusion protein with the substitution at the −6-position was referred to PRR-6X (FIG. 32), wherein X represents one letter of the amino acid at the −4- or −6-position. The fusion proteins PRR-4X and PRR-6X were prepared by the following two steps.

(Step 1) Construction of pG117ompPRR-4X and pG117ompPRR-6X (FIGS. 33 and 34)

The expression plasmid of the fusion protein PRR-4X, wherein arginine at the −4-position of the OmpT protease cleavage site -QMHGYDAELRLYR↓RHHG (SEQ ID NO: 78)- of the fusion protein PRR had been substituted by lysine (a basic amino acids), aspartic acid or glutamic acid (an acidic amino acid) or asparagine or glutamine (a neutral amino acid being similar in structure to acidic amino acids), was referred to as pG117ompPRR-4X, while the expression plasmid of the fusion protein PRR-6X, wherein glutamic acid at the −6-position had been substituted in the same manner, as to pG117ompPRR-6X. These substitutions were carried out by introducing DNA mutations into pG117ompPRR.

The mutations were introduced by PCR. Expression plasmids pG117ompPRR-4K, pG117ompPRR-4D, pG117ompPRR-4E, pG117ompPRR-4N and pG117ompPRR-4Qwere were constructed by the procedure shown in FIG. 33. pG117ompPRR was used as a template, while P10, P34: 5'-GCGGAGCTCAAACTGTATCGCCGT-CATCAC-3', (SEQ ID NO: 89) P35: 5'-GCGGAGCTC-GACCTGTATCGCCGTCATCAC-3' (SEQ ID NO: 90) P36: 5'-GCGGAGCTCGAACTGTATCGCCGTCATCAC-3', (SEQ ID NO: 91) P37: 5'-GCGGAGCTCAACCTG-TATCGCCGTCATCAC-3' (SEQ ID NO: 92) and P38: 5'-GCGGAGCTCCAGCTGTATCGCCGTCATCAC-3' (SEQ ID NO: 93) were used as primers. As the PCR products with the use of the combinations of the primers P10/P34, P10/P35, P10/P36, P10/P37 and P10/P38, the 0.3 kbp fragment (fragment 43) was obtained. PCR was carried out again by using pG117ompPRR as a template and P3 and the fragment 43 as primers to give the 0.8 kbp fragment (fragment 44). The 0.1 kbp fragment (fragment 45) obtained by digesting fragment 44 with NsiI and KpnI was ligated to the 3.4 kbp fragment (fragment 46) obtained by digesting pG117ompPRR with NsiI and KpnI, and transformation was carried out. A plasmid was isolated from each clone thus obtained.

As shown in FIG. 34, expression plasmids pG117ompPRR-6R, pG117ompPRR-6K, pG117ompPRR-6D, pG117ompPRR-6N and pG117ompPRR-6Q were constructed by using pG117ompPRR as a template and P10, P39: 5'-CAGATGCATGGTTATGACGCGCGTCTCCGC-3', (SEQ ID NO: 94) P40: 5'-CAGATGCATGGTTAT-GACGCGAAACTCCGC-3', (SEQ ID NO: 95) P41: 5'-CA-GATGCATGGTTATGACGCGGACCTCCGC-3', (SEQ ID NO: 96) P42: 5'-CAGATGCATGGTTATGACGCGAAC-CTCCGC-3' (SEQ ID NO: 97) and P43: 5'-CAGATG-CATGGTTATGACGCGCAGCTCCGC-3' (SEQ ID NO: 98) as primers. The PCR products obtained by using the combinations of the primers P10/P39, P10/P40. P10/P41, P10/P42 and P10/P43 were digested by NsiI and KpnI to give a 0.1 kbp fragment (fragment 46). Further, pG117ompPRR was digested by NsiI and KpnI to give the 3.4 kbp fragment (fragment 47). These fragments 46 and 47 were ligated together and transformation was carried out. A plasmid was isolated from each clone thus obtained and restriction enzyme analysis and nucleotide sequencing at the mutated site were performed. Thus, these plasmids were identified as the expression plasmids pG117ompPRR-4X and pG117ompPRR-6X of the target fusion proteins PRR-4X and PRR-6XX.

(Step 2) Preparation of Fusion Proteins PRR-4X and PRR-6X

When pG117ompPRR-4X and pG117ompPRR-6X are expressed in *E. coli*, the fusion proteins PRR-4X and PRR-6X (FIGS. 31 and 32) are expressed as inclusion body. In a case where OmpT protease is expressed in *E. coli*, these inclusion body is cleaved by OmpT protease merely by dissolving with urea. To avoid the cleavage, therefore, pG117ompPRR-4X and pG117ompPRR-6X were transformed into the OmpT protease-deficient *E. coli* strain W3110M25 and thus the fusion proteins PRR-4X and PRR-6X were prepared in the form of inclusion body.

Example 15

Cleavage of Fusion Proteins PRR-4X and PRR-6X by OmpT Protease

PRR-4X was reacted with the purified OmpT protease specimen at 25° C. for 60 minutes at pH 7.0. After the enzymatic reaction, SDS-PAGE analysis was performed.

FIG. 35A shows the results wherein – represents a lane free from OmpT protease, and +represents a lane with the addition of OmpT protease (2.0 U/ml).

Although the cleavage by OmpT protease was observed in all of the fusion proteins, the amount of the 4.9 kDa peptide fragment formed by the cleavage differed from protein to protein.

Then the 4.9 kDa peptide fragment was quantitated by using HPLC. In the cases of adding OmpT protease, peaks were detected at retention time of 8.8 minutes. As described in Example 13, these peaks are seemingly assignable to the 4.9 kDa peptide fragment.

Table 5 shows the data of the relative amounts of the 4.9 kDa peptide fragment calculated by referring the amount in the case of PRR as to 100. The relative amounts of the peptide fragment formed by the cleavage were from 2 to 3% (PRR-4D and PRR-4E) or from 20 to 50% (PRR-4A, PRR-4N and PRR-4Q) or almost comparable to PRR (PRR-4K). Based on these results, it is considered that OmpT protease recognizes the electrical charge of the amino acid at the –4-position.

TABLE 5

Cleavage of fusion protein PRR-4X (X being K, A, N, Q, D or E)

| PRR-4X | Relative amount of 4.9 kDa peptide |
|---|---|
| PRR | 100 |
| PRR-4K | 96 |
| PRR-4A | 49 |
| PRR-4N | 48 |
| PRR-4Q | 23 |

TABLE 5-continued

Cleavage of fusion protein PRR-4X (X being K, A, N, Q, D or E)

| PRR-4X | Relative amount of 4.9 kDa peptide |
|---|---|
| PRR-4D | 2.8 |
| PRR-4E | 2.0 |

The 4.9 kDa peptide is formed by the cleavage of the fusion proteins by OmpT protease.
The amount of the 4.9 kDa peptide of PRR is referred to as 100. PRR has Arg at the –4-position.

As shown in FIG. 32, the cleavage by OmpT protease was further examined by using the fusion protein PRR-6X wherein glutamic acid at the –6-position of the fusion protein PRR had been substituted. PRR-6X was reacted with the purified OmpT protease specimen at 25° C. for 60 minutes at pH 7.0. After the enzymatic reaction, SDS-PAGE analysis was performed. FIG. 35B shows the results wherein – represents a lane free from OmpT protease, and + represents a lane with the addition of OmpT protease (0.1 U/ml).

Although the cleavage by OmpT protease was observed in all of the fusion proteins, the amount of the 4.9 kDa peptide fragment formed by the cleavage differed from protein to protein similar to the case of PRR-4X.

Then the 4.9 kDa peptide fragment was quantitated by using HPLC. Table 6 shows the data of the relative amounts of the 4.9 kDa peptide fragment calculated by referring the amount in the case of PRR as to 100. The relative amounts of the peptide fragment formed by the cleavage were almost comparable to PRR (PRR-6D), from about 3 to 4 times as much as PRR (PRR-6A, PRR-6N and PRR-6Q) or about 10 times as much as PRR (PRR-6R and PRR-6K). Based on these results, it is considered that OmpT protease recognizes also the electrical charge of the amino acid at the –6-position too.

TABLE 6

Cleavage of fusion protein PRR-6X (X being R, K, A, N, Q or D)

| PRR-6X | Relative amount of 4.9 kDa peptide |
|---|---|
| PRR | 100 |
| PRR-6R | 1000 |
| PRR-6K | 1400 |
| PRR-6A | 310 |
| PRR-6N | 430 |
| PRR-6Q | 390 |
| PRR-6D | 110 |

The 4.9 kDa peptide is formed by the cleavage of the fusion proteins by OmpT protease.
The amount of the 4.9 kDa peptide of PRR is referred to as 100. PRR has Glu at the –6-position.

These results suggest that OmpT protease recognizes the amino acids at the –4- and –6-positions in the digested site of the substrate and the cleavage ratio is elevated in the case wherein the amino acids at these positions are basic amino acids but lowered in the case wherein the amino acids at these positions are acidic amino acids.

Example 16

Application to Sequence Cleavable by OmpT Protease

Based on the results of Example 15, it is assumed that the cleavage efficiency of OmpT protease can be elevated by converting the amino acids at the –4- and –6-positions of the known OmpT protease cleavage site into basic amino acids.

From this viewpoint, a fusion protein RShANPR (FIG. 36) was formed by substituting the amino acids at the −4- and −6-positions of the OmpT protease cleavage site of the fusion protein RShANP (FIG. 21), having a structure cleavable by OmpT protease and thus releasing α-hANP, by arginine (a basic amino acid) and then it was examined by the following three steps whether or not these fusion proteins differed from each other in the cleavage by OmpT protease.

(Step 1) Construction of pGRShANPR (FIG. 37)

The expression plasmid of the fusion protein RShANPR, wherein alanine at the −4-position and tyrosine at the −6-position of the OmpT protease cleavage site -QMHGYDAQFR↓SLRR- (SEQ ID NO: 99) of the fusion protein RShANP had been substituted each by arginine, was referred to as pGRShANPR. These conversions were carried out by introducing DNA mutations into pGRShANP.

The DNA mutations were introduced by PCR. As shown in FIG. 37, pGRShANP was used as a template and P10 and P44: 5'-ATGCACGGTCGTGATCGTCAATTCCGTAGC-3' (SEQ ID NO: 100) were used as primers. As the product of PCR with the use of the combinations of the primers P10/P44, a 0.3 kbp fragment (fragment 48) was obtained. Then PCR was carried out again by using pGRShANP as a template and the P3 and the fragment 48 as primers to give the 0.6 kbp fragment (fragment 49). The 0.2 kbp fragment (fragment 50) obtained by digesting fragment 49 with BglII and EcoRI was ligated to the 3.0 kbp fragment (fragment 51) obtained by digesting pGRShANP with BglII and EcoRI, and transformation was carried out. A plasmid was isolated from each clone thus obtained and restriction enzyme analysis and nucleotide sequencing at the mutated site were performed so that it was identified as the expression plasmid pGRShANPR of the target fusion protein RShANPR.

(Step 2) Preparation of Fusion Proteins RShANP and RShANPR

When pGRShANP and pGRShANPR are expressed in *E. coli*, the fusion proteins RShANP and RShANPR (FIG. 36) are expressed as inclusion body. In a case where OmpT protease is expressed in *E. coli*, these inclusion body is cleaved by OmpT protease merely by dissolving with urea. To avoid the cleavage, therefore, pGRShANP and pGRShANPR were transformed into the OmpT protease-deficient *E. coli* strain W3110M25 and thus the fusion proteins RShANP and RShANPR were prepared in the form of inclusion body.

(Step 3) Cleavage of Fusion Proteins RShANP and RShANPR by OmpT Protease

RShANP and RShANPR were reacted with the purified OmpT protease specimen at 25° C. for 90 minutes at pH 7.0. After the completion of the enzymatic reaction, the peptide fragment thus released was quantitated by HPLC. In the case of adding OmpT protease (2.0 U/ml), a peak was detected at the retention time of 4.7 minutes. By isolating this peak and determining the N-terminal amino acid sequence, it was identified as α-hANP.

The relative peak area at the retention time of 4.7 minutes (i.e., the relative amount of the released α-hANP) of RShANPR was 2.2 times as much as that of RShANP. Based on these results, it is expected that the cleavage efficiently by OmpT protease can be elevated by converting the amino acids at the −6- and −4-positions of the known OmpT protease cleavage site into basic amino acids (arginine in the above case).

EFFECTS OF THE INVENTION

In one aspect, the present invention makes use of the property of OmpT protease which is that OmpT protease shows a highly specific effect of exclusively cleaving the bonds between arginine-X and lysine-X (wherein X represents an amino acid other than glutamic acid, aspartic acid or proline) located in specific amino acid sequences. Therefore, use of OmpT protease makes it possible to, for example, select a peptide constructing from amino acids other than glutamic acid, aspartic acid or proline as the N-terminal amino acid in the case of excising the target peptide from a fusion protein expressed by genetic engineering techniques, and to avoid the cleavage at undesired peptide bonds by converting the amino acid at the +1-position into glutamic acid, aspartic acid or proline.

In another aspect, the present invention makes use of another property of OmpT protease which is that OmpT protease recognizes the charges of the amino acids at the −6- and −4-positions. In case of excising the target peptide from a fusion protein expressed by genetic engineering techniques similar to the above-described case, the cleavage ratio can be elevated by converting the amino acids at the −6- and −4-positions into basic amino acids and the cleavage at undesired peptide bonds can be minimized by converting the amino acids at the −6- and −4-positions into acidic amino acids. When a fusion protein is expressed in inclusion body, OmpT protease is recovered together with the inclusion body. Therefore, the present invention is particularly effective in the case of using *E. coli* as a host.

SEQUENCE LISTING

```
<160> NUMBER OF SEQ ID NOS: 132

<210> SEQ ID NO 1
<211> LENGTH: 8
<212> TYPE: PRT
<213> ORGANISM: Artificial Sequence
<220> FEATURE:
<223> OTHER INFORMATION: OmpT protease cleavage site

<400> SEQUENCE: 1

Arg Leu Tyr Arg Arg His His Gly
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(5)
<223> OTHER INFORMATION: Xaa: Gly, Ala, Val, Leu, Ile, Met, Pro, Phe,
      Trp, Ser, Thr, Asn, Gln, Tyr, Cys, Lys, Arg, His, Asp, Glu

<400> SEQUENCE: 2

Arg Leu Tyr Arg Xaa His His Gly
1               5

<210> SEQ ID NO 3
<211> LENGTH: 24
<212> TYPE: DNA
<213> ORGANISM: Artificial Sequence
<220> FEATURE:
<223> OTHER INFORMATION: Primer (P1)

<400> SEQUENCE: 3
gactcagatc ttcctgaggc cgat                                              24

<210> SEQ ID NO 4
<211> LENGTH: 36
<212> TYPE: DNA
<213> ORGANISM: Artificial Sequence
<220> FEATURE:
<223> OTHER INFORMATION: Primer (P2)

<400> SEQUENCE: 4
aaaggtacct tccgcatgcc gcggatgtcg agaagg                                 36

<210> SEQ ID NO 5
<211> LENGTH: 184
<212> TYPE: PRT
<213> ORGANISM: Artificial Sequence
<220> FEATURE:
<223> OTHER INFORMATION: Fusion protein

<400> SEQUENCE: 5

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Asp Asp Ala Arg Thr Asp Arg Pro
            35                  40                  45

Ser Gln Gln Leu Arg Ser Leu Asn Gly Glu Trp Arg Phe Ala Trp Phe
        50                  55                  60

Pro Ala Pro Glu Ala Val Pro Glu Ser Leu Leu Asp Leu Pro Glu Ala
65                  70                  75                  80

Asp Thr Val Val Val Pro Asp Ser Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Pro His His His Pro Gly Gly Arg Gln
        115                 120                 125

Met His Gly Tyr Asp Ala Glu Leu Arg Leu Tyr Arg Arg His His Gly
    130                 135                 140
```

```
Ser Gly Ser Pro Ser Arg His Pro Arg His Ala Glu Gly Thr Phe Thr
145                 150                 155                 160

Ser Asp Val Ser Ser Tyr Leu Glu Gly Gln Ala Ala Lys Glu Phe Ile
                165                 170                 175

Ala Trp Leu Val Leu Gly Arg Gly
            180
```

```
<210> SEQ ID NO 6
<211> LENGTH: 20
<212> TYPE: DNA
<213> ORGANISM: Artificial Sequence
<220> FEATURE:
<223> OTHER INFORMATION: Primer (P3)

<400> SEQUENCE: 6
accccaggct ttacacttta                                              20

<210> SEQ ID NO 7
<211> LENGTH: 29
<212> TYPE: DNA
<213> ORGANISM: Artificial Sequence
<220> FEATURE:
<223> OTHER INFORMATION: Primer (P4X)
<220> FEATURE:
<221> NAME/KEY: misc_feature
<222> LOCATION: (15)..(17)
<223> OTHER INFORMATION: nnn: gct, gtt, ctt, att, cct, ttt, tgg, atg,
      ggt, agt, act, tgt, tat, cgt, cag, gat, gaa, aaa, cat, cgt

<400> SEQUENCE: 7
ccggatccgt gatgnnngcg atacaggcg                                    29

<210> SEQ ID NO 8
<211> LENGTH: 29
<212> TYPE: DNA
<213> ORGANISM: Artificial Sequence
<220> FEATURE:
<223> OTHER INFORMATION: Primer (P5)

<400> SEQUENCE: 8
acggatccgg ttcccttat cgacatccg                                     29

<210> SEQ ID NO 9
<211> LENGTH: 20
<212> TYPE: DNA
<213> ORGANISM: Artificial Sequence
<220> FEATURE:
<223> OTHER INFORMATION: Primer (P6)

<400> SEQUENCE: 9
ttgcgcattc acagttctcc                                              20

<210> SEQ ID NO 10
<211> LENGTH: 20
<212> TYPE: DNA
<213> ORGANISM: Artificial Sequence
<220> FEATURE:
<223> OTHER INFORMATION: Primer (P7)

<400> SEQUENCE: 10
gcgggtgttg gcgggtgtcg                                              20

<210> SEQ ID NO 11
<211> LENGTH: 27
<212> TYPE: DNA
<213> ORGANISM: Artificial Sequence
```

-continued

<220> FEATURE:
<223> OTHER INFORMATION: Primer (P8)

<400> SEQUENCE: 11
tgaattcttc ctgtgtgaaa ttgttat                                    27

<210> SEQ ID NO 12
<211> LENGTH: 30
<212> TYPE: DNA
<213> ORGANISM: Artificial Sequence
<220> FEATURE:
<223> OTHER INFORMATION: Primer (P9)

<400> SEQUENCE: 12
tgaattcaaa atgcgggcga aactgctggg                                 30

<210> SEQ ID NO 13
<211> LENGTH: 20
<212> TYPE: DNA
<213> ORGANISM: Artificial Sequence
<220> FEATURE:
<223> OTHER INFORMATION: Primer (P10)

<400> SEQUENCE: 13
tgccgaggat gacgatgagc                                            20

<210> SEQ ID NO 14
<211> LENGTH: 20
<212> TYPE: DNA
<213> ORGANISM: Artificial Sequence
<220> FEATURE:
<223> OTHER INFORMATION: Primer (P11)

<400> SEQUENCE: 14
ctatcgtcgc cgcacttatg                                            20

<210> SEQ ID NO 15
<211> LENGTH: 39
<212> TYPE: DNA
<213> ORGANISM: Artificial Sequence
<220> FEATURE:
<223> OTHER INFORMATION: Primer (P12)

<400> SEQUENCE: 15
tgaattcttc ctgtctgtaa tttttatccg ctcacaatt                       39

<210> SEQ ID NO 16
<211> LENGTH: 9
<212> TYPE: PRT
<213> ORGANISM: Artificial Sequence
<220> FEATURE:
<223> OTHER INFORMATION: OmpT protease cleavage site of fusion protein
      PRA

<400> SEQUENCE: 16

Leu Tyr Arg Ala His His Gly Ser Gly
1               5

<210> SEQ ID NO 17
<211> LENGTH: 9
<212> TYPE: PRT
<213> ORGANISM: Artificial Sequence
<220> FEATURE:
<223> OTHER INFORMATION: OmpT protease cleavage site of fusion protein
      PRV

<400> SEQUENCE: 17

```
Leu Tyr Arg Val His His Gly Ser Gly
1               5

<210> SEQ ID NO 18
<211> LENGTH: 9
<212> TYPE: PRT
<213> ORGANISM: Artificial Sequence
<220> FEATURE:
<223> OTHER INFORMATION: OmpT protease cleavage site of fusion protein
      PRL

<400> SEQUENCE: 18

Leu Tyr Arg Leu His His Gly Ser Gly
1               5

<210> SEQ ID NO 19
<211> LENGTH: 9
<212> TYPE: PRT
<213> ORGANISM: Artificial Sequence
<220> FEATURE:
<223> OTHER INFORMATION: OmpT protease cleavage site of fusion protein
      PRI

<400> SEQUENCE: 19

Leu Tyr Arg Ile His His Gly Ser Gly
1               5

<210> SEQ ID NO 20
<211> LENGTH: 9
<212> TYPE: PRT
<213> ORGANISM: Artificial Sequence
<220> FEATURE:
<223> OTHER INFORMATION: OmpT protease non-cleavage site of fusion
      protein PRP

<400> SEQUENCE: 20

Leu Tyr Arg Pro His His Gly Ser Gly
1               5

<210> SEQ ID NO 21
<211> LENGTH: 9
<212> TYPE: PRT
<213> ORGANISM: Artificial Sequence
<220> FEATURE:
<223> OTHER INFORMATION: OmpT protease cleavage site of fusion protein
      PRF

<400> SEQUENCE: 21

Leu Tyr Arg Phe His His Gly Ser Gly
1               5

<210> SEQ ID NO 22
<211> LENGTH: 9
<212> TYPE: PRT
<213> ORGANISM: Artificial Sequence
<220> FEATURE:
<223> OTHER INFORMATION: OmpT protease cleavage site of fusion protein
      PRW

<400> SEQUENCE: 22

Leu Tyr Arg Trp His His Gly Ser Gly
1               5

<210> SEQ ID NO 23
<211> LENGTH: 9
<212> TYPE: PRT
<213> ORGANISM: Artificial Sequence
```

```
<220> FEATURE:
<223> OTHER INFORMATION: OmpT protease cleavage site of fusion protein
      PRM

<400> SEQUENCE: 23

Leu Tyr Arg Met His His Gly Ser Gly
1               5

<210> SEQ ID NO 24
<211> LENGTH: 9
<212> TYPE: PRT
<213> ORGANISM: Artificial Sequence
<220> FEATURE:
<223> OTHER INFORMATION: OmpT protease cleavage site of fusion protein
      PRG

<400> SEQUENCE: 24

Leu Tyr Arg Gly His His Gly Ser Gly
1               5

<210> SEQ ID NO 25
<211> LENGTH: 9
<212> TYPE: PRT
<213> ORGANISM: Artificial Sequence
<220> FEATURE:
<223> OTHER INFORMATION: OmpT protease cleavage site of fusion protein
      PRS

<400> SEQUENCE: 25

Leu Tyr Arg Ser His His Gly Ser Gly
1               5

<210> SEQ ID NO 26
<211> LENGTH: 9
<212> TYPE: PRT
<213> ORGANISM: Artificial Sequence
<220> FEATURE:
<223> OTHER INFORMATION: OmpT protease cleavage site of fusion protein
      PRT

<400> SEQUENCE: 26

Leu Tyr Arg Thr His His Gly Ser Gly
1               5

<210> SEQ ID NO 27
<211> LENGTH: 9
<212> TYPE: PRT
<213> ORGANISM: Artificial Sequence
<220> FEATURE:
<223> OTHER INFORMATION: OmpT protease cleavage site of fusion protein
      PRC

<400> SEQUENCE: 27

Leu Tyr Arg Cys His His Gly Ser Gly
1               5

<210> SEQ ID NO 28
<211> LENGTH: 9
<212> TYPE: PRT
<213> ORGANISM: Artificial Sequence
<220> FEATURE:
<223> OTHER INFORMATION: OmpT protease cleavage site of fusion protein
      PRY

<400> SEQUENCE: 28

Leu Tyr Arg Tyr His His Gly Ser Gly
1               5
```

```
<210> SEQ ID NO 29
<211> LENGTH: 9
<212> TYPE: PRT
<213> ORGANISM: Artificial Sequence
<220> FEATURE:
<223> OTHER INFORMATION: OmpT protease cleavage site of fusion protein
      PRN

<400> SEQUENCE: 29

Leu Tyr Arg Asn His His Gly Ser Gly
1               5

<210> SEQ ID NO 30
<211> LENGTH: 9
<212> TYPE: PRT
<213> ORGANISM: Artificial Sequence
<220> FEATURE:
<223> OTHER INFORMATION: OmpT protease cleavage site of fusion protein
      PRQ

<400> SEQUENCE: 30

Leu Tyr Arg Gln His His Gly Ser Gly
1               5

<210> SEQ ID NO 31
<211> LENGTH: 9
<212> TYPE: PRT
<213> ORGANISM: Artificial Sequence
<220> FEATURE:
<223> OTHER INFORMATION: OmpT protease non-cleavage site of fusion
      protein PRD

<400> SEQUENCE: 31

Leu Tyr Arg Asp His His Gly Ser Gly
1               5

<210> SEQ ID NO 32
<211> LENGTH: 9
<212> TYPE: PRT
<213> ORGANISM: Artificial Sequence
<220> FEATURE:
<223> OTHER INFORMATION: OmpT protease non-cleavage site of fusion
      protein PRE

<400> SEQUENCE: 32

Leu Tyr Arg Glu His His Gly Ser Gly
1               5

<210> SEQ ID NO 33
<211> LENGTH: 9
<212> TYPE: PRT
<213> ORGANISM: Artificial Sequence
<220> FEATURE:
<223> OTHER INFORMATION: OmpT protease cleavage site of fusion protein
      PRK

<400> SEQUENCE: 33

Leu Tyr Arg Lys His His Gly Ser Gly
1               5

<210> SEQ ID NO 34
<211> LENGTH: 9
<212> TYPE: PRT
<213> ORGANISM: Artificial Sequence
<220> FEATURE:
<223> OTHER INFORMATION: OmpT protease cleavage site of fusion protein
      PRR
```

```
<400> SEQUENCE: 34

Leu Tyr Arg Arg His His Gly Ser Gly
1               5

<210> SEQ ID NO 35
<211> LENGTH: 9
<212> TYPE: PRT
<213> ORGANISM: Artificial Sequence
<220> FEATURE:
<223> OTHER INFORMATION: OmpT protease cleavage site of fusion protein
      PRH

<400> SEQUENCE: 35

Leu Tyr Arg His His His Gly Ser Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (5)..(5)
<223> OTHER INFORMATION: Xaa: Ala, Ser, Lys, Arg, Asp, Glu

<400> SEQUENCE: 36

Arg Leu Tyr Lys Xaa His His Gly
1               5

<210> SEQ ID NO 37
<211> LENGTH: 29
<212> TYPE: DNA
<213> ORGANISM: Artificial Sequence
<220> FEATURE:
<223> OTHER INFORMATION: Primer (P13X)
<220> FEATURE:
<221> NAME/KEY: misc_feature
<222> LOCATION: (15)..(17)
<223> OTHER INFORMATION: nnn: agc, aga, ttt, acg, gtc,ttc

<400> SEQUENCE: 37
ccggatccgt gatgnnnttt atacaggcg                                       29

<210> SEQ ID NO 38
<211> LENGTH: 9
<212> TYPE: PRT
<213> ORGANISM: Artificial Sequence
<220> FEATURE:
<223> OTHER INFORMATION: OmpT protease cleavage site of fusion protein
      PKA

<400> SEQUENCE: 38

Leu Tyr Lys Ala His His Gly Ser Gly
1               5

<210> SEQ ID NO 39
<211> LENGTH: 9
<212> TYPE: PRT
<213> ORGANISM: Artificial Sequence
<220> FEATURE:
<223> OTHER INFORMATION: OmpT protease cleavage site of fusion protein
      PKS

<400> SEQUENCE: 39

Leu Tyr Lys Ser His His Gly Ser Gly
1               5
```

```
<210> SEQ ID NO 40
<211> LENGTH: 9
<212> TYPE: PRT
<213> ORGANISM: Artificial Sequence
<220> FEATURE:
<223> OTHER INFORMATION: OmpT protease cleavage site of fusion protein
      PKK

<400> SEQUENCE: 40

Leu Tyr Lys Lys His His Gly Ser Gly
1               5

<210> SEQ ID NO 41
<211> LENGTH: 9
<212> TYPE: PRT
<213> ORGANISM: Artificial Sequence
<220> FEATURE:
<223> OTHER INFORMATION: OmpT protease cleavage site of fusion protein
      PKR

<400> SEQUENCE: 41

Leu Tyr Lys Arg His His Gly Ser Gly
1               5

<210> SEQ ID NO 42
<211> LENGTH: 9
<212> TYPE: PRT
<213> ORGANISM: Artificial Sequence
<220> FEATURE:
<223> OTHER INFORMATION: OmpT protease non-cleavage site of fusion
      protein PKD

<400> SEQUENCE: 42

Leu Tyr Lys Asp His His Gly Ser Gly
1               5

<210> SEQ ID NO 43
<211> LENGTH: 9
<212> TYPE: PRT
<213> ORGANISM: Artificial Sequence
<220> FEATURE:
<223> OTHER INFORMATION: OmpT protease non-cleavage site of fusion
      protein PKE

<400> SEQUENCE: 43

Leu Tyr Lys Glu His His Gly Ser Gly
1               5

<210> SEQ ID NO 44
<211> LENGTH: 41
<212> TYPE: DNA
<213> ORGANISM: Artificial Sequence
<220> FEATURE:
<223> OTHER INFORMATION: Primer (P14)

<400> SEQUENCE: 44
gcggagctcc gcctgtatcg cagcctgcgg agatccagct g                    41

<210> SEQ ID NO 45
<211> LENGTH: 20
<212> TYPE: DNA
<213> ORGANISM: Artificial Sequence
<220> FEATURE:
<223> OTHER INFORMATION: Primer (P15)

<400> SEQUENCE: 45
```

-continued ctgagtcgac tcagtaccgg                                              20

<210> SEQ ID NO 46
<211> LENGTH: 41
<212> TYPE: DNA
<213> ORGANISM: Artificial Sequence
<220> FEATURE:
<223> OTHER INFORMATION: Primer (P16)

<400> SEQUENCE: 46
gcggagctcc gcctgtatcg ctgtggtaac ctgagcacct g                      41

<210> SEQ ID NO 47
<211> LENGTH: 20
<212> TYPE: DNA
<213> ORGANISM: Artificial Sequence
<220> FEATURE:
<223> OTHER INFORMATION: Primer (P17)

<400> SEQUENCE: 47
ctgagtcgac ttagcccggg                                              20

<210> SEQ ID NO 48
<211> LENGTH: 27
<212> TYPE: DNA
<213> ORGANISM: Artificial Sequence
<220> FEATURE:
<223> OTHER INFORMATION: Primer (P18)

<400> SEQUENCE: 48
tacgatgcgc aattccgtag cctgcgg                                      27

<210> SEQ ID NO 49
<211> LENGTH: 31
<212> TYPE: DNA
<213> ORGANISM: Artificial Sequence
<220> FEATURE:
<223> OTHER INFORMATION: Primer (P19)

<400> SEQUENCE: 49
tgcctgactg cgttagcaat ttaactgtga t                                 31

<210> SEQ ID NO 50
<211> LENGTH: 20
<212> TYPE: DNA
<213> ORGANISM: Artificial Sequence
<220> FEATURE:
<223> OTHER INFORMATION: Primer (P21)

<400> SEQUENCE: 50
ttatcgccac tggcagcagc                                              20

<210> SEQ ID NO 51
<211> LENGTH: 129
<212> TYPE: PRT
<213> ORGANISM: Artificial Sequence
<220> FEATURE:
<223> OTHER INFORMATION: Fusion protein

<400> SEQUENCE: 51

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro

-continued

```
                35                  40                  45
Ser Gln Gln Leu Arg Ser Leu Asn Gly Glu Trp Arg Phe Ala Trp Phe
     50                  55                  60

Pro Ala Pro Glu Ala Val Pro Glu Ser Leu Leu Glu Leu Pro Glu Ala
 65                  70                  75                  80

Asp Thr Val Val Val Pro Asp Ser Ser Asn Thr Gln Met His Gly Tyr
                 85                  90                  95

Asp Ala Gln Phe Arg Ser Leu Arg Arg Ser Ser Cys Phe Gly Gly Arg
            100                 105                 110

Met Asp Arg Ile Gly Ala Gln Ser Gly Leu Gly Cys Asn Ser Phe Arg
            115                 120                 125

Tyr

<210> SEQ ID NO 52
<211> LENGTH: 8
<212> TYPE: PRT
<213> ORGANISM: Artificial Sequence
<220> FEATURE:
<223> OTHER INFORMATION: OmpT protease cleavage site of fusion protein
      RShANP

<400> SEQUENCE: 52

Gln Phe Arg Ser Leu Arg Arg Ser
 1               5

<210> SEQ ID NO 53
<211> LENGTH: 8
<212> TYPE: PRT
<213> ORGANISM: Artificial Sequence
<220> FEATURE:
<223> OTHER INFORMATION: OmpT protease cleavage site of fusion protein
      RRhANP

<400> SEQUENCE: 53

Gln Phe Arg Arg Leu Arg Arg Ser
 1               5

<210> SEQ ID NO 54
<211> LENGTH: 8
<212> TYPE: PRT
<213> ORGANISM: Artificial Sequence
<220> FEATURE:
<223> OTHER INFORMATION: OmpT protease cleavage site of fusion protein
      RAhANP

<400> SEQUENCE: 54

Gln Phe Arg Ala Leu Arg Arg Ser
 1               5

<210> SEQ ID NO 55
<211> LENGTH: 8
<212> TYPE: PRT
<213> ORGANISM: Artificial Sequence
<220> FEATURE:
<223> OTHER INFORMATION: OmpT protease cleavage site of fusion protein
      RChANP

<400> SEQUENCE: 55

Gln Phe Arg Cys Leu Arg Arg Ser
 1               5

<210> SEQ ID NO 56
<211> LENGTH: 8
<212> TYPE: PRT
```

```
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (5)..(5)
<223> OTHER INFORMATION: Xaa: Arg, Ala, Cys

<400> SEQUENCE: 56

Ala Gln Phe Arg Xaa Leu Arg Arg
1               5

<210> SEQ ID NO 57
<211> LENGTH: 30
<212> TYPE: DNA
<213> ORGANISM: Artificial Sequence
<220> FEATURE:
<223> OTHER INFORMATION: Primer (P22X)
<220> FEATURE:
<221> NAME/KEY: misc_feature
<222> LOCATION: (10)..(12)
<223> OTHER INFORMATION: nnn: gct, tgt, cgt

<400> SEQUENCE: 57
tctccgcagn nnacggaatt gcgcatcgta                                       30

<210> SEQ ID NO 58
<211> LENGTH: 30
<212> TYPE: DNA
<213> ORGANISM: Artificial Sequence
<220> FEATURE:
<223> OTHER INFORMATION: Primer (P23X)
<220> FEATURE:
<221> NAME/KEY: misc_feature
<222> LOCATION: (10)..(12)
<223> OTHER INFORMATION: nnn: gct, tgt, cgt

<400> SEQUENCE: 58
caattccgtn nnctgcggag atccagctgc                                       30

<210> SEQ ID NO 59
<211> LENGTH: 30
<212> TYPE: DNA
<213> ORGANISM: Artificial Sequence
<220> FEATURE:
<223> OTHER INFORMATION: Primer (P24)

<400> SEQUENCE: 59
gcctgactgc gttagcaatt taactgtgat                                       30

<210> SEQ ID NO 60
<211> LENGTH: 6
<212> TYPE: PRT
<213> ORGANISM: Artificial Sequence
<220> FEATURE:
<223> OTHER INFORMATION: Fusion protein

<400> SEQUENCE: 60

Pro Ser Arg His Lys Arg
1               5

<210> SEQ ID NO 61
<211> LENGTH: 23
<212> TYPE: PRT
<213> ORGANISM: Artificial Sequence
<220> FEATURE:
<223> OTHER INFORMATION: Fusion protein

<400> SEQUENCE: 61
```

```
Gln Met His Gly Tyr Asp Ala Glu Leu Arg Leu Tyr Arg Arg His His
1               5                   10                  15

Arg Thr Gly Arg Ser Gly Ser
            20
```

<210> SEQ ID NO 62
<211> LENGTH: 20
<212> TYPE: PRT
<213> ORGANISM: Artificial Sequence
<220> FEATURE:
<223> OTHER INFORMATION: Fusion protein

<400> SEQUENCE: 62

```
Gln Met His Gly Tyr Asp Ala Glu Leu Arg Leu Tyr Arg Arg His His
1               5                   10                  15

Gly Ser Gly Ser
            20
```

<210> SEQ ID NO 63
<211> LENGTH: 6
<212> TYPE: PRT
<213> ORGANISM: Artificial Sequence
<220> FEATURE:
<223> OTHER INFORMATION: Fusion protein

<400> SEQUENCE: 63

```
Pro Ser Arg His Pro Arg
1               5
```

<210> SEQ ID NO 64
<211> LENGTH: 26
<212> TYPE: PRT
<213> ORGANISM: Artificial Sequence
<220> FEATURE:
<223> OTHER INFORMATION: Fusion protein

<400> SEQUENCE: 64

```
Gln Met His Gly Tyr Asp Ala Glu Leu Arg Leu Tyr Arg Arg His His
1               5                   10                  15

Gly Ser Gly Ser Pro Ser Arg His Pro Arg
            20                  25
```

<210> SEQ ID NO 65
<211> LENGTH: 53
<212> TYPE: DNA
<213> ORGANISM: Artificial Sequence
<220> FEATURE:
<223> OTHER INFORMATION: Primer

<400> SEQUENCE: 65
aattgtgagc ggataacaat tcacacagg aagaattcat gcgggcgaaa ctt          53

<210> SEQ ID NO 66
<211> LENGTH: 56
<212> TYPE: DNA
<213> ORGANISM: Artificial Sequence
<220> FEATURE:
<223> OTHER INFORMATION: Primer

<400> SEQUENCE: 66
aattgtgagc ggataacaat tcacacagg aagaattcaa aatgcgggcg aaactg       56

<210> SEQ ID NO 67
<211> LENGTH: 53

```
<212> TYPE: DNA
<213> ORGANISM: Artificial Sequence
<220> FEATURE:
<223> OTHER INFORMATION: Primer

<400> SEQUENCE: 67
aattgtgagc ggataaaaat tacagacagg aagaattcat gcgggcgaaa ctt            53

<210> SEQ ID NO 68
<211> LENGTH: 56
<212> TYPE: DNA
<213> ORGANISM: Artificial Sequence
<220> FEATURE:
<223> OTHER INFORMATION: Primer

<400> SEQUENCE: 68
aattgtgagc ggataaaaat tacagacagg aagaattcaa aatgcgggcg aaactg         56

<210> SEQ ID NO 69
<211> LENGTH: 3
<212> TYPE: PRT
<213> ORGANISM: Artificial Sequence
<220> FEATURE:
<223> OTHER INFORMATION: Fusion protein

<400> SEQUENCE: 69

Gln Phe Lys
1

<210> SEQ ID NO 70
<211> LENGTH: 26
<212> TYPE: PRT
<213> ORGANISM: Artificial Sequence
<220> FEATURE:
<223> OTHER INFORMATION: Fusion protein

<400> SEQUENCE: 70

Gln Met His Gly Tyr Asp Ala Glu Leu Arg Leu Tyr Arg Arg His His
1               5                   10                  15

Gly Ser Gly Ser Pro Tyr Arg His Pro Arg
            20                  25

<210> SEQ ID NO 71
<211> LENGTH: 13
<212> TYPE: PRT
<213> ORGANISM: Artificial Sequence
<220> FEATURE:
<223> OTHER INFORMATION: Fusion protein

<400> SEQUENCE: 71

Gln Met His Gly Tyr Asp Ala Glu Leu Arg Leu Tyr Arg
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Fusion protein

<400> SEQUENCE: 72

Glu Phe Arg His His Arg Arg His Arg Leu Glu
1               5                   10

<210> SEQ ID NO 73
<211> LENGTH: 3
```

```
<212> TYPE: PRT
<213> ORGANISM: Artificial Sequence
<220> FEATURE:
<223> OTHER INFORMATION: Fusion protein

<400> SEQUENCE: 73

Gln Phe Arg
1

<210> SEQ ID NO 74
<211> LENGTH: 69
<212> TYPE: DNA
<213> ORGANISM: Artificial Sequence
<220> FEATURE:
<223> OTHER INFORMATION: Primer

<400> SEQUENCE: 74
cagatgcatg gttatgacgc ggagctccgg ctgtatcgcc gtcatcaccg gtggggtcgt    60
tccggatcc                                                            69

<210> SEQ ID NO 75
<211> LENGTH: 69
<212> TYPE: DNA
<213> ORGANISM: Artificial Sequence
<220> FEATURE:
<223> OTHER INFORMATION: Primer

<400> SEQUENCE: 75
ggatccggaa cgaccccacc ggtgatgacg gcgatacagc cggagctccg cgtcataacc    60
atgcatctg                                                            69

<210> SEQ ID NO 76
<211> LENGTH: 47
<212> TYPE: DNA
<213> ORGANISM: Artificial Sequence
<220> FEATURE:
<223> OTHER INFORMATION: Primer

<400> SEQUENCE: 76
tggttatgac gcggagctcc gcctgtatcg ccgtcatcac ggttccg                  47

<210> SEQ ID NO 77
<211> LENGTH: 55
<212> TYPE: DNA
<213> ORGANISM: Artificial Sequence
<220> FEATURE:
<223> OTHER INFORMATION: Primer

<400> SEQUENCE: 77
gatccggaac cgtgatgacg gcgatacagg cggagctccg cgtcataacc atgca         55

<210> SEQ ID NO 78
<211> LENGTH: 17
<212> TYPE: PRT
<213> ORGANISM: Artificial Sequence
<220> FEATURE:
<223> OTHER INFORMATION: OmpT protease cleavage site in the linker
      peptide of PRR

<400> SEQUENCE: 78

Gln Met His Gly Tyr Asp Ala Glu Leu Arg Leu Tyr Arg Arg His His
1               5                   10                  15

Gly
```

<210> SEQ ID NO 79
<211> LENGTH: 10
<212> TYPE: PRT
<213> ORGANISM: Artificial Sequence
<220> FEATURE:
<223> OTHER INFORMATION: Amino acid sequence from -10- to -1- positions
of the OmpT protease cleavage site in the linker peptide of PRR
which was modified in Example 12 for the preparation of fusion
protein PRRXA

<400> SEQUENCE: 79

Gly Tyr Asp Ala Glu Leu Arg Leu Tyr Arg
1               5                   10

<210> SEQ ID NO 80
<211> LENGTH: 30
<212> TYPE: DNA
<213> ORGANISM: Artificial Sequence
<220> FEATURE:
<223> OTHER INFORMATION: Primer (P25)

<400> SEQUENCE: 80
gcggagctcc gcctggctcg ccgtcatcac                                      30

<210> SEQ ID NO 81
<211> LENGTH: 30
<212> TYPE: DNA
<213> ORGANISM: Artificial Sequence
<220> FEATURE:
<223> OTHER INFORMATION: Primer (P26)

<400> SEQUENCE: 81
gcggagctcc gcgcttatcg ccgtcatcac                                      30

<210> SEQ ID NO 82
<211> LENGTH: 30
<212> TYPE: DNA
<213> ORGANISM: Artificial Sequence
<220> FEATURE:
<223> OTHER INFORMATION: Primer (P27)

<400> SEQUENCE: 82
gcggagctcg ctctgtatcg ccgtcatcac                                      30

<210> SEQ ID NO 83
<211> LENGTH: 30
<212> TYPE: DNA
<213> ORGANISM: Artificial Sequence
<220> FEATURE:
<223> OTHER INFORMATION: Primer (P28)

<400> SEQUENCE: 83
cagatgcatg gttatgacgc ggaggctcgc                                      30

<210> SEQ ID NO 84
<211> LENGTH: 30
<212> TYPE: DNA
<213> ORGANISM: Artificial Sequence
<220> FEATURE:
<223> OTHER INFORMATION: Primer (P29)

<400> SEQUENCE: 84
cagatgcatg gttatgacgc ggctctccgc                                      30

<210> SEQ ID NO 85
<211> LENGTH: 30
<212> TYPE: DNA

<213> ORGANISM: Artificial Sequence
<220> FEATURE:
<223> OTHER INFORMATION: Primer (P30)

<400> SEQUENCE: 85
gcggagctcc gcagcataac catgcatctg  30

<210> SEQ ID NO 86
<211> LENGTH: 30
<212> TYPE: DNA
<213> ORGANISM: Artificial Sequence
<220> FEATURE:
<223> OTHER INFORMATION: Primer (P31)

<400> SEQUENCE: 86
gcggagctcc gcgtcagcac catgcatctg  30

<210> SEQ ID NO 87
<211> LENGTH: 30
<212> TYPE: DNA
<213> ORGANISM: Artificial Sequence
<220> FEATURE:
<223> OTHER INFORMATION: Primer (P32)

<400> SEQUENCE: 87
gcggagctcc gcgtcataag catgcatctg  30

<210> SEQ ID NO 88
<211> LENGTH: 30
<212> TYPE: DNA
<213> ORGANISM: Artificial Sequence
<220> FEATURE:
<223> OTHER INFORMATION: Primer (P33)

<400> SEQUENCE: 88
gcggagctcc gcctgtatgc tcgtcatcac  30

<210> SEQ ID NO 89
<211> LENGTH: 30
<212> TYPE: DNA
<213> ORGANISM: Artificial Sequence
<220> FEATURE:
<223> OTHER INFORMATION: Primer (P34)

<400> SEQUENCE: 89
gcggagctca aactgtatcg ccgtcatcac  30

<210> SEQ ID NO 90
<211> LENGTH: 30
<212> TYPE: DNA
<213> ORGANISM: Artificial Sequence
<220> FEATURE:
<223> OTHER INFORMATION: Primer (P35)

<400> SEQUENCE: 90
gcggagctcg acctgtatcg ccgtcatcac  30

<210> SEQ ID NO 91
<211> LENGTH: 30
<212> TYPE: DNA
<213> ORGANISM: Artificial Sequence
<220> FEATURE:
<223> OTHER INFORMATION: Primer (P36)

<400> SEQUENCE: 91
gcggagctcg aactgtatcg ccgtcatcac  30

```
<210> SEQ ID NO 92
<211> LENGTH: 30
<212> TYPE: DNA
<213> ORGANISM: Artificial Sequence
<220> FEATURE:
<223> OTHER INFORMATION: Primer (P37)

<400> SEQUENCE: 92
gcggagctca acctgtatcg ccgtcatcac                              30

<210> SEQ ID NO 93
<211> LENGTH: 30
<212> TYPE: DNA
<213> ORGANISM: Artificial Sequence
<220> FEATURE:
<223> OTHER INFORMATION: Primer (P38)

<400> SEQUENCE: 93
gcggagctcc agctgtatcg ccgtcatcac                              30

<210> SEQ ID NO 94
<211> LENGTH: 30
<212> TYPE: DNA
<213> ORGANISM: Artificial Sequence
<220> FEATURE:
<223> OTHER INFORMATION: Primer (P39)

<400> SEQUENCE: 94
cagatgcatg gttatgacgc gcgtctccgc                              30

<210> SEQ ID NO 95
<211> LENGTH: 30
<212> TYPE: DNA
<213> ORGANISM: Artificial Sequence
<220> FEATURE:
<223> OTHER INFORMATION: Primer (P40)

<400> SEQUENCE: 95
cagatgcatg gttatgacgc gaaactccgc                              30

<210> SEQ ID NO 96
<211> LENGTH: 30
<212> TYPE: DNA
<213> ORGANISM: Artificial Sequence
<220> FEATURE:
<223> OTHER INFORMATION: Primer (P41)

<400> SEQUENCE: 96
cagatgcatg gttatgacgc ggacctccgc                              30

<210> SEQ ID NO 97
<211> LENGTH: 30
<212> TYPE: DNA
<213> ORGANISM: Artificial Sequence
<220> FEATURE:
<223> OTHER INFORMATION: Primer (P42)

<400> SEQUENCE: 97
cagatgcatg gttatgacgc gaacctccgc                              30

<210> SEQ ID NO 98
<211> LENGTH: 30
<212> TYPE: DNA
<213> ORGANISM: Artificial Sequence
<220> FEATURE:
```

```
<223> OTHER INFORMATION: Primer (P43)

<400> SEQUENCE: 98
cagatgcatg gttatgacgc gcagctccgc                                          30

<210> SEQ ID NO 99
<211> LENGTH: 14
<212> TYPE: PRT
<213> ORGANISM: Artificial Sequence
<220> FEATURE:
<223> OTHER INFORMATION: OmpT protease cleavage site of RShANP

<400> SEQUENCE: 99

Gln Met His Gly Tyr Asp Ala Gln Phe Arg Ser Leu Arg Arg
1               5                   10

<210> SEQ ID NO 100
<211> LENGTH: 30
<212> TYPE: DNA
<213> ORGANISM: Artificial Sequence
<220> FEATURE:
<223> OTHER INFORMATION: Primer (P44)

<400> SEQUENCE: 100
atgcacggtc gtgatcgtca attccgtagc                                          30

<210> SEQ ID NO 101
<211> LENGTH: 14
<212> TYPE: PRT
<213> ORGANISM: Artificial Sequence
<220> FEATURE:
<223> OTHER INFORMATION: Partial sequence of PRR (Figs. 25, 31 and 32)

<400> SEQUENCE: 101

Gly Tyr Asp Ala Glu Leu Arg Leu Tyr Arg Arg His His Gly
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Partial sequence of PRR-1A (Fig. 25)

<400> SEQUENCE: 102

Gly Tyr Asp Ala Glu Leu Arg Leu Tyr Ala Arg His His Gly
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Partial sequence of PRR-2A (Fig. 25)

<400> SEQUENCE: 103

Gly Tyr Asp Ala Glu Leu Arg Leu Ala Arg Arg His His Gly
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Partial sequence of PRR-3A (Fig. 25)

<400> SEQUENCE: 104
```

Gly Tyr Asp Ala Glu Leu Arg Ala Tyr Arg Arg His His Gly
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Partial sequence of PRR-4A (Fig. 25)

<400> SEQUENCE: 105

Gly Tyr Asp Ala Glu Leu Ala Leu Tyr Arg Arg His His Gly
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Partial sequence of PRR-5A (Fig. 25)

<400> SEQUENCE: 106

Gly Tyr Asp Ala Glu Ala Arg Leu Tyr Arg Arg His His Gly
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Partial sequence of PRR-6a (Fig. 25)

<400> SEQUENCE: 107

Gly Tyr Asp Ala Ala Leu Arg Leu Tyr Arg Arg His His Gly
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Partial sequence of PRR-8A (Fig. 25)

<400> SEQUENCE: 108

Gly Tyr Ala Ala Glu Leu Arg Leu Tyr Arg Arg His His Gly
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Partial sequence of PRR-9A (Fig. 25)

<400> SEQUENCE: 109

Gly Ala Asp Ala Glu Leu Arg Leu Tyr Arg Arg His His Gly
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Partial sequence of PRR-10A (Fig. 25)

<400> SEQUENCE: 110

```
Ala Tyr Asp Ala Glu Leu Arg Leu Tyr Arg Arg His His Gly
1               5                   10
```

<210> SEQ ID NO 111
<211> LENGTH: 14
<212> TYPE: PRT
<213> ORGANISM: Artificial Sequence
<220> FEATURE:
<223> OTHER INFORMATION: Partial sequence of PRR-4K (Fig. 31)

<400> SEQUENCE: 111

```
Gly Tyr Asp Ala Glu Leu Lys Leu Tyr Arg Arg His His Gly
1               5                   10
```

<210> SEQ ID NO 112
<211> LENGTH: 14
<212> TYPE: PRT
<213> ORGANISM: Artificial Sequence
<220> FEATURE:
<223> OTHER INFORMATION: Partial sequence of PRR-4A (Fig. 31)

<400> SEQUENCE: 112

```
Gly Tyr Asp Ala Glu Leu Ala Leu Tyr Arg Arg His His Gly
1               5                   10
```

<210> SEQ ID NO 113
<211> LENGTH: 14
<212> TYPE: PRT
<213> ORGANISM: Artificial Sequence
<220> FEATURE:
<223> OTHER INFORMATION: Partial sequence of PRR-4N (Fig. 31)

<400> SEQUENCE: 113

```
Gly Tyr Asp Ala Glu Leu Asn Leu Tyr Arg Arg His His Gly
1               5                   10
```

<210> SEQ ID NO 114
<211> LENGTH: 14
<212> TYPE: PRT
<213> ORGANISM: Artificial Sequence
<220> FEATURE:
<223> OTHER INFORMATION: Partial sequence of Prr-4Q (Fig. 31)

<400> SEQUENCE: 114

```
Gly Tyr Asp Ala Glu Leu Gln Leu Tyr Arg Arg His His Gly
1               5                   10
```

<210> SEQ ID NO 115
<211> LENGTH: 14
<212> TYPE: PRT
<213> ORGANISM: Artificial Sequence
<220> FEATURE:
<223> OTHER INFORMATION: Partial sequence of PRR-4D (Fig. 31)

<400> SEQUENCE: 115

```
Gly Tyr Asp Ala Glu Leu Asp Leu Tyr Arg Arg His His Gly
1               5                   10
```

<210> SEQ ID NO 116
<211> LENGTH: 14
<212> TYPE: PRT
<213> ORGANISM: Artificial Sequence
<220> FEATURE:
<223> OTHER INFORMATION: Partial sequence of PRR-4E (Fig. 31)

<400> SEQUENCE: 116

```
Gly Tyr Asp Ala Glu Leu Glu Leu Tyr Arg Arg His His Gly
```

```
<210> SEQ ID NO 117
<211> LENGTH: 14
<212> TYPE: PRT
<213> ORGANISM: Artificial Sequence
<220> FEATURE:
<223> OTHER INFORMATION: Partial sequence of PRR-6R (Fig. 32)

<400> SEQUENCE: 117

Gly Tyr Asp Ala Arg Leu Arg Leu Tyr Arg Arg His His Gly
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Partial sequence of PRR-6K (Fig. 32)

<400> SEQUENCE: 118

Gly Tyr Asp Ala Lys Leu Arg Leu Tyr Arg Arg His His Gly
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Partial sequence of PRR-6A (Fig. 32)

<400> SEQUENCE: 119

Gly Tyr Asp Ala Ala Leu Arg Leu Tyr Arg Arg His His Gly
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Partial sequence of PRR-6N (Fig. 32)

<400> SEQUENCE: 120

Gly Tyr Asp Ala Asn Leu Arg Leu Tyr Arg Arg His His Gly
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Partial sequence of PRR-6Q (Fig. 32)

<400> SEQUENCE: 121

Gly Tyr Asp Ala Gln Leu Arg Leu Tyr Arg Arg His His Gly
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Partial sequence of PRR-6D (Fig. 32)

<400> SEQUENCE: 122

Gly Tyr Asp Ala Asp Leu Arg Leu Tyr Arg Arg His His Gly
1               5                   10
```

<210> SEQ ID NO 123
<211> LENGTH: 16
<212> TYPE: PRT
<213> ORGANISM: Artificial Sequence
<220> FEATURE:
<223> OTHER INFORMATION: Partial sequence of RShANP (Fig. 36)

<400> SEQUENCE: 123

Gln Met His Gly Tyr Asp Ala Gln Phe Arg Ser Leu Arg Leu Arg Arg
1               5                   10                  15

<210> SEQ ID NO 124
<211> LENGTH: 14
<212> TYPE: PRT
<213> ORGANISM: Artificial Sequence
<220> FEATURE:
<223> OTHER INFORMATION: Partial sequence of RShANPR (Fig. 36)

<400> SEQUENCE: 124

Gln Met His Gly Arg Asp Arg Gln Phe Arg Ser Leu Arg Arg
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 125

Ala Gln Phe Arg Ser Leu Arg Arg
1               5

<210> SEQ ID NO 126
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 126

Glu Leu Arg Leu Tyr Arg Pro His His Gly
1               5                   10

<210> SEQ ID NO 127
<211> LENGTH: 26
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: Xaa: Gly, Ala, Val, Leu, Ile, Met, Pro, Phe,
      Trp, Ser, Thr, Asn, Gln, Tyr, Cys, Lys, Arg, His, Asp, Glu

<400> SEQUENCE: 127

Gln Met His Gly Tyr Asp Ala Glu Leu Arg Leu Tyr Arg Xaa His His
1               5                   10                  15

Gly Ser Gly Ser Pro Tyr Arg His Pro Arg
            20                  25

<210> SEQ ID NO 128
<211> LENGTH: 26
<212> TYPE: PRT
<213> ORGANISM: Artificial Sequence

```
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: Xaa: Gly, Ala, Val, Leu, Ile, Met, Pro, Phe,
      Trp, Ser, Thr, Asn, Gln, Tyr, Cys, Lys, Arg, His, Asp, Glu

<400> SEQUENCE: 128

Gln Met His Gly Tyr Asp Ala Glu Leu Arg Leu Tyr Lys Xaa His His
1               5                   10                  15

Gly Ser Gly Ser Pro Tyr Arg His Pro Arg
            20                  25

<210> SEQ ID NO 129
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 129

Gln Met His Gly Tyr Asp Ala Glu Leu Arg Leu Tyr Arg Ser Leu Arg
1               5                   10                  15

Arg Ser Ser Cys Phe Gly Gly Arg Met Asp Arg Ile Gly Ala Gln Ser
            20                  25                  30

Gly Leu Gly Cys Asn Ser Phe Arg Tyr
35                  40

<210> SEQ ID NO 130
<211> LENGTH: 46
<212> TYPE: PRT
<213> ORGANISM: Artificial Sequence
<220> FEATURE:
<223> OTHER INFORMATION: Chemically Synthesized

<400> SEQUENCE: 130

Gln Met His Gly Tyr Asp Ala Glu Leu Arg Leu Tyr Arg Cys Gly Asn
1               5                   10                  15

Leu Ser Thr Cys Met Leu Gly Thr Tyr Thr Gln Asp Phe Asn Lys Phe
            20                  25                  30

His Thr Phe Pro Gln Thr Ala Ile Gly Val Gly Ala Pro Gly
            35                  40                  45

<210> SEQ ID NO 131
<211> LENGTH: 129
<212> TYPE: PRT
<213> ORGANISM: Artificial Sequence
<220> FEATURE:
<223> OTHER INFORMATION: Chemically Synthesized

<400> SEQUENCE: 131

Met Thr Met Ile Thr Asp Ser Leu Ala Val Val Leu Gln Arg Lys Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Leu Leu Glu Leu Pro Glu Ala
65                  70                  75                  80
```

-continued

```
Asp Thr Val Val Val Pro Asp Ser Ser Asn Trp Gln Met His Gly Tyr
                85              90                  95

Asp Ala Gln Phe Arg Ser Leu Arg Arg Ser Ser Cys Phe Gly Gly Arg
            100             105                 110

Met Asp Arg Ile Gly Ala Gln Ser Gly Leu Gly Cys Asn Ser Phe Arg
        115             120                 125

Tyr

<210> SEQ ID NO 132
<211> LENGTH: 31
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (4)..(4)
<223> OTHER INFORMATION: Xaa: Gly, Ala, Val, Leu, Ile, Met, Pro, Phe,
      Trp, Ser, Thr, Asn, Gln, Tyr, Cys, Lys, Arg, His, Asp, Glu

<400> SEQUENCE: 132

Gln Phe Arg Xaa Leu Arg Arg Ser Ser Cys Phe Gly Gly Arg Met Asp
1               5                   10                  15

Arg Ile Gly Ala Gln Ser Gly Leu Gly Cys Asn Ser Phe Arg Tyr
            20                  25                  30
```

What is claimed is:

1. A method for elevating the cleavage efficiency of *E. coli* OmpT protease on a polypeptide at a sequence site, −1 and +1 positions, which is originally cleavable by *E. coli* OmpT protease, comprising setting an amino acid other than acidic amino acids as the amino acid at the −4-position and/or the −6-position relative to said sequence site in said polypeptide.

2. A method for elevating the cleavage efficiency of *E. coli* OmpT protease on a polypeptide at a sequence site, −1 and +1 positions, which is originally cleavable by *E. coli* OmpT protease, comprising amino acid conversion in the polypeptide by, in a case where the amino acid at the −4 and/or −6 position relative to said sequence site is an acidic amino acid, setting a neutral amino acid or a basic amino acid as said amino acid at the −4 and/or −6 position, or in a case where the amino acid at the −4 and/or −6 position is a neutral amino acid, setting a basic amino acid as said amino acid at the −4 and/or −6 position.

3. A method for elevating the cleavage efficiency of *E. coli* OmpT protease on a polypeptide having a sequence site which consists of two arbitrary consecutive amino acids at −1 and +1 positions and which is cleavable by *E. coli* OmpT protease, wherein said method comprises:
   (1) setting lysine or arginine as the amino acid at the −1-position of said site,
   (2) setting an amino acid X, wherein X is an amino acid other than glutamic acid, aspartic acid or proline, as the amino acid at the +1-position, and
   (3) amino acid conversion to set an amino acid other than acidic amino acids as the amino acid at the −4-position and/or the −6-position relative to said sequence site.

4. A method for elevating the cleavage efficiency of *E. coli* OmpT protease on a polypeptide having a sequence site which consists of two arbitrary consecutive amino acids at −1 and +1 positions and which is cleavable by *E. coli* OmpT protease, which method comprises:
   (1) setting lysine or arginine as the amino acid at the −1-position of said site, setting an amino acid X, wherein X is an amino acid other than glutamic acid, aspartic acid or proline, as the amino acid at the +1-position, and
   (2) in a case where the amino acid at the −4 and/or −6 position relative to said sequence site is an acidic amino acid, converting said amino acid at the −4 and/or −6 position to a neutral amino acid or a basic amino acid, or in a case where the amino acid at the −4 and/or −6 position is a neutral amino acid, converting said amino acid at the −4 and/or −6 position to a basic amino acid.

5. The method of any one of claims 1, 2, 3, and 4, wherein a basic amino acid is set as the amino acid at −4 and/or −6 position relative to the sequence site.

6. A method for lowering the cleavage efficiency of *E. coli* OmpT protease on a polypeptide at a sequence site, −1 and +1 positions, which is originally cleavable by *E. coli* OmpT protease, comprising amino acid conversion in the polypeptide by setting a neutral amino acid or an acidic amino acid as the amino acid at the −4-position and/or the −6-position relative to said sequence site.

7. A method for lowering the cleavage efficiency of *E. coli* OmpT protease on a polypeptide having a sequence site which consists of two arbitrary consecutive amino acids at −1 and +1 positions and which is cleavable by *E. coli* OmpT protease, which method comprises:
   (1) setting lysine or arginine as the amino acid at the −1-position of said site, setting an amino acid X, wherein X is an amino acid other than glutamic acid, aspartic acid or proline, as the amino acid at the +1-position, and
   (2) amino acid conversion to set a neutral amino acid or an acidic amino acid as the amino acid at the −4-position and/or the −6-position relative to said sequence site.

8. A method for lowering the cleavage efficiency of *E. coli* OmpT protease on a polypeptide at a sequence site, −1 and +1 positions, which is originally cleavable by *E. coli* OmpT protease, comprising amino acid conversion in the polypeptide by in a case where the amino acid at the −4 and/or −6 position relative to said sequence site is a basic amino acid, setting a neutral amino acid or an acidic amino acid as said amino acid at the −4 and/or −6 position, or in a case where the amino acid at the −4 and/or −6 position is a neutral amino acid, setting an acidic amino acid as said amino acid at the −4 and/or −6 position.

9. A method for lowering the cleavage efficiency of *E. coli* OmpT protease on a polypeptide having a sequence site which consists of two arbitrary consecutive amino acids at −1 and +1 positions and which is cleavable by *E. coli* OmpT protease, wherein the method comprises:

(1) setting lysine or arginine as the amino acid at the −1-position of said site, setting an amino acid X, wherein X is an amino acid other than glutamic acid, aspartic acid or proline, as the amino acid at the +1-position, and (2) in a case where the amino acid at the −4 and/or −6 position relative to said sequence site is a basic amino acid, converting said amino acid at the −4 and/or −6 position to a neutral amino acid or an acidic amino acid, or in a case where the amino acid at the −4 and/or −6 position is a neutral amino acid, converting said amino acid at the −4 and/or −6 position to an acidic amino acid.

10. The method of any one of claims 6-9, wherein an acidic amino acid is set as the amino acid at the −4 and/or −6 position relative to the sequence site.

* * * * *